(12) United States Patent
Duch et al.

(10) Patent No.: US 8,470,600 B2
(45) Date of Patent: Jun. 25, 2013

(54) BIOCOMPATIBLE MATERIALS FOR MAMMALIAN STEM CELL GROWTH AND DIFFERENTIATION

(75) Inventors: Mogens Ryttergård Duch, Risskov (DK); Lotte Markert, Århus V (DK); Jette Lovmand, Malling (DK); Annette Christine Füchtbauer, Højbjerg (DK); Ernst Martin Füchtbauer, Højbjerg (DK); Morten Foss, Skanderborg (DK); Flemming Besenbacher, Århus V (DK); Finn Skou Pedersen, Århus V (DK)

(73) Assignee: Aarhus Universitet, Arhus C (DK)

( * ) Notice: Subject to any disclaimer, the term of this patent is extended or adjusted under 35 U.S.C. 154(b) by 135 days.

(21) Appl. No.: 12/994,617

(22) PCT Filed: May 27, 2009

(86) PCT No.: PCT/EP2009/056443
§ 371 (c)(1),
(2), (4) Date: Feb. 28, 2011

(87) PCT Pub. No.: WO2009/150051
PCT Pub. Date: Dec. 17, 2009

(65) Prior Publication Data
US 2011/0160869 A1    Jun. 30, 2011

(30) Foreign Application Priority Data

May 27, 2008 (DK) ................................. 2008 00726
May 27, 2008 (DK) ................................. 2008 00730

(51) Int. Cl.
*C12N 5/00* (2006.01)

(52) U.S. Cl.
USPC ........... 435/395; 433/25; 433/167; 623/20.17

(58) Field of Classification Search
USPC .................. 435/395; 623/20.17; 433/25, 167
See application file for complete search history.

(56) References Cited

U.S. PATENT DOCUMENTS

| | | | |
|---|---|---|---|
| 6,197,575 B1 * | 3/2001 | Griffith et al. | 435/288.4 |
| 6,767,928 B1 * | 7/2004 | Murphy et al. | 521/51 |

* cited by examiner

*Primary Examiner* — Susan Hanley
*Assistant Examiner* — Nghi Nguyen

(57) ABSTRACT

A biocompatible material, wherein at least a part of a surface of the biocompatible material is characterized by a micro or nano-meter scale topographical structure comprising a plurality of features where the structure is selected to promote the growth of undifferentiated pluripotent stem cells or serve to promote the uniform differentiated growth of stem cells. Furthermore, a biocompatible material is provided having a surface structure and composition that affects a cellular function, in particular cellular functions related to gene induction, cell differentiation and the formation of bone tissue in vivo and ex-vivo.

50 Claims, 34 Drawing Sheets

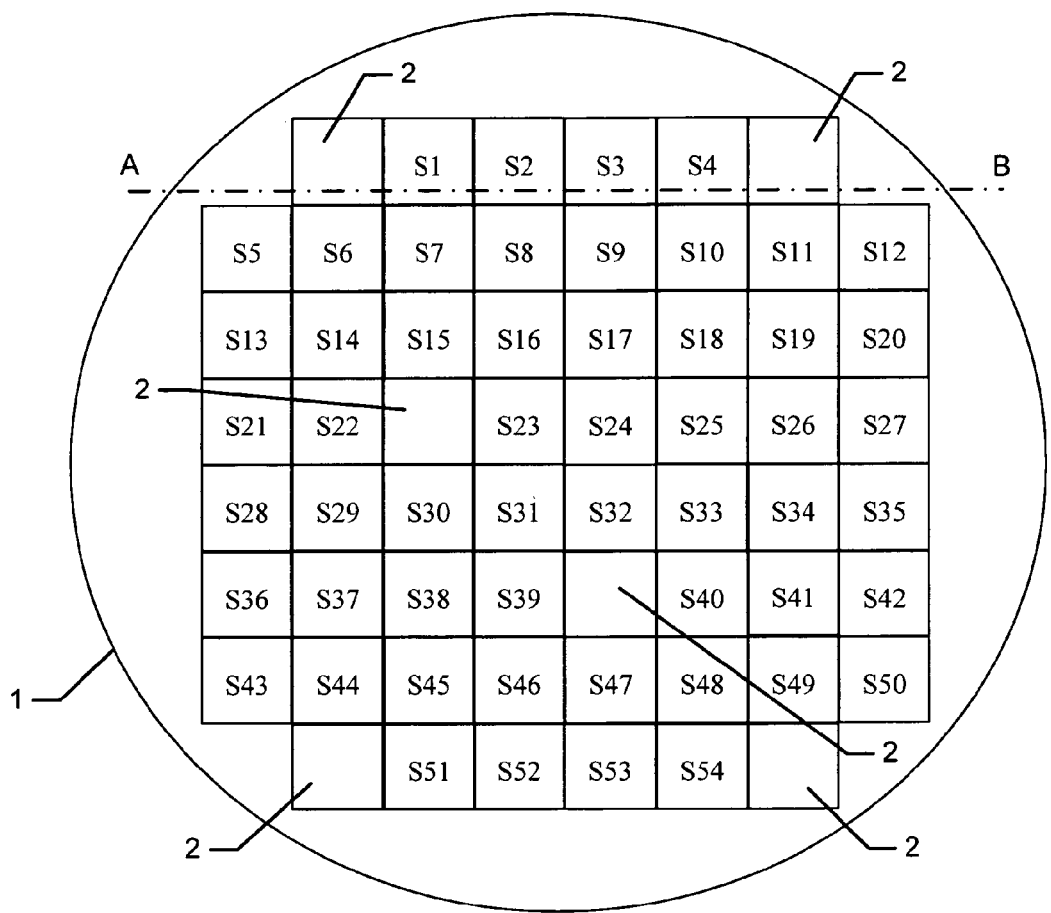
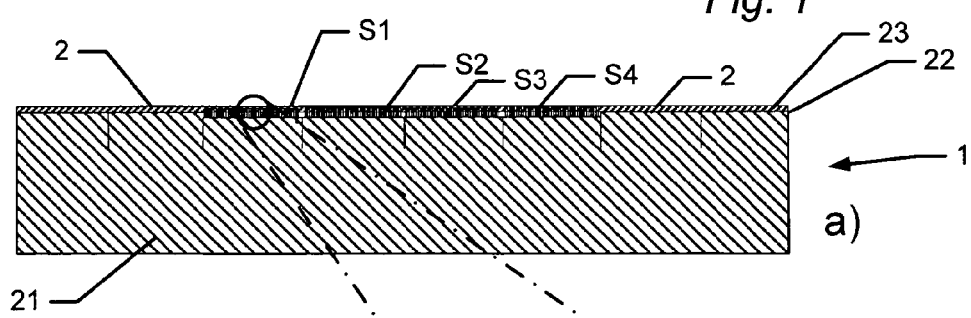
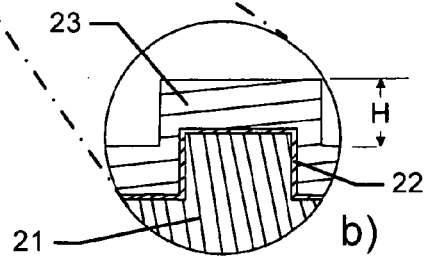
Fig. 1
Fig. 2

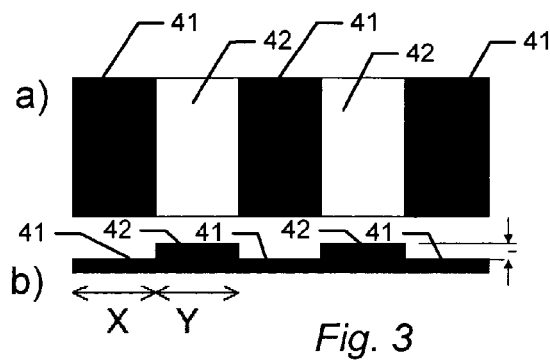
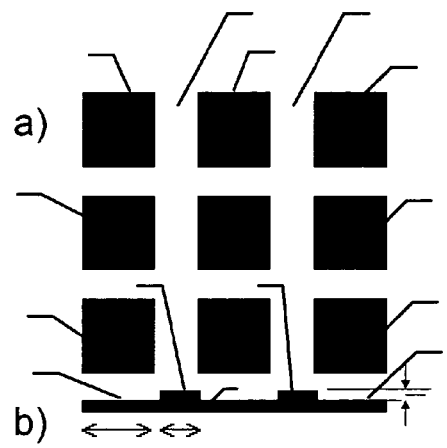
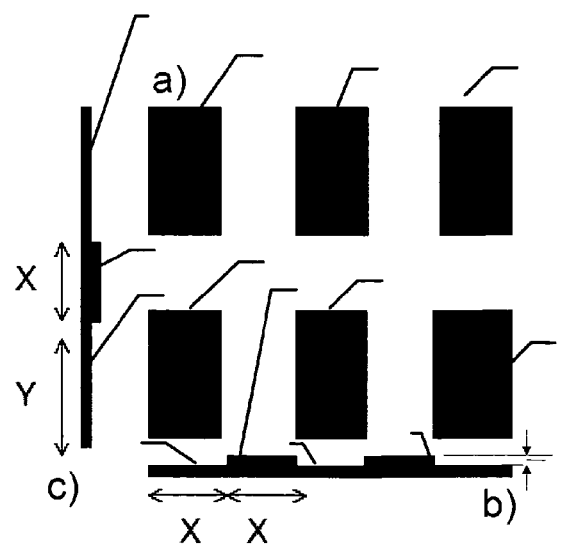

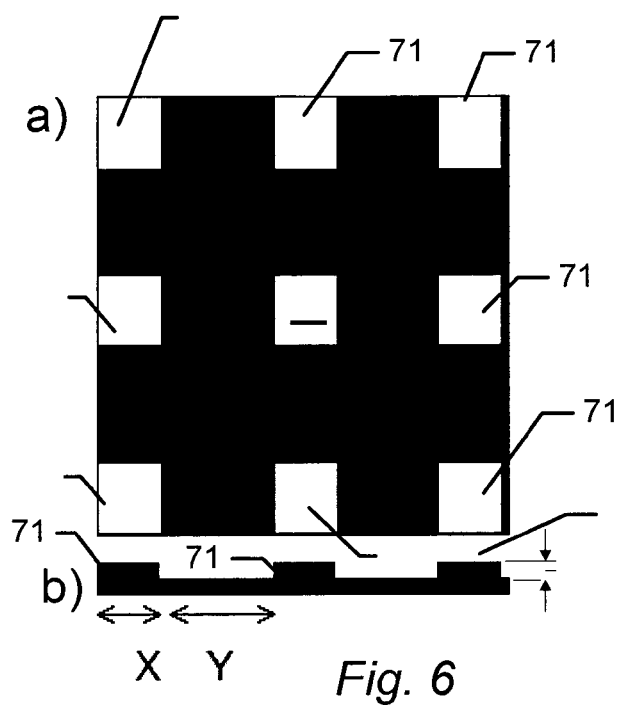
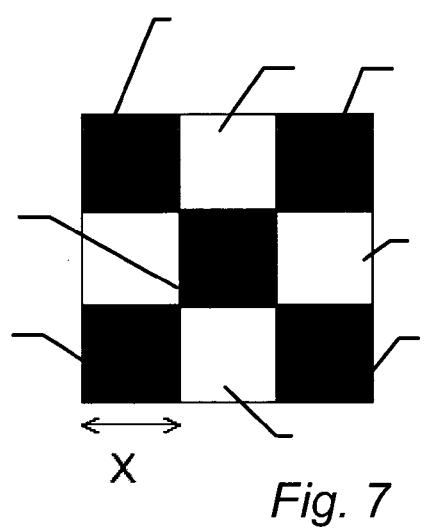
Fig. 6
Fig. 7

ES cell colony morphology
KH2 cells

Colony formation on feeder cells   Colony formation on gelatine

Undifferentiated   Differentiated

| Intracellular markers of pluripotency: | Oct4 |
|---|---|
| | Nanog |
| | Alkaline phosphatase (AP) |

Eksperimental setup

Triple assay with tantalum wafers of varying structure heights

How does the topographical tantalum structures affect ES cell differentiation state?

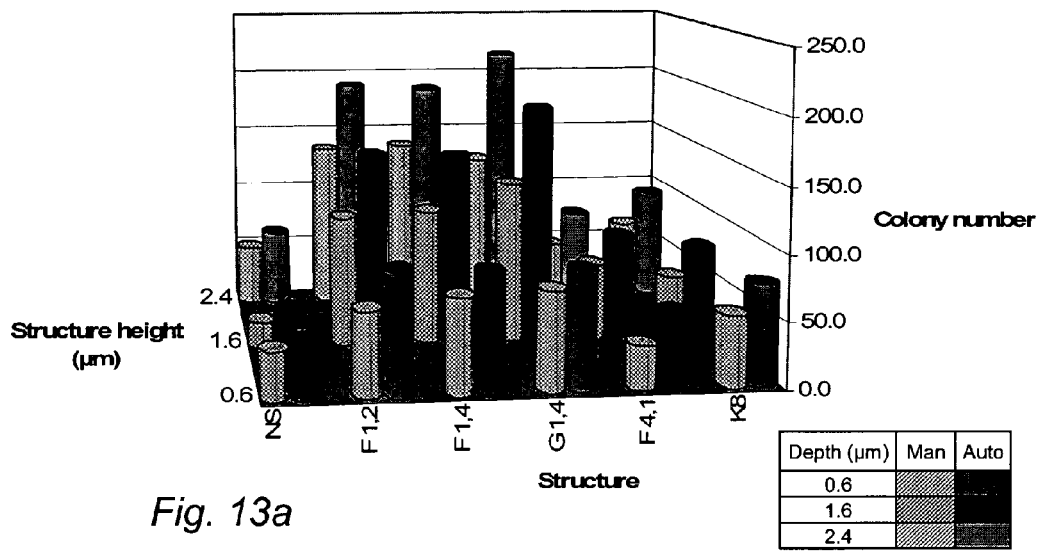
Fig. 13a
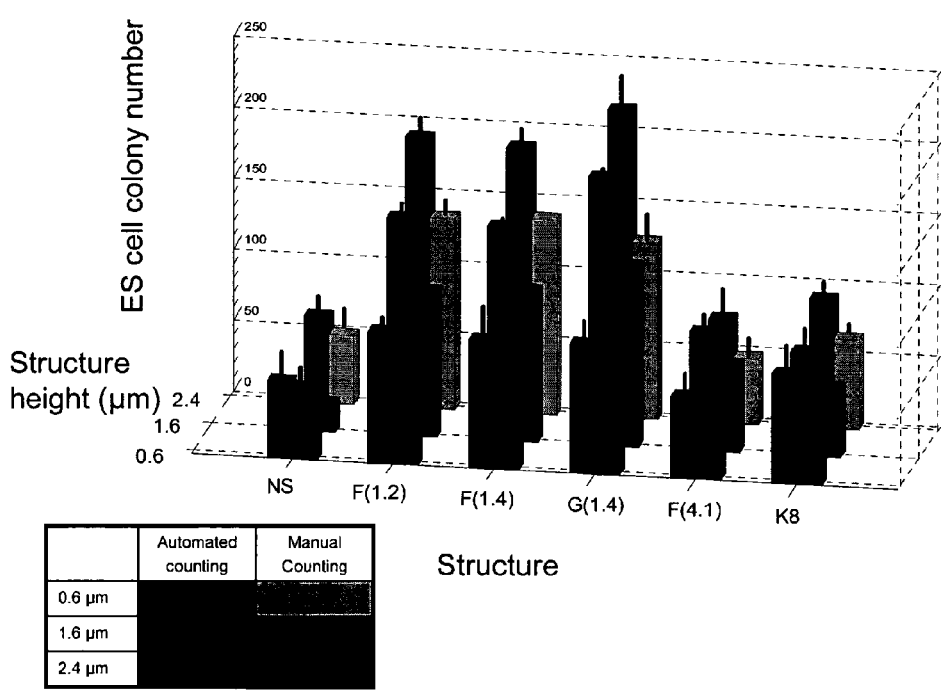
Figure 13b: Automated versus manual counting with standard deviations

| X | 1 | | | | 2 | | | | 4 | | | | 6 | | | | |
|---|---|---|---|---|---|---|---|---|---|---|---|---|---|---|---|---|---|
| Y | 1 | 2 | 4 | 6 | 1 | 2 | 4 | 6 | 1 | 2 | 4 | 6 | 1 | 2 | 4 | 6 | |
| A | 81.5 | 92.7 | 97.7 | 77.0 | 44.8 | 59.2 | 93.7 | 82.4 | 41.3 | 70.2 | 68.7 | 95.0 | 72.8 | 58.0 | 82.3 | 86.8 | |
| C | 81.6 | 75.8 | 75.6 | 76.1 | 70.9 | 64.2 | 109.2 | 84.8 | 75.6 | 53.8 | 86.9 | 79.9 | 55.1 | 51.2 | 60.3 | 104.1 | |
| E | 83.3 | 87.9 | 106.1 | 90.3 | 56.4 | 63.6 | 93.5 | 70.4 | 31.7 | 55.0 | 71.6 | 79.3 | 45.5 | 66.5 | 80.6 | 79.4 | |
| I | 87.1 | 81.2 | 86.3 | 78.9 | 58.2 | 62.4 | 74.7 | 68.1 | 42.2 | 51.7 | 60.9 | 103.0 | 69.0 | 61.4 | 84.4 | 102.4 | |
|  | 81.4 | 91.5 | 87.7 | 89.2 | 58.3 | 66.4 | 110.1 | 101.5 | 66.6 | 66.1 | 81.2 | 87.5 | 57.4 | 62.6 | 81.0 | 85.7 | |
|  | 77.3 | 100.4 | 84.7 | 93.5 | 72.5 | 81.2 | 87.2 | 87.8 | 44.1 | 48.2 | 46.6 | 78.0 | 33.3 | 48.3 | 65.7 | 77.6 | |
|  | 98.7 | 98.3 | 89.8 | 72.4 | 61.8 | 76.8 | 92.1 | 59.8 | 42.5 | 53.9 | 100.0 | 84.9 | 40.2 | 55.7 | 93.4 | 104.1 | |
|  | 81.8 | 70.1 | 78.6 | 68.8 | 41.1 | 35.5 | 89.9 | 85.8 | 44.3 | 87.4 | 90.0 | 79.5 | 41.5 | 51.8 | 70.2 | 74.6 | |
|  | 78.9 | 91.8 | 90.8 | 76.2 | 84.3 | 59.6 | 91.9 | 101.8 | 57.2 | 59.0 | 81.5 | 81.4 | 40.3 | 48.8 | 54.5 | 77.8 | NS |
|  | 98.9 | 99.3 | 108.3 | 114.9 | 59.4 | 55.1 | 71.4 | 115.8 | 76.8 | 28. | 76.8 | 93.6 | 53.2 | 61.2 | 84.4 | 85.2 | 52.9 |
| A | 114.7 | 137.0 | 130.0 | 104.8 | 91.3 | 94.3 | 126.0 | 120.6 | 83.6 | 94.4 | 111.5 | 129.5 | 80.0 | 106.7 | 116.6 | 117.1 | |
| C | 118.0 | 151.8 | 117.2 | 125.5 | 93.8 | 132.1 | 125.3 | 122.2 | 87.1 | 101.9 | 137.2 | 125.1 | 98.7 | 103.6 | 126.0 | 121.5 | |
| E | 100.1 | 121.9 | 132.2 | 129.3 | 107.7 | 139.5 | 158.7 | 144.6 | 108.8 | 140.7 | 141.1 | 123.8 | 78.3 | 81.4 | 101.5 | 100.8 | |
| I | 120.9 | 127.6 | 150.1 | 95.7 | 104.7 | 152.7 | 135.7 | 135.0 | 110.3 | 121.5 | 130.0 | 128.0 | 95.4 | 93.1 | 102.8 | 115.5 | |
|  | 145.6 | 154.6 | 148.6 | 116.8 | 93.4 | 118.4 | 142.6 | 124.6 | 106.8 | 104.9 | 122.8 | 127.5 | 89.9 | 122.7 | 113.7 | 94.1 | |
|  | 131.1 | 159.5 | 136.6 | 110.2 | 85.7 | 131.0 | 147.9 | 147.7 | 103.8 | 124.7 | 129.2 | 128.3 | 88.0 | 103.4 | 128.3 | 122.9 | |
|  | 146.8 | 166.4 | 188.5 | 142.4 | 104.4 | 148.4 | 129.0 | 93.8 | 88.9 | 102.6 | 95.6 | 130.1 | 92.8 | 103.9 | 131.3 | 110.3 | |
|  | 142.7 | 150.4 | 169.9 | 131.4 | 111.8 | 132.8 | 133.0 | 127.1 | 85.3 | 125.3 | 123.9 | 79.3 | 82.3 | 83.6 | 92.3 | 113.4 | |
|  | 110.7 | 152.5 | 150.5 | 139.8 | 96.9 | 134.6 | 152.7 | 139.6 | 83.4 | 100.1 | 102.7 | 99.6 | 94.1 | 105.0 | 117.1 | 120.5 | NS |
|  | 134.6 | 155.3 | 142.9 | 107.5 | 61.5 | 122.4 | 140.1 | 116.8 | 77.4 | 121.7 | 149.0 | 128.7 | 84.5 | 101.9 | 111.3 | 104.7 | 30.3 |
| A | 149.0 | 167.4 | 154.4 | 162.9 | 135.6 | 149.3 | 171.1 | 141.6 | 135.6 | 157.6 | 134.4 | 136.9 | 125.6 | 154.5 | 152.5 | 152.1 | |
| C | 156.7 | 161.2 | 171.6 | 163.4 | 158.1 | 159.1 | 141.7 | 135.6 | 101.6 | 159.5 | 164.0 | 161.7 | 117.1 | 145.0 | 158.4 | 155.3 | |
| E | 114.7 | 144.8 | 176.6 | 154.8 | 158.6 | 172.1 | 171.7 | 144.6 | 132.4 | 167.7 | 185.8 | 138.2 | 101.7 | 125.5 | 135.5 | 135.6 | |
| I | 100.2 | 145.6 | 168.5 | 163.6 | 145.5 | 156.6 | 162.8 | 173.4 | 118.7 | 135.6 | 144.1 | 132.6 | 114.4 | 115.9 | 117.3 | 167.2 | |
|  | 174.2 | 185.9 | 191.4 | 152.4 | 140.6 | 160.0 | 162.7 | 167.0 | 141.5 | 135.6 | 144.1 | 132.6 | 125.5 | 164.9 | 163.0 | 164.8 | |
|  | 157.5 | 189.8 | 151.0 | 118.0 | 106.1 | 164.3 | 159.6 | 168.3 | 110.8 | 163.0 | 167.5 | 144.2 | 110.4 | 151.3 | 162.8 | 161.7 | |
|  | 172.0 | 195.9 | 216.0 | 145.5 | 119.8 | 135.6 | 135.6 | 135.6 | 117.0 | 142.3 | 176.6 | 168.0 | 135.6 | 156.6 | 153.1 | 165.7 | |
|  | 157.4 | 174.3 | 152.2 | 149.4 | 111.9 | 146.2 | 156.3 | 118.9 | 110.8 | 135.6 | 153.5 | 125.6 | 115.5 | 135.6 | 117.6 | 135.6 | |
|  | 135.6 | 190.2 | 186.1 | 196.4 | 113.5 | 148.4 | 166.3 | 147.1 | 72.7 | 103.7 | 135.6 | 147.5 | 98.4 | 143.9 | 151.1 | 162.1 | NS |
|  | 148.0 | 119.7 | 155.3 | 135.6 | 78.5 | 140.2 | 162.2 | 186.5 | 97.2 | 135.6 | 149.9 | 119.2 | 76.7 | 64.9 | 82.7 | 124.8 | 61.0 |

Row labels (left): 0.6 μm, 1.6 μm, 2.4 μm

| T | 1 | 2 | 3 | 4 | 5 | 6 | 7 | 8 | NS |
|---|---|---|---|---|---|---|---|---|---|
| K (0.6 μm) | 52.6 | 33.9 | 43.8 | 40.8 | 47.9 | 58.6 | 55.1 | 77.9 | 52.9 |
| K (1.6 μm) | 69.1 | 65.0 | 68.6 | 67.3 | 64.6 | 63.9 | 72.4 | 72.4 | 30.3 |
| K (2.4 μm) | 88.2 | 74.4 | 77.4 | 82.9 | 81.4 | 71.3 | 88.3 | 90.4 | 61.0 |

| KH2 | 0.6 | 1.6 | 2.4 |
|---|---|---|---|
| cn<50 | | | |
| 50≤cn<60 | | | |
| 60≤cn<70 | | | |
| 70≤cn<80 | | | |
| 80≤cn<90 | | | |
| 90≤cn<100 | | | |
| 100≤cn<110 | | | |
| 110≤cn<120 | | | |
| 120≤cn<130 | | | |
| 130≤cn<140 | | | |
| 140≤cn<150 | | | |
| 150≤cn<160 | | | |
| 160≤cn<170 | | | |
| 170≤cn<180 | | | |
| 180≤cn | | | |

*Fig. 14b*

CJ7 cells passaged on F1.2 have the potential for germline transmission

| Growth support | # blastocysts injected | Pups live/total | ♂≥50% chimaerism | Mating ♂ | Sterile | Germline |
|---|---|---|---|---|---|---|
| F1,2 | 34 | 16/20 | 5 | 5 | 4 | 1 |
| F4,1 | 41 | 5/7 | 3 | 3 | 1 | 0 |
| Gelatine | 18 | 5/5 | 4 | 4 | 3 | 0 |
| Feeder | 31 | 13/16 | 3 | 6 | 4 | 1 |

| X | 1 | | | | 2 | | | | 4 | | | | 6 | | | |
|---|---|---|---|---|---|---|---|---|---|---|---|---|---|---|---|---|
| Y | 1 | 2 | 4 | 6 | 1 | 2 | 4 | 6 | 1 | 2 | 4 | 6 | 1 | 2 | 4 | 6 |

0.6 μm

| | | | | | | | | | | | | | | | | | |
|---|---|---|---|---|---|---|---|---|---|---|---|---|---|---|---|---|---|
| A | 63.3 | 66.7 | 68.5 | 70.5 | 78.7 | 78.0 | 69.4 | 75.8 | 83.7 | 83.1 | 66.5 | 64.6 | 72.7 | 74.5 | 58.0 | 58.5 | |
| C | 48.4 | 50.9 | 52.9 | 47.7 | 46.5 | 50.4 | 55.8 | 71.6 | 73.8 | 53.9 | 46.3 | 47.8 | 63.8 | 54.1 | 50.1 | 45.7 | |
| E | 58.1 | 72.9 | 61.7 | 52.5 | 45.5 | 45.1 | 46.7 | 43.3 | 51.9 | 57.6 | 54.0 | 57.7 | 72.9 | 79.1 | 81.6 | 69.0 | |
| I | 73.0 | 65.6 | 54.9 | 54.5 | 64.9 | 51.7 | 47.2 | 56.7 | 59.4 | 54.0 | 54.8 | 52.3 | 72.1 | 79.7 | 71.3 | 55.5 | |
| B | 57.5 | 60.1 | 63.4 | 56.3 | 70.9 | 66.7 | 59.2 | 52.0 | 65.9 | 69.3 | 65.1 | 58.4 | 62.4 | 62.0 | 59.4 | 62.4 | |
| D | 43.1 | 38.2 | 52.6 | 55.8 | 76.3 | 67.2 | 45.5 | 40.0 | 57.2 | 54.1 | 42.4 | 45.7 | 53.2 | 54.5 | 58.2 | 49.6 | |
| G | 38.6 | 41.2 | 38.2 | 45.4 | 69.1 | 75.8 | 73.2 | 75.9 | 66.5 | 64.6 | 61.3 | 51.6 | 64.3 | 51.5 | 44.0 | 34.1 | |
| J | 60.0 | 58.4 | 47.5 | 56.7 | 65.6 | 66.8 | 55.6 | 51.9 | 58.9 | 75.2 | 75.6 | 67.3 | 76.7 | 80.8 | 70.8 | 75.2 | |
| F | 48.3 | 42.9 | 41.4 | 45.0 | 56.1 | 55.1 | 49.2 | 56.4 | 76.7 | 85.7 | 80.6 | 67.3 | 60.9 | 62.3 | 55.4 | 41.8 | NS |
| H | 38.8 | 61.4 | 67.8 | 70.1 | 74.4 | 62.5 | 48.7 | 49.2 | 63.3 | 61.4 | 55.8 | 45.7 | 45.9 | 52.5 | 64.7 | 67.0 | 39.9 |

1.6 μm

| | | | | | | | | | | | | | | | | | |
|---|---|---|---|---|---|---|---|---|---|---|---|---|---|---|---|---|---|
| A | 42.4 | 36.2 | 47.9 | 63.9 | 63.3 | 60.6 | 57.2 | 65.9 | 73.0 | 69.7 | 63.9 | 60.6 | 69.3 | 63.2 | 53.0 | 56.7 | |
| C | 51.3 | 37.8 | 43.1 | 45.3 | 51.0 | 46.1 | 45.6 | 59.2 | 66.3 | 50.9 | 40.4 | 41.8 | 60.6 | 59.1 | 54.3 | 53.8 | |
| E | 47.3 | 48.5 | 44.6 | 51.3 | 60.8 | 41.9 | 36.5 | 52.7 | 63.3 | 52.5 | 52.8 | 50.6 | 68.3 | 74.4 | 66.3 | 58.8 | |
| I | 57.0 | 49.3 | 44.3 | 40.2 | 55.9 | 49.1 | 49.8 | 48.0 | 65.8 | 54.7 | 43.7 | 44.6 | 66.9 | 70.7 | 66.6 | 55.2 | |
| B | 39.8 | 41.4 | 42.7 | 51.9 | 64.9 | 57.4 | 47.1 | 49.4 | 62.1 | 56.8 | 61.4 | 51.4 | 54.8 | 53.7 | 58.5 | 53.5 | |
| D | 40.8 | 30.4 | 36.1 | 52.0 | 70.7 | 51.8 | 53.3 | 41.4 | 58.9 | 53.1 | 46.7 | 50.3 | 59.8 | 52.5 | 51.4 | 53.1 | |
| G | 37.1 | 33.1 | 33.2 | 43.4 | 61.7 | 58.9 | 57.4 | 63.8 | 72.2 | 63.6 | 55.3 | 47.2 | 63.8 | 53.4 | 49.4 | 47.3 | |
| J | 45.6 | 38.6 | 48.1 | 49.9 | 63.1 | 54.3 | 49.9 | 51.7 | 66.7 | 55.6 | 56.2 | 49.9 | 75.6 | 67.0 | 68.9 | 70.4 | |
| F | 52.4 | 44.4 | 34.3 | 40.2 | 54.8 | 53.2 | 43.5 | 46.9 | 71.2 | 73.0 | 60.4 | 56.1 | 66.8 | 60.6 | 56.4 | 42.4 | NS |
| H | 43.7 | 39.5 | 45.0 | 60.5 | 71.2 | 56.9 | 42.0 | 46.7 | 63.9 | 59.6 | 45.1 | 47.1 | 60.6 | 52.9 | 54.1 | 59.1 | 46.8 |

2.4 μm

| | | | | | | | | | | | | | | | | | |
|---|---|---|---|---|---|---|---|---|---|---|---|---|---|---|---|---|---|
| A | 41.5 | 30.6 | 31.3 | 46.6 | 48.3 | 38.9 | 42.8 | 54.3 | 57.8 | 49.3 | 48.9 | 48.6 | 51.6 | 54.4 | 46.2 | 37.5 | |
| C | 34.4 | 33.3 | 38.9 | 42.4 | 43.8 | 34.4 | 35.9 | 43.2 | 59.4 | 37.5 | 39.2 | 41.4 | 58.1 | 49.4 | 53.6 | 47.2 | |
| E | 34.1 | 30.0 | 34.7 | 38.3 | 36.9 | 27.8 | 33.3 | 33.5 | 42.9 | 44.1 | 38.4 | 42.1 | 59.4 | 59.4 | 47.2 | 48.4 | |
| I | 36.7 | 24.7 | 24.9 | 32.2 | 44.7 | 36.6 | 29.1 | 28.8 | 46.0 | 42.7 | 34.5 | 44.9 | 48.5 | 46.8 | 39.4 | 38.8 | |
| B | 31.2 | 24.5 | 32.7 | 44.3 | 47.2 | 40.5 | 33.2 | 39.5 | 43.0 | 39.1 | 47.4 | 45.1 | 43.1 | 39.2 | 40.8 | 49.8 | |
| D | 29.2 | 27.6 | 35.4 | 44.7 | 50.5 | 39.6 | 30.9 | 37.3 | 49.3 | 45.6 | 42.3 | 43.0 | 52.3 | 50.1 | 44.5 | 45.5 | |
| G | 22.2 | 29.0 | 28.3 | 32.2 | 37.3 | 38.6 | 38.7 | 46.3 | 47.2 | 36.4 | 34.2 | 34.1 | 49.6 | 38.5 | 35.9 | 34.0 | |
| J | 32.4 | 26.8 | 25.0 | 33.3 | 42.8 | 35.2 | 29.3 | 38.9 | 48.6 | 41.0 | 40.4 | 42.4 | 60.5 | 48.6 | 42.6 | 47.0 | |
| F | 29.6 | 22.4 | 22.2 | 35.7 | 41.9 | 36.2 | 28.6 | 36.9 | 59.2 | 53.5 | 49.1 | 41.3 | 55.5 | 40.7 | 36.0 | 38.9 | NS |
| H | 22.4 | 21.6 | 23.8 | 38.6 | 47.9 | 29.8 | 22.7 | 27.8 | 53.6 | 44.8 | 35.8 | 34.8 | 49.6 | 41.6 | 37.4 | 36.7 | 45.3 |

| T | 1 | 2 | 3 | 4 | 5 | 6 | 7 | 8 | NS |
|---|---|---|---|---|---|---|---|---|---|
| K (0.6 μm) | 72.0 | 75.0 | 75.4 | 78.0 | 71.4 | 65.5 | 70.6 | 75.4 | 39.9 |
| K (1.6 μm) | 73.8 | 73.6 | 77.4 | 80.8 | 73.3 | 65.6 | 66.4 | 60.4 | 46.8 |
| K (2.4 μm) | 52.2 | 55.1 | 59.5 | 63.4 | 59.5 | 57.7 | 63.2 | 56.4 | 45.3 |

| DI<30 | |
|---|---|
| 30≤DI<40 | |
| 40≤DI<50 | |
| 50≤DI<60 | |
| 60≤DI<70 | |
| 70≤DI | |

| X | 1 | | | | 2 | | | | 4 | | | | 6 | | | |
|---|---|---|---|---|---|---|---|---|---|---|---|---|---|---|---|---|
| Y | 1 | 2 | 4 | 6 | 1 | 2 | 4 | 6 | 1 | 2 | 4 | 6 | 1 | 2 | 4 | 6 |

0.6 μm

| | 1 | 2 | 4 | 6 | 1 | 2 | 4 | 6 | 1 | 2 | 4 | 6 | 1 | 2 | 4 | 6 | |
|---|---|---|---|---|---|---|---|---|---|---|---|---|---|---|---|---|---|
| A | 33.8 | 31.6 | 25.7 | 30.0 | 50.4 | 47.0 | 34.0 | 33.0 | 56.5 | 43.4 | 43.3 | 27.2 | 43.9 | 49.3 | 37.0 | 35.3 | |
| C | 37.1 | 39.2 | 32.8 | 26.5 | 42.3 | 44.8 | 31.3 | 35.6 | 42.6 | 48.4 | 37.6 | 38.1 | 44.4 | 52.2 | 46.2 | 28.3 | |
| E | 37.3 | 37.9 | 30.9 | 25.9 | 46.6 | 44.1 | 30.0 | 33.3 | 59.3 | 46.1 | 42.5 | 34.8 | 53.0 | 47.0 | 44.2 | 39.3 | |
| I | 34.1 | 35.3 | 34.3 | 25.5 | 48.4 | 45.8 | 42.7 | 38.8 | 52.2 | 50.7 | 47.3 | 23.5 | 40.8 | 45.6 | 38.0 | 28.9 | |
| B | 35.2 | 32.0 | 32.5 | 25.2 | 46.3 | 43.7 | 29.0 | 26.1 | 44.0 | 49.7 | 38.1 | 32.6 | 50.6 | 42.8 | 38.1 | 43.8 | |
| D | 35.6 | 32.5 | 40.5 | 28.1 | 41.3 | 39.8 | 36.1 | 30.5 | 52.0 | 49.5 | 52.7 | 39.7 | 59.9 | 49.6 | 46.3 | 42.2 | |
| G | 27.5 | 30.8 | 29.5 | 30.2 | 44.8 | 43.0 | 35.7 | 44.3 | 54.1 | 49.1 | 34.5 | 31.1 | 54.2 | 44.3 | 30.9 | 27.3 | |
| J | 38.0 | 43.6 | 39.8 | 39.4 | 56.4 | 61.0 | 36.5 | 33.9 | 53.9 | 32.9 | 34.8 | 36.4 | 54.3 | 51.1 | 45.5 | 40.4 | |
| F | 39.5 | 31.8 | 32.1 | 33.6 | 35.8 | 48.8 | 34.4 | 32.9 | 50.1 | 51.7 | 41.3 | 39.2 | 52.6 | 53.4 | 51.3 | 39.7 | NS |
| H | 26.5 | 32.2 | 30.1 | 25.8 | 43.7 | 49.8 | 41.5 | 20.9 | 39.6 | 62.3 | 41.5 | 33.8 | 44.8 | 46.3 | 37.9 | 36.0 | 23.0 |

1.6 μm

| | | | | | | | | | | | | | | | | | |
|---|---|---|---|---|---|---|---|---|---|---|---|---|---|---|---|---|---|
| A | 30.0 | 29.2 | 25.7 | 29.8 | 42.1 | 39.6 | 28.7 | 28.6 | 42.4 | 37.2 | 33.4 | 23.7 | 41.4 | 32.3 | 27.2 | 27.0 | |
| C | 30.9 | 26.7 | 29.9 | 22.0 | 38.4 | 29.6 | 31.7 | 28.3 | 40.9 | 36.9 | 22.6 | 27.8 | 34.4 | 34.9 | 28.3 | 27.5 | |
| E | 37.6 | 31.9 | 29.4 | 20.7 | 34.4 | 25.0 | 21.6 | 21.6 | 31.8 | 24.2 | 23.6 | 29.8 | 44.1 | 43.4 | 36.0 | 32.7 | |
| I | 30.6 | 28.7 | 23.8 | 28.2 | 31.9 | 23.7 | 23.9 | 22.4 | 28.7 | 28.6 | 29.9 | 21.9 | 36.0 | 34.7 | 35.0 | 23.5 | |
| B | 25.7 | 24.9 | 24.4 | 27.0 | 41.4 | 32.1 | 25.5 | 25.1 | 35.4 | 36.0 | 28.4 | 26.4 | 39.9 | 28.8 | 32.0 | 35.1 | |
| D | 26.2 | 23.2 | 26.7 | 30.1 | 41.5 | 27.5 | 23.1 | 19.1 | 32.5 | 28.8 | 28.9 | 27.1 | 37.9 | 32.7 | 26.6 | 27.4 | |
| G | 22.7 | 21.3 | 18.0 | 19.2 | 36.9 | 26.2 | 29.7 | 34.9 | 39.5 | 36.3 | 36.1 | 26.1 | 37.4 | 35.5 | 28.1 | 28.8 | |
| J | 23.2 | 24.3 | 19.6 | 22.5 | 31.3 | 29.0 | 27.2 | 25.9 | 41.5 | 29.4 | 29.4 | 36.0 | 37.5 | 41.0 | 39.0 | 28.6 | |
| F | 27.4 | 21.2 | 23.7 | 21.4 | 35.0 | 28.7 | 25.0 | 24.6 | 39.2 | 39.6 | 35.6 | 35.4 | 32.3 | 30.4 | 29.9 | 29.5 | NS |
| H | 21.9 | 25.6 | 27.5 | 32.6 | 49.6 | 30 | 23.9 | 28.4 | 38.5 | 29.4 | 22.4 | 27.0 | 33.6 | 35.4 | 32.1 | 32.3 | 15.5 |

2.4 μm

| | | | | | | | | | | | | | | | | | |
|---|---|---|---|---|---|---|---|---|---|---|---|---|---|---|---|---|---|
| A | 25.7 | 20.4 | 24.6 | 23.4 | 29.2 | 27.7 | 24.8 | 28.4 | 28.7 | 24.8 | 33.6 | 28.5 | 32.0 | 33.0 | 25.1 | 25.4 | |
| C | 27.3 | 26.2 | 23.5 | 24.1 | 26.3 | 27.3 | 33.1 | 32.6 | 36.8 | 26.2 | 23.9 | 24.2 | 35.5 | 33.5 | 26.2 | 31.7 | |
| E | 36.5 | 29.7 | 23.3 | 28.2 | 25.3 | 23.9 | 24.3 | 30.0 | 34.6 | 25.2 | 24.1 | 29.9 | 42.1 | 31.8 | 33.3 | 30.2 | |
| I | 40.2 | 31.1 | 27.0 | 24.0 | 28.9 | 25.7 | 25.8 | 22.7 | 37.2 | 35.4 | 33.5 | 32.1 | 38.3 | 38.8 | 36.0 | 20.5 | |
| B | 20.1 | 22.5 | 19.4 | 25.2 | 30.6 | 27.4 | 24.1 | 24.2 | 29.4 | 34.3 | 28.0 | 33.1 | 31.5 | 20.7 | 23.4 | 22.5 | |
| D | 25.6 | 21.8 | 29.6 | 37.1 | 35.9 | 26.9 | 27.1 | 23.0 | 35.2 | 25.9 | 24.3 | 27.9 | 35.4 | 27.7 | 25.6 | 26.7 | |
| G | 24.4 | 19.5 | 17.5 | 29.8 | 36.2 | 32.4 | 37.4 | 37.4 | 38.1 | 30.2 | 22.8 | 19.9 | 33.5 | 27.0 | 28.0 | 22.9 | |
| J | 24.6 | 25.6 | 28.2 | 29.1 | 38.2 | 26.3 | 25.9 | 33.1 | 36.3 | 32.5 | 25.7 | 33.1 | 35.5 | 37.6 | 35.6 | 32.1 | |
| F | 28.7 | 20.4 | 21.1 | 21.8 | 35.6 | 28.3 | 23.8 | 29.6 | 46.6 | 37.9 | 33.3 | 28.9 | 37.6 | 28.3 | 26.4 | 24.7 | NS |
| H | 28.9 | 35. | 27.5 | 32.4 | 42.0 | 31.7 | 23.8 | 20.1 | 40.1 | 31.2 | 28.5 | 35.5 | 44.4 | 50.3 | 46.1 | 34.1 | 17.8 |

| T | 1 | 2 | 3 | 4 | 5 | 6 | 7 | 8 | NS |
|---|---|---|---|---|---|---|---|---|---|
| K (0.6 μm) | 50.1 | 61.9 | 54.7 | 56.8 | 54.0 | 51.5 | 47.6 | 37.1 | 23.0 |
| K (1.6 μm) | 41.8 | 43.6 | 43.0 | 41.8 | 44.5 | 44.5 | 37.5 | 38.5 | 15.5 |
| K (2.4 μm) | 41.5 | 44.7 | 43.8 | 41.4 | 40.6 | 40.0 | 37.8 | 33.0 | 17.8 |

| DI≤20 | |
|---|---|
| 20≤DI<30 | |
| 30≤DI<40 | |
| 40≤DI<50 | |
| 50≤DI | |

*Fig. 20b*

Alizarin red: Upper three rows; Serie A to J (2,3 and 15,16) Last row; K 1-8 and control surfaces a.
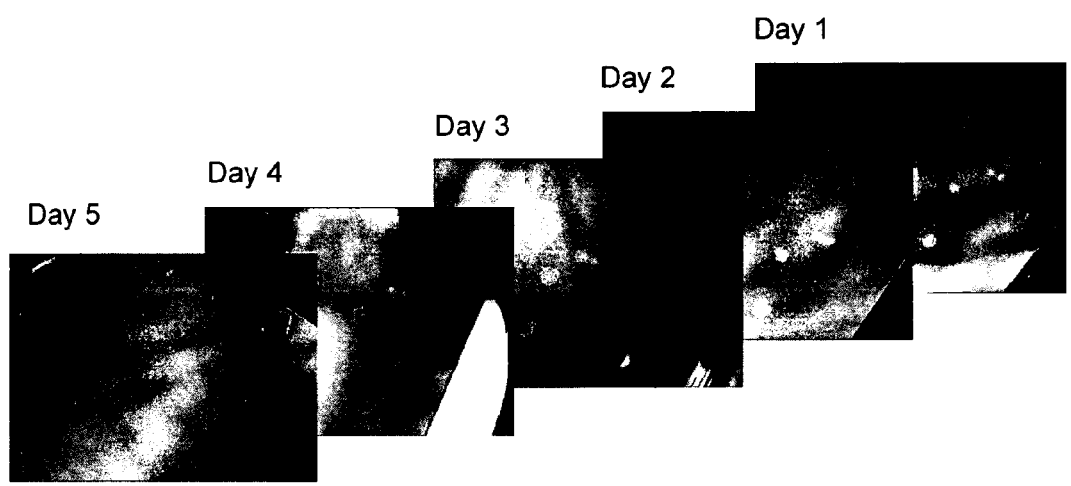
b.
| Day 1 | Day 2 | Day 3 | Day 4 | Day 5 |
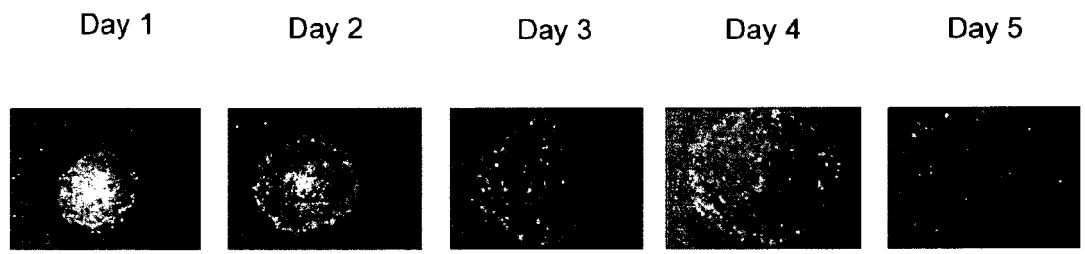
*Fig. 30* a.
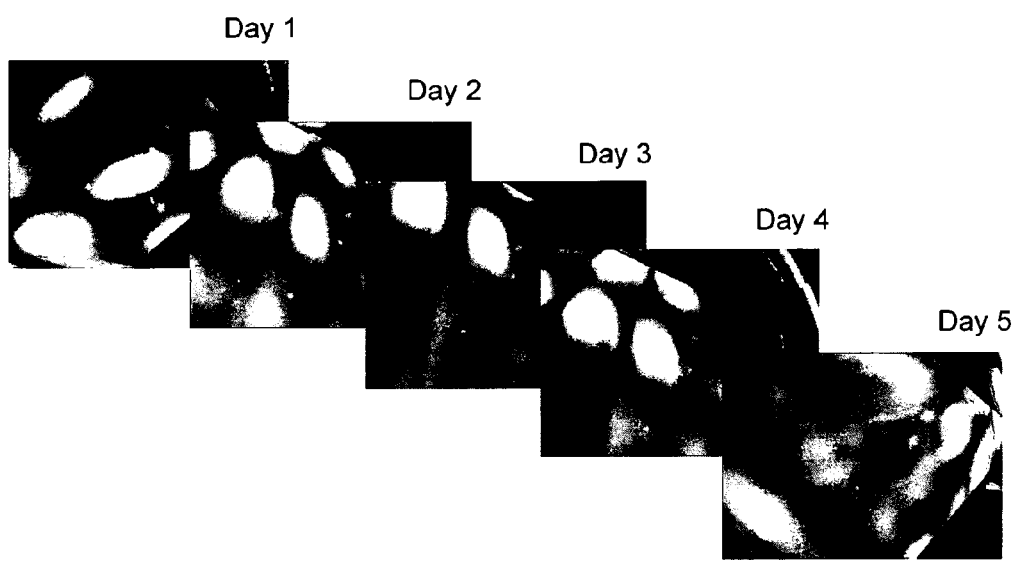
b.
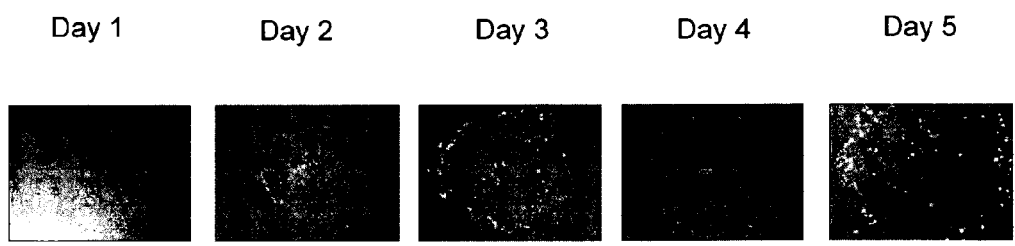
Fig. 31

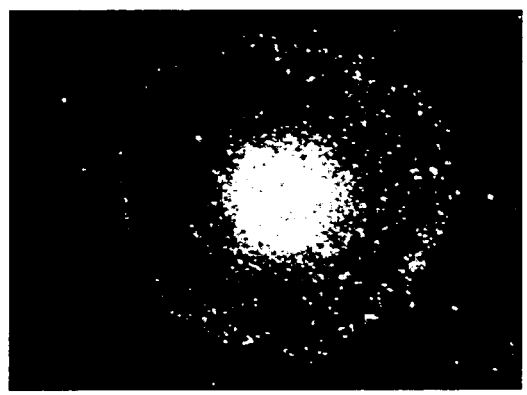
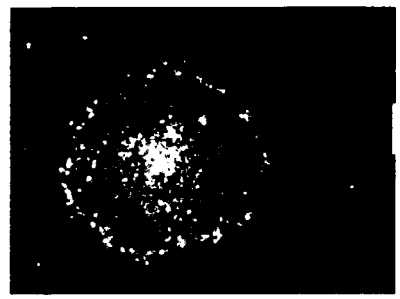
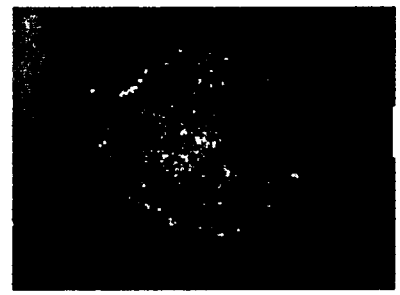
Fig. 32

BIOCOMPATIBLE MATERIALS FOR MAMMALIAN STEM CELL GROWTH AND DIFFERENTIATION

This application is a National Stage Application of PCT/EP2009/056443, filed 27 May 2009, which claims benefit of Serial No. PA200800726, filed 27 May 2008 in Denmark and Serial No. PA200800730, filed 27 May 2008 in Denmakr and which applications are incorporated herein by reference. To the extent appropriate, a claim of priority is made to each of the above disclosed applications.

TECHNICAL FIELD

The present invention provides biocompatible materials having a surface structure and composition that affects the cellular function and growth of embryonic stem cells. In a first aspect the present invention provides a biocompatible material having a composition and surface structure that either serves to promote the growth of undifferentiated pluripotent stem cells or serves to promote the uniform differentiated growth of stem cells. In second aspect the present invention provides a biocompatible material having a surface structure and composition that affects a cellular function, in particular cellular functions related to gene induction, cell differentiation and the formation of bone tissue in vivo and ex-vivo.

BACKGROUND OF THE INVENTION

With regards to the first aspect of the invention, the promotion of selected cellular functions is an important task in a variety of applications, such as the production of undifferentiated mammalian embryonic stem cells and/or their uniform differentiated growth. In particular, the therapeutic uses of mammalian embryonic stem [ES] cells has attracted considerable attention, and there has evolved an increasing need for producing undifferentiated mammalian ES cells as well as methods to guide and control their differentiation. Consequently, suitable microenvironments facilitating/promoting these processes are desirable. Biocompatible materials, on which ES cells can attach, grow, and/or differentiate and/or further perform diverse biological functions, are thus needed for a variety of therapeutic purposes. Medical conditions whose treatment might benefit from such materials include degenerative disorders, cancer and trauma of the musculoskeletal apparatus, each of which constitutes an increasing problem in public health.

There are three major demands on ES cell culturing protocols. Firstly, during ES cell culturing, the cells have to receive the proper stimuli from soluble factors in the medium and from the growth support to maintain pluripotency. Secondly, chromosomal integrity should be maintained. Thirdly, in order to facilitate the use of mammalian ES cells for medical purposes it is essential that the cells at no point come into contact with biological materials derived from another species, since xeno-contamination is most likely to cause immunogenic problems upon transplantation into a patient. Current culturing protocols generally depend on the use of biological material of animal origin, where ES cells are grown on a layer of feeder cells and serum. Feeder- and serum-free culture conditions have been described for murine ES cells, for example using gelatin-coated dishes combined with Leukemia Inhibitory Factor (LIF)-supplemented media, but these culture systems are expensive and do not always give rise to ES cells suitable for all forms of therapy.

Furthermore, future medical treatments aim to employ differentiated ES cells for implantation into a patient. For this purpose it is essential to ensure uniform differentiation in all ES cells, since the presence of undifferentiated cells in the implant can give rise to teratomas in the patient, which remains a problem for current differentiation protocols.

In conclusion there is a great need to develop xeno-free ES cell culturing conditions, both conditions in which the cells maintain pluripotency and chromosomal integrity and conditions in which the cells differentiate in a uniform and controlled manner.

With regards to the second aspect of the invention, the promotion of selected cellular functions is an important task in a variety of applications, such as the development of suitable implants. Biocompatible materials, on which living cells can attach, grow, and/or differentiate and/or further perform diverse biological functions, are desirable for a variety of therapeutic purposes.

Degenerative disorders, cancer and trauma of the musculoskeletal apparatus constitute an increasing problem in public health. Spinal disorders alone affect 30 percent of the adult population, and 40 percent of those older than 65 years have symptoms of osteoarthritis. More than 1.3 million joint alloplasties are performed annually worldwide to treat debilitating end-stage arthritis. Since there are no accepted therapies to prevent osteoarthritis, it is anticipated that the number of arthroplasties performed will rise dramatically over the next several decades, due to the aging of the western population. At the present time, more than 25 percent of all health care expenditures in Europe and USA are related to musculoskeletal conditions, and the budgets to treat such disorders in the USA (254 Billion USD) are for instance double the resources used for research and teaching in total.

The main surgical treatments of these disorders rely on the use of metallic medical implants in conjunction with bone or bone substitutes. The implants must be successfully incorporated in the bone tissue in order to obtain good clinical results. Major advances and results have been achieved in this area during the last decades, but implant loosening over time continues to be a significant problem for successful long-term joint replacements. The current implant surfaces, alone, are not able to bridge larger bone defects and maintain long-term stability. The use of bone grafts taken from the patients themselves to solve these problems is followed by a high donor site morbidity of 15-30 percent. As many as 20% of the patients undergoing hip replacement develop bone loss around the prosthesis within 10 to 15 years of the initial surgery, and in spinal fusion surgery 20-30 percent of the patients obtain poor fusion. Furthermore, as the near-future patient population will include a significant number of younger patients, the problem concerning long-term aseptic implant loosening is predicted to increase dramatically.

Improvement of implant behavior in bone tissue will therefore have a tremendous impact, both in terms of quality of life and economy. The WHO has recognized this by appointing the years 2000-2010 as the "Bone and Joint Decade" (bone-jointdecade.org/), an initiative also approved by the Danish Ministry of Health.

The biocompatibility/biointegration of an implant in the body is extremely complicated, involving processes traditionally belonging to medical science, surface science, materials science, and molecular biotechnology. When an implant is placed in tissue, a race for the surface starts immediately. Within a few milliseconds after the implant is inserted into the body, a biolayer consisting of water, proteins and other biomolecules from the physiological liquid is formed on the implant surface. Subsequently, cells from the surrounding tissue migrate to the area around the implant due to stimulation by cytokines and growth factors in the biolayer. The interaction between an implant surface and the cells is thus mediated through this biolayer. The properties of the implant surface strongly influence the properties of the layer and this influence needs to be understood and controlled in order to optimize biocompatibility. Of equal importance are the properties of the cells, e.g. their ability to communicate through the extracellular matrix by signal molecules. During bone healing, numerous bioactive signal molecules control bone formation and some proteins are found capable of stimulating bone healing to implants. All these mechanisms contribute to the response of the tissue to the implant and influence whether the implant is successfully anchored with sufficient mechanical strength in the bone of the patient or whether an inflammatory reaction against the implant occurs, which finally results in aseptic loosening and operative failure.

Biocompatible materials, on which bone tissue cells, can attach, and/or grow, and further perform diverse biological functions, are required for therapeutic purposes, in particular in surgical treatments involving the introduction of implants, such as prostheses and bone substitutes. Achieving a successful outcome of such treatment presents a formidable challenge, since an implant needs to allow tissue regeneration at the implant site, while avoiding becoming a target for the body's own powerful rejection mechanisms. The clinical success of an implant depends on the cellular behavior in the immediate vicinity of the interface between an implant and the host tissue. A key element in the progress in this field thus relies on the identification and use of a biocompatible material in the fabrication of these implants.

Bone tissue comprises a number of cell types including osteoprogenitor cells. Marrow stromal cells (MSCs) are pluripotent stem cells that give rise to both osteoprogenitor cells and other cell types. Osteoprogenitor cells can differentiate and form osteoblasts, particularly in response to bone regeneration. Bone modeling proteins (BMP and other growth hormones), produced by the marrow stromal cells, serve to both recruit osteoprogenitor cells and stimulate their maturation into osteoblasts. Osteoblasts secrete e.g. TGF-beta BMP's, other hormones and growth factors etc., which act both as a chemotactic attractant for osteoprogenitor cells, and stimulate the maturation of osteoblasts and induce the formation of bone matrix. Osteoblasts synthesize and secrete organic bone matrix (like collagen fibers, proteoglycans, osteocalcin, osteonectin and osteopontin) and hence osteoblasts play a key role in the deposition of mineralized bone matrix.

During the mineralization of bone, osteoblasts express alkaline phosphatase, together with a number of cytokines and growth hormones.

In the ongoing development of materials with improved biocompatibility there remains a need to identify materials whose structure is compatible with implant surgery and inductive for bone regeneration.

Furthermore, during recent years, therapeutic uses of embryonic stem cells has attracted considerable attention, and there has evolved an increasing need for the guided, controlled differentiation of embryonic stem cells. Consequently, suitable microenvironments facilitating/promoting these processes are desirable.

SUMMARY OF THE INVENTION

The first aspect of the invention is based on the recognition that an individual stem cell in the body or in a cell culture sees its surrounding tissue or tissue culture surface architecture at the level of micro- and nano-structures, where the above needs are addressed by providing a biocompatible material or structure with defined surface topography of micro scale features that may be employed in the construction of cell or tissue culture surfaces and/or devices for use in surgical/therapeutic treatment.

Examples of such stem cells are embryonic stem cells. The term stem cell is intended to refer to any kind of cell that is capable of undifferentiated cell growth to produce pluripotent stem cells, as well as differentiated cell growth. The term pluripotent stem cell encompasses a stem cell of mammalian origin, for example rodent or human stem cells. In particular the invention provides pluripotent mammalian embryonic stem cells and encompasses pluripotent embryonic stem cells capable of germline transmission.

The manufacture of a structure having the desired surface topography (that may be entirely artificial or may mimic a surface architecture observed in nature) requires techniques capable of defining features that have micrometer scale or nanometer scale dimensions. The present invention exploits the tools and techniques presently developed within micro- and nano-technology, which allow the design and construction of structures whose surface architecture may have a lateral feature size on a micro- or nano-meter scale. This feature size can be achieved e.g. by colloidal lithography of ferritin followed by removal of the organic phase leaving behind ion dots. In particular, the use of e-beam lithography and photolithography allows the manufacture of a surface topography which is precisely defined and which can be precisely reproduced in relevant applications.

In particular, regular patterns of spaced-apart protrusions that extend out of the surface have been found to be particularly efficient for promoting the growth of undifferentiated stem cells as well as their uniform differentiated growth. The sizes of the protrusions and the sizes of the gaps between protrusions have been found to be relevant parameters.

Accordingly, in a first aspect, the invention relates to the use of a cell or tissue culture container to promote growth of one or more undifferentiated pluripotent mammalian embryonic stem cells, the one or more cells being capable of germline transmission, the container having a surface for exposure to a culture during use, where at least a part of the surface is defined by a biocompatible material, wherein at least a part of an exposed face of the biocompatible material has a nano- and/or micrometer scale topographical structure comprising a plurality of protrusions arranged on grid points of a regular two-dimensional grid, characterized in that the cross-sectional dimensions of the protrusions occupy an area equal to or less than 25% of the total area of the structure, said area being measured in the plane of the exposed face of the structure, and wherein the density of protrusions is equal to or greater than 1 protrusion per 65 $\mu m^2$, and wherein each of the protrusions of said topographical structure has a vertical height/depth dimension equal to or greater than 1.6 $\mu m$, or alternatively equal to or greater than 3.0 $\mu m$; preferably between 2.0 $\mu m$-3.0 $\mu m$, more preferably 2.4 $\mu m$.

The protrusions may have a cross section and a minimum cross-sectional diameter of between 0.1 $\mu m$ and 4.0 $\mu m$, or between 0.5 $\mu m$ and 1.5 $\mu m$, and where the lateral dimension of the gap between any protrusion and its nearest neighbor (d;Y) may be between about 0.5 $\mu m$-8.0 $\mu m$, or between about 1 $\mu m$-6 $\mu m$, or between about 2 $\mu m$-6 $\mu m$, or between about 1 $\mu m$-4 $\mu m$. The minimum distance between adjacent grid points along at least one dimension is generally smaller than 8.0 $\mu m$, or between 0.5 $\mu m$ and 6.0 $\mu m$.

The protrusions may have the same cross-sectional geometrical shape or at least two different cross-sectional geometrical shapes, which may have different cross-sectional areas. The lateral cross-section of the protrusions may have a shape defined by circumference and/or geometry chosen from among the shapes: circular, concave, convex, round, star, square, rectangular, hexagonal and polygonal or a combination thereof. In an embodiment the protrusions of different cross sectional geometry are arranged on the regular two-dimensional grid in an alternating pattern.

At least part of the surface of the container may be coated with a material chosen from among tantalum, titanium, platinum or an oxide thereof. At least a part of said surface may comprise a polymer chosen from among polystyrene, polycaprolactone polylactic acid, poly(lactic-co-glycolic acid, chitosan or a combination thereof. The surface may further comprise a compound selected from the group consisting of: polypeptide, carbohydrate, lipid, growth hormone, antibody, antigen, glycoprotein, lipoprotein, DNA, RNA, polysaccharide, lipid, organic compound, and inorganic compound, where the compound can be adsorbed or chemically linked to the exposed surface of the container. Suitable growth hormones include BMP, EGF-like, TGF-beta, IGF and LIF.

The cell or tissue culture container may further be chemically functionalized by e.g. nanocrystalline diamond, plasma polymerization, oxygen plasma, or nitrogen plasma.

The invention further provides a stamp or mask for the production of a cell or tissue culture container of the invention, the container being at least partially produced from a biocompatible material, and the stamp being adapted to imprint or impart a topographical surface structure into a surface of the biocompatible material.

The invention further provides a cell or tissue culture container for promoting growth of undifferentiated pluripotent mammalian embryonic stem cells, having the features as set out above, where each of the protrusions of said topographical structure has a vertical height/depth dimension of about 2.4 µm.

In another aspect, the invention provides a method of promoting growth of one or more undifferentiated pluripotent mammalian embryonic stem cells, the one or more cells being capable of germline transmission, the method comprising bringing the cells into contact with a cell or tissue culture container having a surface for exposure to the stem cells, where at least a part of the surface is defined by a biocompatible material, wherein at least a part of an exposed face of the biocompatible material has a nano- and/or micrometer scale topographical structure comprising a plurality of protrusions arranged on grid points of a regular two-dimensional grid, where the structure is selected to promote growth of undifferentiated mammalian embryonic stem cells, characterized in that the cross-sectional dimensions of the protrusions occupy an area equal to or less than 25% of the total area of the structure, said area being measured in the plane of the exposed face of the structure, and wherein the density of protrusions is equal to or greater than 1 protrusions per 65 µm$^2$, and wherein each of the protrusions of said topographical structure has a vertical height/depth dimension that is either: equal to or greater than 1.6 µm, equal to or greater than 3.0 µm, or between 2.0 µm-3.0 µm, or about 2.4 µm.

According to this aspect of the invention, the protrusions may have a cross section and a minimum cross-sectional diameter of between 0.1 µm and 4.0 µm, or between 0.5 µm and 1.5 µm; and the lateral dimension of the gap between any protrusion and its nearest neighbor (d;Y) may be between about 0.5 µm-8.0 µm or between about 1 µm-4 µm. The minimum distance between adjacent grid points along at least one dimension may be smaller than 8.0 µm, or otherwise between 0.5 µm and 6.0 µm.

Furthermore, the structure may include protrusions of at least two different cross-sectional geometrical shapes defined by circumference and/or geometry selected from one the shapes: circular, round, star, square, rectangular, hexagonal and polygonal or a combination thereof, the shapes having different cross-sectional area. The protrusions of different cross sectional geometry may bee arranged on the regular two-dimensional grid in an alternating pattern.

Furthermore, at least a part of said surface may be tantalum-coated and/or titanium-coated, and at least a part of said surface may consist of a polymer including polystyrene, polycaprolactone polylactic acid, or chitosan. Other compounds on the surface may include one or more of a polypeptide, carbohydrate, lipid, growth hormone, antibody, antigen, glycoprotein, lipoprotein, DNA, RNA, polysaccharide, lipid, organic compound, and inorganic compound, wherein said compound is adsorbed or chemically linked, immobilized or complexed with the surface layer of the container. Suitable growth hormones include BMP, EGF-like, TGF-beta, IGF and Leukaemia inhibitory factor, or a combination thereof.

Furthermore the cell or tissue culture container may be chemically functionalized by e.g. nanocrystalline diamond, plasma polymerization, oxygen plasma, or nitrogen plasma.

In another aspect, the invention relates to the use of a cell or tissue culture container to promote uniform differentiated growth of mammalian embryonic stem cells and thereby facilitate the production of a population of differentiated cells wherein the number of undifferentiated cells is substantially reduced, such that the use of the differentiated cells in therapy (e.g. an implant) carries a reduced risk that the cells can give rise to teratomas in the patient, when compared to current differentiation protocols. Accordingly, the invention provides a container, the container having a surface for exposure to a culture during use, where at least a part of the surface is defined by a biocompatible material, wherein at least a part of an exposed face of the biocompatible material has a nano- and/or micrometer scale topographical structure comprising a plurality of protrusions arranged on grid points of a regular two-dimensional grid, characterized in that the protrusions have a cross section and a cross-sectional diameter of between 1.0 µm-8.0 µm and wherein the lateral dimension of the maximum gap between any protrusion and its nearest neighbor (d;Y) is between 1.0 µm-2.0 µm, and wherein each of the protrusions of said topographical structure has a vertical height/depth dimension that is equal to or less than 1.0 µm, preferably between 0.6 µm-1.0 µm, more preferably about 0.6 µm. The use of a cell or tissue culture container on the invention allows the production of a population of differentiated cells wherein the number of undifferentiated cells is substantially reduced, such that the use of the so produced cells in an implant carries a reduced risk that the implanted cells give rise to teratomas in the patient, when compared to current cell differentiation protocols.

Further, the lateral cross-section of one or more projections may have a shape defined by circumference and/or geometry that is either circular, concave, convex, round, star, square, rectangular, hexagonal or polygonal.

Furthermore, the surface may include projections having a square lateral cross-section and projections having a rectangular lateral cross-section, where a first cross-sectional diameter of the projections is 1.0 µm, and a second cross-sectional diameter of the projections is between 1.0 µm-8.0 µm, or between 1.0 µm-6.0 µm, and wherein the vertical height/depth dimension of the projections is equal to or less than 1.0 µm, preferably between 0.6 µm-1.0 µm, more preferably about 0.6 µm.

Furthermore, at least a part of said surface may be tantalum-coated and/or titanium-coated, and at least a part of said surface may comprise a polymer chosen from among polystyrene, polycaprolactone polylactic acid, poly(lactic-co-glycolic acid, chitosan or a combination thereof. The surface may further comprise a compound selected from the group consisting of: polypeptide, carbohydrate, lipid, growth hormone, antibody, antigen, glycoprotein, lipoprotein, DNA, RNA, polysaccharide, lipid, organic compound, and inorganic compound, wherein said compound is adsorbed to the exposed surface of the container.

In another aspect, the invention relates a method for promoting uniform differentiated growth of mammalian embryonic cells, the method comprising bringing the cells into contact with a cell or tissue culture container having a surface for exposure to the stem cells, where at least a part of the surface is defined by a biocompatible material, wherein at least a part of an exposed face of the biocompatible material has a nano- and/or micrometer scale topographical structure comprising a plurality of protrusions arranged on grid points of a regular two-dimensional grid, characterized in that the protrusions have a cross section and a cross-sectional diameter of between 1.0 µm-8.0 µm and wherein the lateral dimension of the maximum gap between any protrusion and its nearest neighbor (d;Y) is between 1.0 µm-2.0 µm, and wherein the vertical height/depth dimension of each of the protrusions is equal to or less than 1.0 µm, preferably between 0.6 µm-1.0 µm, more preferably about 0.6 µm.

According to this aspect, the lateral cross-section of one or more projections may have a shape defined by circumference and/or geometry selected from one the shapes: circular, round, square, and rectangular.

Furthermore, the surface may include projections having a square lateral cross-section and projections having a rectangular lateral cross-section, wherein a first cross-sectional diameter of the projections is 1.0 µm, and a second cross-sectional diameter of the projections is between 1.0 µm-8.0 µm, or between 1.0 µm-6.0 µm, and wherein the vertical height/depth dimension of the projections is equal to or less than 1.0 µm, preferably between 0.6 µm-1.0 µm, more preferably about 0.6 µm Furthermore, at least a part of said surface may be tantalum-coated and/or titanium-coated, and at least a part of said surface may comprise a polymer chosen from among polystyrene, polycaprolactone polylactic acid, poly(lactic-co-glycolic acid, chitosan or a combination thereof. The surface may further comprise a compound selected from the group consisting of: polypeptide, carbohydrate, lipid, growth hormone, antibody, antigen, glycoprotein, lipoprotein, DNA, RNA, polysaccharide, lipid, organic compound, and inorganic compound, wherein said compound is adsorbed to the exposed surface of the container.

The second aspect of the invention is based on the recognition that an individual cell in the body or in a cell culture sees its surrounding tissue or tissue culture surface architecture at the level of micro- and nano-structures, the above needs are addressed by providing a biocompatible material or structure with defined surface topography of micro scale features that may be employed in the construction of cell or tissue culture surfaces and/or implants and devices for use in surgical/therapeutic treatment.

Examples of such cells are bone-forming cells. The term bone-forming cells is intended to refer to any kind of cell that is capable of forming bone, including naturally occurring cell types and/or modified cell types, e.g. modified by means of genetic technologies. Other examples include embryonic stem cells and neurons.

The manufacture of a structure having the desired surface topography (that may be entirely artificial or may mimic a surface architecture observed in nature) requires techniques capable of defining features that have micrometer scale or nanometer scale dimensions. In particular, it has turned out that when at least a part of a surface of such a biocompatible material is characterized by a micrometer scale topographical structure, a number of cell functions of at least one of a variety of different cell types are significantly improved. In particular, regular patterns of spaced-apart protrusions that extend out of the surface have been found to be particularly efficient for promoting the above-mentioned cell functions.

The present invention provides a medical implant for use in bone-tissue implantation, the medical implant comprising a surface, where at least a part of the surface is defined by a biocompatible material, wherein at least a part of a surface of the biocompatible material is characterized by a nano- and/or micro-meter scale topographical structure comprising a plurality of protrusions arranged on grid points of a regular two-dimensional grid, where the structure is capable of promoting bone formation by expression of osteopontin and osteocalcin in bone-forming cells, wherein the protrusions have a cross section with a minimum cross-sectional diameter 1.0 µm-2.0 µm, wherein the distance between adjacent grid points along at least one dimension is between 2.0 µm and 9.0 µm, wherein each of the protrusions of the topographical structure has a vertical height/depth dimension equal to or greater than 1.60 µm, preferably about 2.4 µm.

In a further aspect of the medical implant, the lateral dimension of the maximum gap between any protrusion and its nearest neighbor (d;Y) may be between about 1.0 µm-6.0 µm. Furthermore, the cross-sectional diameter of the cross section may be about 1 µm and the lateral dimension of the minimum gap between any protrusion and its nearest neighbor (d;Y) may be about 1.0 µm.

In a further aspect of the medical implant, the structure may include protrusions of at least two different cross-sectional geometrical shapes for example: circular, concave, convex, round, square, and rectangular, or a combination thereof; which may have different cross-sectional areas, where the protrusions of different cross sectional geometry may be arranged on the regular two-dimensional grid in an alternating pattern.

In a further aspect of the medical implant, the protrusions may be positioned on grid points of the two-dimensional regular grid such that only a subset of grid points are covered by protrusions. Furthermore, the protrusions may be arranged in parallel rows where the centre-to-centre distance between adjacent protrusions is different in adjacent rows. Furthermore, the center of the features of said periodic topographical structure may be placed on grid points of a 2-dimensional rectangular grid with grid constants a and b, and wherein: the grid is a square grid wherein the grid constant in each direction (a=b) is in an interval between 2-8 µm, or the grid is rectangular with a grid constant (a) in a first direction in an interval between 2-8 µm and with a grid constant (b) in a second direction in an interval between 1-4 µm.

In a further aspect of the medical implant, at least a part of the surface is tantalum-coated and/or titanium-coated or any oxide thereof; and/or at least a part of said surface consists of a biodegradable polymer as polylactic acid or poly(lactic-co-glycolic acid). Furthermore the surface may further comprise an adsorbed compound selected from the group consisting of: polypeptide, carbohydrate, lipid, growth hormone, antibody, antigen, glycoprotein, lipoprotein, DNA, RNA, polysaccharide, lipid, organic compound, and inorganic compound. Suitable growth hormones include BMP, EGF-like, TGF-beta, and IGF.

The medical implant of the invention may be a surgical implant, such as a dental implant, orthopedic implant, stent, heart valve for use in the treatment of a human or animal suffering from a condition, for example a dental condition, an orthopedic condition or a pulmonary cardiac condition.

In a further aspect, the invention provides a stamp or mask for the production of a medical device, the medical device being at least partially produced from a biocompatible material, the stamp being adapted to imprint or impart a topographical surface structure into a surface of said biocompatible material.

In a further aspect the invention is directed to the use of a cell or tissue culture container to promote gene expression in differentiated cells during cell culture, the container having a surface for exposure to a cell culture during use, where at least a part of the surface is defined by a biocompatible material, wherein at least a part of a surface of the biocompatible material is characterized by a nano- and/or micro-meter scale topographical structure comprising a plurality of protrusions arranged on grid points of a regular two-dimensional grid, wherein the protrusions have a cross section with a minimum cross-sectional diameter 1.0 µm-2.0 µm, wherein the distance between adjacent grid points along at least one dimension is between 2.0 µm and 9.0 µm, wherein each of the protrusions of the topographical structure has a vertical height/depth dimension equal to or greater than 1.60 µm, preferably about 2.4 µm.

In a further aspect, the invention provides a biocompatible coating for use in the manufacture of a medical implant, wherein the biocompatible coating comprises a biocompatible material as set out above.

In a further aspect, the invention provides a method of promoting bone formation by expression of osteopontin and osteocalcin in bone-forming cells, the method comprising bringing the cells into contact with a biocompatible material wherein at least a part of a surface of the biocompatible material is characterized by a nano- and/or micro-meter scale topographical structure comprising a plurality of protrusions arranged on grid points of a regular two-dimensional grid, wherein the protrusions have a cross section with a minimum cross-sectional diameter 1.0 µm-2.0 µm, wherein the distance between adjacent grid points along at least one dimension is between 2.0 µm and 8.0 µm, wherein each of the protrusions of the topographical structure has a vertical height/depth dimension equal to or greater than 1.60 µm, preferably about 2.4 µm.

BRIEF DESCRIPTION OF THE DRAWINGS

The invention will be explained more fully below in connection with embodiments and with reference to the drawings, in which:

FIG. 1 shows a top view of an example of a screening tool—a so-called BioSurface Structure Array (BSSA) wafer—for identifying topographical structures that facilitate/enhance cellular functions such as mineralization by bone-forming cells or growth/differentiation of stem cells, such as embryonic stem cells, adult stem cells, umbria cord stem cells or the growth of neurons.

FIG. 2 shows a cross sectional view of the screening tool of FIG. 1 along the line labeled A-B.

FIG. 3 shows a top view (FIG. 3a) and a cross-sectional view (FIG. 3b) of a topographical structure comprising alternating trenches of width X (in µm) and ridges of width Y (in µm).

FIG. 4 shows a top view (FIG. 4a) and a cross-sectional view (FIG. 4b) of a topographical structure comprising square holes and a predetermined pitch distance.

FIG. 5 shows a top view (FIG. 5a) and cross-sectional views (FIG. 5b,c) of a topographical structure comprising rectangular holes of dimension X (in µm)×Y (in µm) separated with ridges of width X µm.

FIG. 6 shows a top view (FIG. 6a) and a cross-sectional view (FIG. 6b) of a topographical structure comprising pillars of a predetermined dimension and a predetermined pitch distance.

FIG. 7 shows a top view of a topographical structure comprising alternating square holes and pillars.

FIG. 13 shows an evaluation of automated colony counting. Undifferentiated KH2 ES cell colonies were counted automatically (Auto) and manually (Man) for selected structures having three different structure heights (0.6, 1.6 and 2.4 µm). The values are triplicate average values. Automated counting was based on colony size. Manual counting was based on colony morphology and AP staining intensity.

FIG. 14 shows the number of undifferentiated CJ7 and KH2 ES cell colonies detectable by automated counting (average of 3 values) following 3 days cultivation on BSSA wafers. The data for the A to J structures are ordered by structure dimensions, X and Y. The K structures are represented in a separate table ordered by T value. Different shade scales were applied for the different structure heights: 0.6, 1.6 and 2.4 µm. NS: Non-Structured.

FIG. 19 shows a table setting out the germline potential of CJ7 cells following serial passaging on one of: biocompatible surface structures F1.2, or F4.1; gelatin-coated plates; or media comprising feeder cells.

FIG. 20 shows the Differentiation index (Differentiation index=Total DAPI area−Total ES cell colony area) of CJ7 and KH2 ES cell colonies based on automated measurements (average of 3 values) following 3 days cultivation on BSSA wafers. The data for the A to J structures are ordered by structure dimensions, X and Y. The K structures are represented in a separate table ordered by T value. The values obtained from the different structure heights (0.6 µm, 1.6 µm and 2.4 µm) are all represented by the different scales.

The fluorescence microscopy images show MC3T3 cells after being seeded on the BSSA wafer; grown for two weeks; and subsequently fixed and stained for OPN (green), OC (red) and DAPI (blue), and subsequently stained with Alizian red. Horizontal rows 1-10: images of the structures where (X,Y) =1,2 1,4 6,4 and 6,6 with an unstructured surface intersecting each structure starting with Series A (top row) to J (bottom row). Horizontal rows 11-14; images of K structures together with unstructured surface starting with K1, K2 above unstructured surface at the edge of the BSSA wafer ending with K7,K8 above unstructured surface (last row). Black field in DAPI channel row 9 is due to a mechanical failure in changing the filters in the automated picture acquisition program in the microscope.

Figure 27:
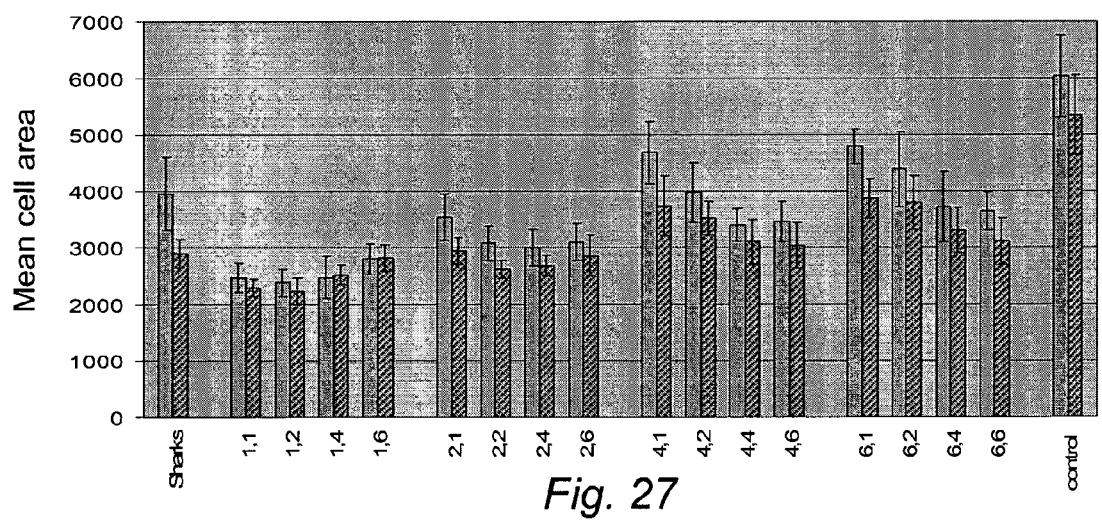

FIG. 27 shows the area of MC3T3 cells attached to BSSA wafers (as defined in FIG. 23). Quantification of mean cell area of MC3T3 cells after one day of attachment as measured by the area covered by the Actin/Vinculin overlay divided by the number of cells (DAPI staining). All structures with the same size (X) and gap (Y) between structures from series A to J were pooled. Solid columns and cross-hatched columns: Two independent experiments.

Figure 28:
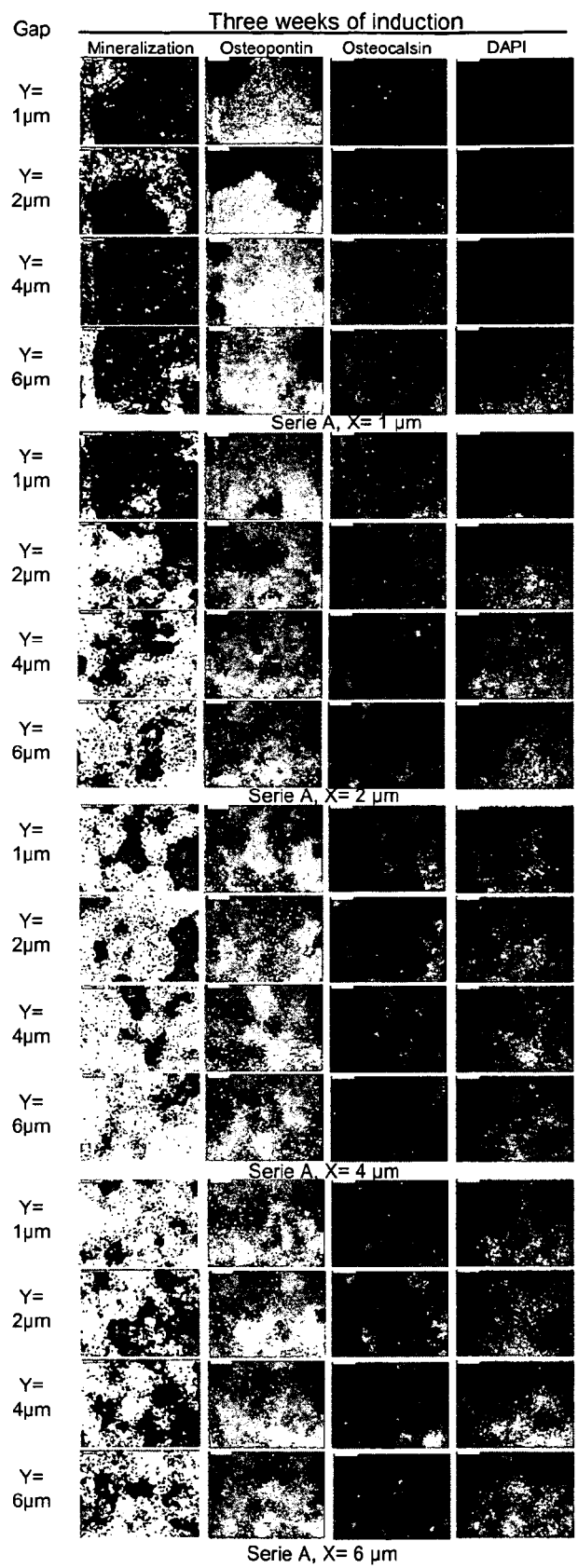

FIG. 28 shows the mineralization, expression of OPN, OC, and DAPI staining of MC3T3 cells after 3 weeks induction on BSSA wafers, having Series A surface structures having a vertical dimension of Z=2.4 µm, (as defined in FIG. 23).

The fluorescence microscopy images show MC3T3 after being seeded on a BSSA wafer; grown for three weeks; then fixed and stained for Osteopontin (OPN, green), Osteocalcin (OC, red) and DAPI (blue); and subsequently stained with Alizarin red (vertical panel row 1). Horizontal panel rows 1 to 4 have a feature size of X=1 µm and gaps (Y) between 1, 2, 4 and 6 µm respectively. Horizontal panel rows 5 to 8 has a feature size of X=2 µm and gaps (Y) between 1, 2, 4 and 6 µm respectively. Horizontal panel rows 9 to 12 has a feature size of X=4 µm and gaps (Y) between 1, 2, 4 and 6 µm respectively. Horizontal panel rows 13 to 16 has a feature size of X=6 µm and gaps (Y) between 1, 2, 4 and 6 µm respectively.

Figure 29:
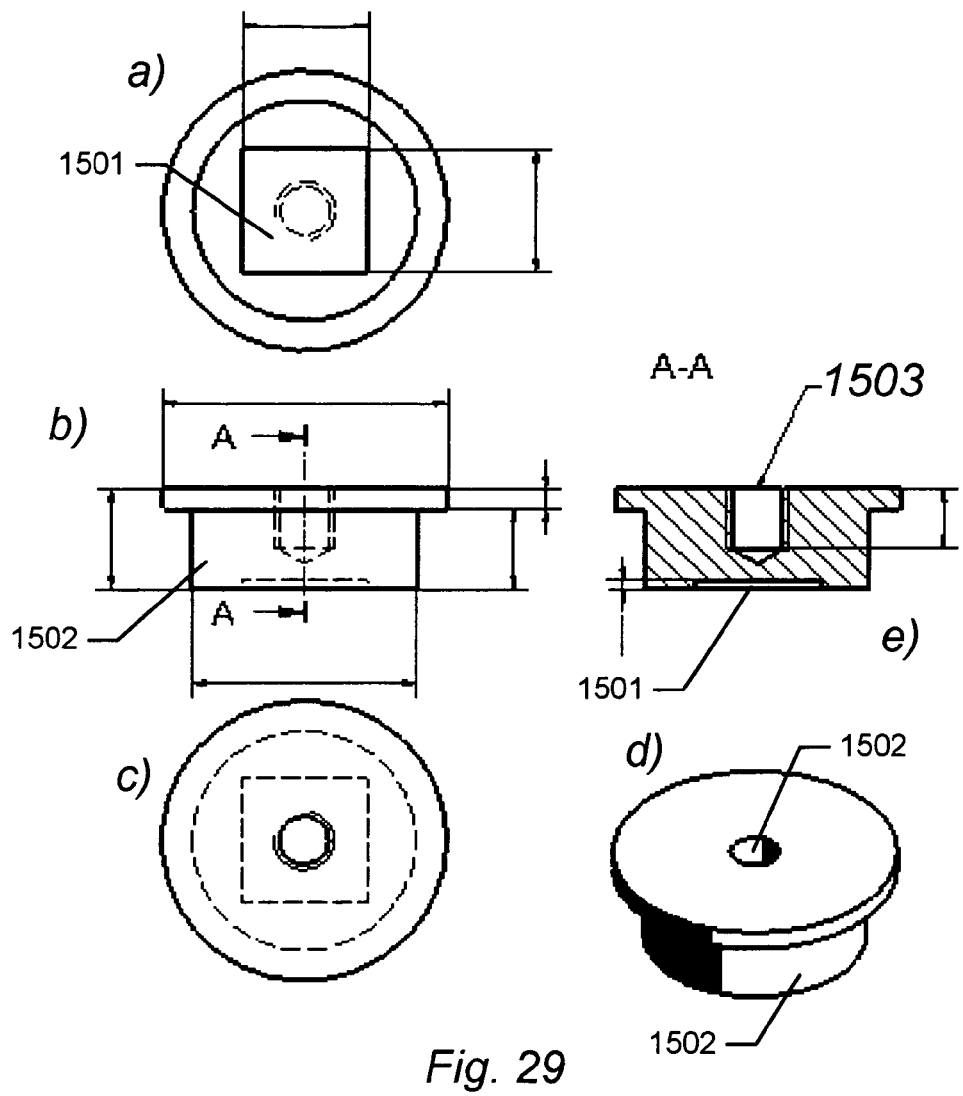

FIG. 29 shows a sample holder for use in a bone-forming assay in sheep.

FIG. 30 shows human embryonic stem cell (hESC) colony growth over time on the biocompatible surface F(1,4) having features with a height/depth of 2.4 µm. The cells were passaged on day 0 and the photographs were taken every day for 5 days. FIG. 30a shows an overview of all the colonies on the surface (0.8×). FIG. 30b shows a time course of morphological changes of one selected hESC colony (8×).

FIG. 31 shows human embryonic stem cell colony growth over time on surface F(1,2) having features with a height/depth of 2.4 µm. The cells were passaged on day 0 and the photographs were taken every day for 5 days. FIG. 31a shows an overview of all the colonies on the surface (0.8×). FIG. 31b shows time course of morphological changes of one selected hESC colony (8×).

FIG. 32 shows a comparison of human embryonic stem cell colonies grown on nano-surfaces to those grown on Geltrex™ matrix (Invitrogen), which is a soluble form of reduced growth factor (RGF) basement membrane extract.

Figure 33:
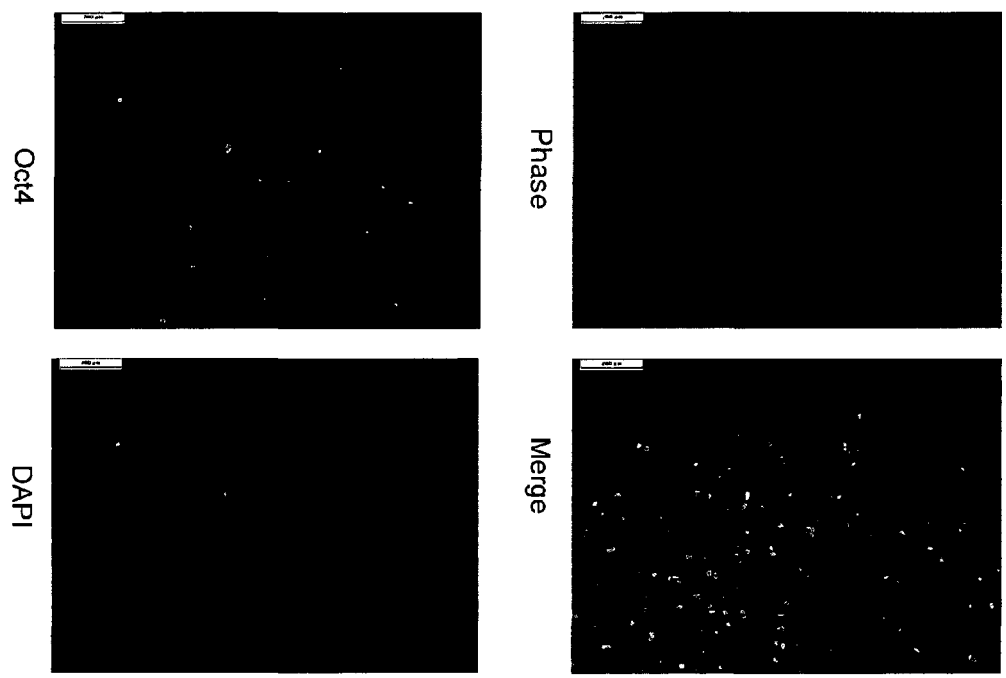

FIG. 33 shows immunofluorescence, DAPI and phase image of cells grown on the surface F(1,4) having features with a height/depth of 2.4 µm.

Figure 34:
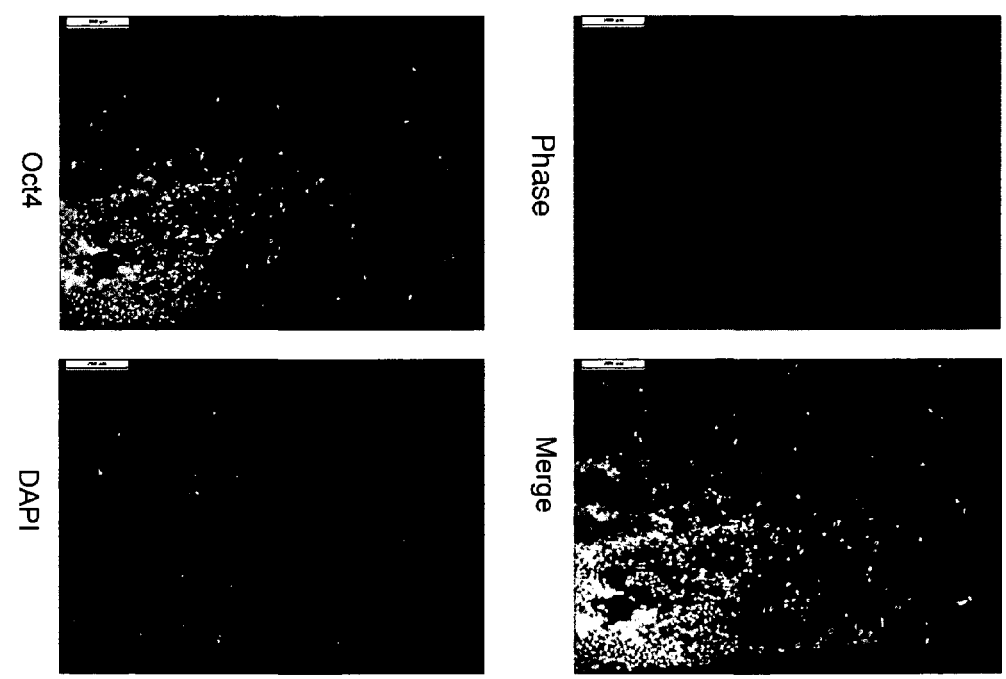

FIG. 34 shows immunofluorescence, DAPI and phase image of cells grown on the surface F(1,2) having features with a height/depth of 2.4 µm.

DETAILED DESCRIPTION OF THE INVENTION

The Invention According to a First Aspect

This aspect relates to the need to grow large quantities of pluripotent mammalian embryonic stem cells in an undifferentiated state and to subsequently induce the embryonic stem cells to differentiate into a desired cell type. Once differentiated into a specific cell type, these specific cell types may be used for many different applications such as drug screening, cell replacement therapy, diabetes, cartilage damage, etc.

The present invention is based on the recognition that cellular functions that direct growth, and/or differentiation are strongly influenced by the cell's microenvironment. Thus, it is thought that the growth of undifferentiated embryonic stem cells as well as their subsequent differentiation may depend on the provision of a suitable structure to which the cells can attach. In particular the invention recognizes that the 2- and 3-dimensional architecture, or topography, of surfaces in the microenvironment of a cell, is a critical factor for above processes. There are a myriad of different possible microenvironments. In one aspect, the present invention thus concerns the provision of a biocompatible material whose surface topography creates a specific microenvironment that promotes growth of pluripotent mammalian embryonic stem cells in an undifferentiated state. In a second aspect the invention provides a biocompatible material whose surface topography cellular growth and/or differentiation. As proteins and cells range in size from nano- to micrometer these are relevant length scales for the problem of providing a biocompatible material.

I. Method of Testing and Selecting a Biocompatible Material for the Growth of ES Cells and Promoting Differentiation.

The biocompatible material or structure of the invention may be identified by screening materials with different surface topography using a screening tool/assay that provides different candidate topographical structures.

An example of a screening tool suitable for the screening of topographical structures includes a so-called BioSurface Structure Array (BSSA) wafer. FIG. 1 shows a top view of an example of such a biosurface structure array wafer. The BSSA wafer 1 comprises 60 tester areas. A number of tester areas 2 are left "blank", i.e. they have not been processed to have a structured surface. Consequently, the surfaces of the tester areas 2 are substantially flat. Consequently a control experiment is inherently included in each parallel screening test with the BSSA screening tool. The remaining tester areas, designated S1, S2 . . . , S54, comprise respective structured surfaces as described herein. The tester areas are squares of dimension 10 mm×10 mm.

A wafer for use as a screening tool to identify structures that induces/enhances cellular functions such as growth and differentiation may be manufactured by a number of production techniques. Examples of procedures for its manufacture include one or more of the following techniques that are known as such in the art:

Photolithography methods: Photolithography is a process known as such in which geometric shapes/patterns are transferred from a photomask to the surface to be structured, e.g. the surface of a wafer. Photolithography equipment with minimum lateral feature sizes ranging from around 1 micrometer to below 100 nm is known as such. Photolithography processes are described in e.g. S.

M. Sze: Semiconductor Devices, Physics and Technology, 2nd Edition, John Wiley & Sons 2002, Chapter 12: Lithography and Etching; and in Plummer, Deal, Griffin: Silicon VLSI Technology, Fundamentals, Practice, and Modeling, Prentice Hall 2000, Chapter 5: Lithography.

E-beam lithography: In principle, E-beam lithography can be used to expose a photoresist in exactly the same way as the light is used in photolithography. E-beam lithography has a particularly high resolution up to around 5 nm.

Hot embossing: Hot embossing uses a master stamp to imprint micro- and nanometer scale structures on polymer substrates. The method allows the master stamp to produce many fully patterned substrates using a wide range of polymer materials. Hot embossing provides a low-cost, highly versatile manufacturing method that is well suited for the manufacture of BSSA for uses ranging from research and development applications to high-volume production. High aspect ratios with a very high degree of homogeneity may be achieved for micro- and nanometer scale structures on large-sized wafers, such as 8 inch or 12 inch wafers. Features sizes below 20 nm are possible. The master stamp may be produced by e.g. E-beam lithography techniques.

Other examples of production steps or processes that may be involved in the production of the biocompatible material or structure include nano imprint lithography, laser ablation, chemical etching, plasma spray coating, abrasive blasting, engraving, scratching, micro machining, or the like.

FIG. 2 shows a cross sectional view of the wafer of FIG. 1. FIG. 2a shows a cross section of the entire width of the wafer along the line labelled A-B. FIG. 2b shows an enlarged view of a portion of the surface of one of the tester areas. The wafer 1 has a layered structure including a patterned substrate layer 21, e.g. a silicon layer, and a surface layer 23. The surface of the wafer is patterned, e.g. by a photolithography process, to provide different patterns on the surfaces of the respective tester areas S1, S2, . . . , S54. The structures have a depth/height H. In a photolithography process the height H is controllable by the etching process. The patterned surface is covered by a thin layer of silicon dioxide 22, and/or a surface layer 23 of a different biocompatible material such as tantalum or any other metal, metal oxide, metal nitrides, metal carbides, diamond, diamond like carbon, semiconductor, semiconductor oxide/nitride, insulator, polymers, copolymers. Between the tester areas there is a "blank" border area with no structure, i.e. the border area has not been processed to have a structured surface. In this case the width of the blank border area is 0.3 mm. A blank border aids visual alignment and identification of the structures. The blank border further serves as a small control surface next to each tester square.

It is noted that the FIG. 2 is schematic and not drawn to scale. In particular, the vertical dimensions may be exaggerated to improve readability.

II. Chemical Composition of a Biocompatible Material of the Invention

Embodiments of a biocompatible material or structure may take a variety of forms, such as
- a medical implant or a biocompatible coating for use in the manufacture of a medical implant,
- a tissue culture dish/flask having a surface to be exposed to the cell culture, where the exposed surface with structures supporting the desired cellular function, e.g. growth of embryonic stem cells in an undifferentiated or differentiated state,
- a tissue culture surface or e.g. tissue culture plastic that has been modified to display these structures or blueprint of these structures on the surface. In this respect tissue culture plastic means any polymers that can be used to produce a surface that can be used for growth of cells in vitro in cell culture.

Embodiments of a biocompatible material or structure may comprise a substrate layer, and optionally, a surface layer.

Suitable base materials for the preparation of the biocompatible material or structure include any semiconductor (doped or not-doped), a single metal, a metaloxide, a metal nitride, an alloy, a ceramic, a polymer, a co-polymer, a composite, a drug delivery system, a polymer with bioactive molecules, other bioactive compounds or any combination thereof.

In embodiments of the invention, the surface layer comprises a material that is sufficiently biocompatible for growth of ES cells in vitro and/or following implantation in a patient. Examples of surface layers include a metallic surface deposit, e.g. tantalum, titanium, Ti—Al—V alloys, gold, chromium, metal oxides, semiconductor oxides, metal nitrides, semiconductor nitrides, polymers, biopolymers, or other alloys. Preferred surface compositions for implants include tantalum, titanium, platinum or an oxide thereof.

In an embodiment of the invention, at least a part of the surface layer comprises a polymer chosen from among polystyrene, polycaprolactone polylactic acid, poly(lactic-co-glycolic acid, chitosan or a combination thereof.

In an embodiment of the invention, the cell or tissue culture container is chemically functionalized by e.g. nanocrystalline diamond, plasma polymerization, oxygen plasma, or nitrogen plasma.

In some embodiments, the biocompatible material or structure comprises additional components such as one or more bioactive compound, which may be deposited or adsorbed on the exposed surface or surface layer of said material or structure. For example, said compound may be selected from the group consisting of an antibody, antigen, glycoprotein, lipoprotein, DNA, RNA, polysaccharide, lipid, growth hormone, organic compound, and inorganic compound. Preferably, one or more growth hormone selected from Bone Morphogenetic Protein [BMP], Epidermal Growth Factor [EGF], Transforming Growth Factor-beta [TGF-beta], Insulin-like Growth Factor IGF and Leukaemia Inhibitory Factor [LIF] is adsorbed or chemically linked, immobilized or complexed with the surface layer of the container.

III. Structural Properties of a Biocompatible Material of the Invention

All or part of the surface of the biocompatible material or structure (which may take a variety of forms as described above) comprises micrometer scale features in one or more dimensions within the plane defined by the surface of the material or structure. The terms micro scale and micrometer scale as used herein are intended to refer to a length scale in the range of between about 1 μm and about 1000 μm. The term nanometer scale as used herein is intended to refer to a length scale in the range of between about 1 nm and about 1000 nm, in particular between about 1 nm and about 100 nm.

In embodiments of the invention, the features are structural/topographical features such as protrusions extending out of the surface of the biocompatible material.

A micrometer scale feature may have a lateral dimension in at least one lateral direction, where said dimension is selected from one of the intervals: between about 1 μm and about 20 μm; between about 1-10 μm; between about 10-20 μm, between about 1 μm-2 μm, between about 2 μm-4 μm, between about 4 μm-6 μm, between about 6 μm-8 μm, between about 8 µm-10 µm; between about 10-12 µm; between about 12-14 µm; between about 14-16 µm; between about 16-18 µm; between about 18-20 µm. Preferably, in one embodiment of the invention, at least one lateral dimension is between 0.1 µm-4 µm. Hence, the shortest distance from any given point within the cross-sectional area of a feature to the edge of the cross-sectional area is equal to or less than 4 µm.

The lateral dimension is measured in a direction substantially parallel to the surface or at least substantially tangential to the surface.

The maximum distance, or gap, between any micrometer scale feature and its nearest neighbor can have a lateral dimension in at least one lateral direction where said dimension is selected from one of the intervals: between about 0.5 µm-1 µm, between about 1-2 µm, between about 2 µm-4 µm, between about 4 µm-6 µm, between about 6 µm-8 µm, between about 8 µm-10 µm, between about 10 µm-12 µm, between about 12 µm-14 µm, between about 14 µm-16 µm. Preferably, in embodiments of the invention the lateral dimension is between 0.5 µm-8 µm. The disposition of micrometer scale features at the surface of the biocompatible material is preferably periodic along one or more lateral direction, and may be described by a periodic function having a lateral pitch dimension selected from one of the intervals: between about 1 µm-2 µm, between about 2 µm-4 µm, between about 4 µm-6 µm, between about 6 µm-10 µm, between about 10 µm-16 µm, between about 16 µm-20 µm, between about 20 µm-24 µm. In one embodiment of the invention, the pitch dimension is less than 8.0 µm, more preferably between 0.5 µm-6.0 µm.

The periodic function of the micrometer scale features may have a smaller period along one direction and a larger period, e.g. by a factor of 2, 3, 10 or larger, in another direction. Any one micrometer scale feature at the surface of the biocompatible material may be defined as a period of the periodic structure. Hence, the lateral dimensions of a feature of a periodic structure may be defined as the period of the periodic shape/function, i.e. the length of the shortest interval over which the structure repeats its shape.

The depth/height of the micrometer scale features, i.e. their linear dimension in a direction projecting out of the surface of the biocompatible material may be on the nano- or micrometer scale, i.e. the structures may have heights/depths in the range 1 nm-10 µm, or in a range selected from the intervals: of between about 0.07 µm-0.6 µm, 0.6 µm-1.6 µm, of between about 1.6-3.0 µm, of between about 3 µm-10 µm. In one embodiment of the invention, structures (e.g. protrusions) have a vertical height/depth dimension that is either: equal to or greater than 1.6 µm, or equal to or greater than 3.0 µm, or preferably between 2.0 µm-3.0 µm, or about 2.4 µm. This embodiment is particular suitable for the promotion of undifferentiated growth of pluripotent stem cells. In another embodiment, all features (protrusions) have a vertical height/depth dimension that is equal to or less than 1.0 µm, preferably between 0.6 µm-1.0 µm, more preferably about 0.6 µm. This embodiment is particular suitable for the promotion of the differentiation of stem cells.

The lateral cross section of any one micrometer scale feature is preferably geometrical, such as square, rectangular, hexagonal, polygonal or star-shaped. The top and/or side surfaces of the feature are preferably substantially flat. The surfaces of the micrometer scale features can, however, also include features on the nanoscale to achieve a synergistic effect of the topography both on the micrometer and nanometer scale. This can be obtained by e.g. chemical etching (e.g. by NaOH or citric acid), ion etching, colloidal lithography (e.g. by polystyrene beads, bucky balls or proteins), grazing incidence Physical Vapour Deposition coating, CVD coating, or plasma spraying. The features at the surface of the biocompatible material may have the same or different shapes. Preferably the features at the surface of the biocompatible material are geometric (e.g. square, rectangular, hexagonal, star-shaped, or polygonal) in shape.

In general, a 2-dimensional periodic structure may be defined by a unit cell in the plane of the surface having a predetermined shape, such as square, rectangular, hexagonal etc., and a repeat unit defining the detailed structure (the base) in the unit cell, such as holes or protrusions, e.g. square pillars, polygonal pillars, circular pillars, etc. The positions defined by that unit cell define the repeat distances, while the repeat unit defines the predetermined shape and size. These unit cell positions may be defined by respective 2-dimensional vectors. The grid structure thus results from a translation of the unit cell along the two dimensions defined by the surface, in particular respective multiples of the unit cell dimensions. In one embodiment, the centre position of each feature may be defined by a vector $v=n_1 v_1 + n_2 v_2$, where $v_1$ and $v_2$ are linearly independent vectors in the surface and $n_1$ and $n_2$ are integers.

In some embodiments, the center of each feature is placed on a grid point of a 2-dimensional grid, e.g. a hexagonal, a rectangular or a square grid with predetermined grid constants (FIG. 8 A,B).

In some embodiments, all features cover all grid points of such a grid, while in other embodiments not all grid points of the underlying grid are covered.

For example, in some embodiments, in every other row of grid points, every other grid point may be covered by a feature. In yet other embodiments, in every second, third, fourth or higher order row, every second, third, fourth, or higher order grid point is left empty.

In some embodiments, the topographical structure may include a plurality of different features, e.g. a number of different features arranged in a regular, e.g. periodic, pattern, e.g. as alternating rows of two, three, or more different features. Examples of such patterns include structures comprising features with square cross-sections and features with circular cross-sections that are arranged in alternating rows.

In some embodiments, the features are arranged in lines and/or rows. In some embodiments, the features in each row have the same pitch distance, while in other embodiments the pitch distance may vary throughout a row and/or from row to row. Similarly, the row-to-row distance may be the same for all rows or vary from row to row. In some embodiments, some or all structures in a row may be rotated with respect to their respective neighbor(s) in the same row. In some embodiments, some or all structures in a row may be rotated with respect to their respective neighbor(s) in the neighboring row(s).

In some embodiments, the lateral dimension of the features in all lateral directions is between 1 µm and about 10 µm. Examples of such features include protrusions with generally square or circular cross sections. In other embodiments the lateral dimension of the features in one direction is between 1 µm and about 10 µm, while the lateral dimension in another direction is larger.

An example of a biocompatible material is one having a microstructure having a surface characterized by a topography comprising: a two-dimensional periodic structure of square pillars of dimension 2 µm×2 µm and pitch distance of 6 µm (FIG. 6).

FIGS. 8 A-K show top views of examples of the topographical structures on with features in the form of protrusions/pillars having a generally circular, square or rectangular cross-section. Each feature has a lateral diameter X in at least one direction, and the gap distance between features in adjacent rows and columns is denoted Y. In FIGS. 8 A, C, E, F, and I, Y is equal to the gap size between any feature and its nearest neighbor, corresponding to a pitch distance X+Y. In FIGS. 8 B, D, G, H, and J, the gap distance to the nearest neighbor is different for different features, as exemplified by features 1201, 1202, and 1203 of FIG. 8B. Feature 1201 has feature 1202 as its nearest neighbor; consequently the gap size is Y. However, feature 1203 has features 1201 and 1202 as its nearest neighbors with a slightly different gap size d. Accordingly, in FIGS. 8 B, D, G, H, and J, the pitch distances are different from row to row. In the row including feature 1201, the pitch distance is X+Y, while the pitch distance in the row including feature 1203 is 2(X+Y). Even though other heights are possible, the structures used in the examples below had a feature height of one of 0.6 µm, 1.6 µm or 2.4 µm.

In the examples of FIG. 8, the center of each feature is placed on a corresponding grid point of a 2-dimensional rectangular grid with grid constants a and b, as illustrated in FIGS. 8 A and B. However, in FIGS. 8 A-E, H-I not all of the grid points are actually covered by features, while in FIGS. 8 F and K all grid points are covered by features. In FIGS. 8 A, C, E, F, and I, the grid is a square grid with grid constant a=b=(X+Y). In FIGS. 8 B, D, G, H, and J, the grid is rectangular and the grid constants are a=X+Y and b=(X+Y)/2. In FIG. 8 K, the grid constants are a=2·X and b=3.5·X. For selected values of X and Y, wafers have been produced according to FIGS. 8 A-H where (X,Y) in µm were selected from (X,Y)=(1,1), (1,2), (1,4), (1,6), (2,1), (2,2), (2,4), (2,6), (4,1), (4,2), (4,4), (4,6), (6,1), (6,2), (6,4), (6,6). For selected values of X and Y, wafers have been produced according to FIG. 8 K, where X in µm was selected from X=1, 2, 3, 4, 5, 6, 7, 8. Accordingly, the grid constants a and b of the underlying grids were a=b=2-12 µm for the square grids of FIGS. 8 A, C, E, F, and I. For the rectangular grids of FIGS. 8 B, D, G, H, and J, the grid constants in direction a were in the interval between 2-12 µm, the grid constants in direction b were in the interval between 1-6 µm. For the grid of FIG. 8 K, the grid constant b lies in the interval between 3.5-28 µm and grid constant a lies in the interval between 2-16 µm.

For the purpose of identifying the above structures for different values of X and Y respectively, structures as shown in FIG. 8 A are referred to as AX.Y in the present description, where X and Y refer to the dimensions X and Y described above. Hence, structure AX.Y includes protrusions/pillars having a circular cross-section of diameter X µm. The protrusions are arranged in parallel rows, where the gap size between adjacent protrusions in every second row is Y µm, while the gap size between protrusions in the remaining rows is (2Y+X) µm. The gap size between protrusions of adjacent rows is Y µm. The protrusions in adjacent rows are aligned with each other.

Similarly, structures as shown in FIG. 8 B are referred to as BX.Y. Hence, structure BX.Y includes protrusions/pillars having a circular cross-section of diameter X µm. The protrusions are arranged in parallel rows, where the gap size between adjacent protrusions in every second row is Y µm, while the gap size between protrusions in the remaining rows is (2Y+X) µm. The gap size between protrusions of adjacent rows is Y µm. The protrusions in the rows having a gap size of (2Y+X) µm are aligned with the center of the gaps between protrusions of their respective adjacent rows.

Structures as shown in FIG. 8 C are referred to as CX.Y. Hence, structure CX.Y includes protrusions/pillars having a square cross-section of linear dimension of X µm. The protrusions are arranged in parallel rows, where the sides of the squares are aligned with the direction of the rows, and where the gap size between adjacent protrusions in every second row is Y µm, while the gap size between protrusions in the remaining rows is (2Y+X) µm. The gap size between protrusions of adjacent rows is Y µm. The protrusions in adjacent rows are aligned with each other.

Structures as shown in FIG. 8 D are referred to as DX.Y. Hence, structure DX.Y includes protrusions/pillars having a square cross-section of linear dimension of X µm. The protrusions are arranged in parallel rows, where the sides of the squares are aligned with the direction of the rows, and where the gap size between adjacent protrusions in every second row is Y µm, while the gap size between protrusions in the remaining rows is (2Y+X) µm. The gap size between protrusions of adjacent rows is Y µm. The protrusions in the rows having a gap size of (2Y+X) µm are aligned with the centre of the gaps between protrusions of their respective adjacent rows.

Structures as shown in FIG. 8 E are referred to as EX.Y. Hence, structure EX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with circular protrusions is Y µm, while the gap size between the square protrusions in the remaining rows is (2Y+X) µm. The gap size between protrusions of adjacent rows is Y µm. The protrusions in adjacent rows are aligned with each other.

Structures as shown in FIG. 8 F are referred to as FX.Y. Hence, structure FX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between protrusions within each row and between adjacent rows is Y µm. The protrusions in adjacent rows are aligned with each other.

Structures as shown in FIG. 8 G are referred to as GX.Y. Hence, structure GX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with circular protrusions is Y µm, while the gap size between the square protrusions in the remaining rows is (2Y+X) µm. The gap size between protrusions of adjacent rows is Y µm. The square protrusions in the rows having a gap size of (2Y+X) µm are aligned with the centre of the gaps between the circular protrusions of their respective adjacent rows.

Structures as shown in FIG. 8 H are referred to as HX.Y. Hence, structure HX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between protrusions within each row and between adjacent rows is Y µm. The protrusions in adjacent rows are aligned with each other. The square protrusions are aligned with the centre of the gaps between the circular protrusions of their respective adjacent rows.

Structures as shown in FIG. 8 I are referred to as IX.Y. Hence, structure IX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with square protrusions is Y µm, while the gap size between the circular protrusions in the remaining rows is (2Y+X) µm. The gap size between protrusions of adjacent rows is Y µm. The protrusions in adjacent rows are aligned with each other.

Structures as shown in FIG. 8 J are referred to as JX.Y. Hence, structure JX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with square protrusions is Y µm, while the gap size between the circular protrusions in the remaining rows is (2Y+X) µm. The gap size between protrusions of adjacent rows is Y µm. The circular protrusions in the rows having a gap size of (2Y+X) µm are aligned with the centre of the gaps between the square protrusions of their respective adjacent rows.

Hence, in the above examples, the minimum gap size between nearest-neighbor features is Y µm, and the minimum centre-to-centre distance between nearest-neighbour features is X+Y µm.

Structures as shown in FIG. 8 K are referred to as KX. Structure KX comprises groups of elongated protrusions (ridges) of rectangular cross section. The ridges have different lengths and are arranged parallel with each other. The ridges of each group are arranged to form a rectangular shape, such that each group includes a longest ridge as a central ridge. On each side of the central ridge are arranged a series of ridges becoming progressively shorter with increasing distance from the central ridge. The rectangular shape KX includes thus a sequence of ridges of lengths X µm, 2X µm, 3X µm, 4X µm, 3X µm, 2X µm, X µm. The width of the ridges is X µm. The distance between ridges is X µm. The groups of ridges are arranged in a predetermined pattern, such that the ridges are placed along rows, where each row includes ridges of two alternating lengths: A first type of rows includes alternating ridges of length X µm and 4X µm. A second type of rows includes alternating ridges of length 2X µm and 3X µm. The overall pattern of ridges resembles a sharkskin structure.

Other preferred structures will be described in connection with the examples below.

IV. Method of Synthesizing a Biocompatible Topographically Modified Surface of the Invention Over a Contoured, 3D Surface.

A surface of a container that is biocompatible for ES cells, may be manufactured by a number of production techniques, e.g. one or more of the following techniques:

Die imprinting: By using hard molds (e.g. of SiC or SiN) it is possible to produce patterns directly in other hard materials, like implant metals, by imprinting. The die, which is the master, is typically produced by a combination of e-beam lithography and Reactive Ion Etching. It has been shown that large arrays of nanostructures with width down to 40 nm can be printed in soft metals like Aluminium (S. W. Pang, T. Tamamura, M. Nakao, A. Ozawa, H. Masuda, J. Vac. Sci. Technology B 16(3) (1998) 1145. More specifically, it is desirable to generate die patterns in very hard materials like SiC or SiN when pressing in other hard substrates like Al, Ti, Titanium alloys, stainless steels, Ta, etc—otherwise the die will be damaged or even destroyed. The die imprinting can of course also be applied in softer materials like polymers. Since materials like SiC or SiN are difficult to dry-etch it is desirable to create an etch-mask consisting of e.g. Cr instead of just a photoresist. The mask can be produced in the following way: The lateral pattern is created by e-beam lithography in a resist followed by development, typically in an organic solvent like acetate. This leaves a resist pattern on the surface. The resist pattern is covered by a PVD—deposition of an approximately 100 nm Cr layer and at last lift-off by dissolving the resist using a standard resist remover. Dry etch of the hard die material can be carried out in a Reactive Ion Etching system. The depth of the structure is controlled by ion etching time. At last the Cr mask can be removed in cerium nitrate aqueous solution. Now the hard die is ready for imprinting in the surface for synthesizing a biocompatible topographically modified surface. The die can press micro- and nano-patterns in selected areas of the biomaterial by hydraulically pressing the die into selected areas of the surface. The pressure applied will typically be several tonnes for 10-30 seconds. Several areas can be patterned by consecutively patterning areas of the die size. The die size is typically from 10×10 mm$^2$ up to 40×40 mm$^2$. This micro- and nano-printing method is highly suitable for patterning selected areas on a contoured 3D implant produced by e.g. Ti, Titanium alloys, tantalum, or stainless steels. But it can of course also be applied to less hard materials like polymeric materials/coatings.

Imprinting by rolling a die. The method is basically the same as die imprinting, however, here the die is not flat but typically a cylinder. This die-roller is micro- and nanostructured by photolithography or e-beam lithography/Reactive Ion etching as described for the die imprinting above. The setup needs to be modified in order to take into account the curved surface. The die-roller can now be pressed on and rolled over selected areas of the biomaterial by hydraulically pressing the roller-die onto the surface of the implant, thereby imprinting the micro and/or nanostructure. Also here, the implant material can be hard like Ti, Ti-alloys, tantalum or stainless steel, but it does not have to be, so the method is also applicable for e.g. polymers.

Patterning by colloidal lithography: Here, it is possible to nano-pattern surfaces by depositing colloidal particles (e.g. polystyrene or the protein ferritin), which assemble in a short-range ordered pattern. These particles can e.g. be used as: an etching mask making pillars, a topographical template for making protrusions on the surface, or deposition of e.g. a nanometer metal cluster (e.g. by the metallic center of ferritin).

Laser patterning by ultra-short laser pulses: This technique can be utilized for high-precision patterning. In particular, the strong non-linearity of the ablation process leads to a well-defined threshold for material removal, and this has been used to demonstrate the formation of structures even below the diffraction limit (P. P. Pronko, S. K. Dutta, J. Squier, J. V. Rudd, D. Du, G. Mourou: Optical Communication 114, (1995) 106).

The laser patterning by ultrashort laser pulses can also be used in combination with pre-deposition of quartz spheres (K. Vestentoft, J. A. Olesen, B. H. Christensen, P. Balling: Appl. Phys A 80, (2005) 493 to create large arrays of nanometer-sized holes. More specifically, a layer of quartz spheres is deposited on the surface typically, but not necessarily, creating a densely packed array. By scanning an unfocused laser beam of ultrashort pulses across the surface with the quartz spheres, it is possible to generate large areas of structures in parallel, since the spheres act as individual lenses focusing the laser beam.

Laser scanning-beam Interference Lithography: This low-cost method can be used for fabricating periodic and quasi-periodic and spatially coherent patterns over large surface areas. The methods utilize the interference between two or more coherent planar wave-fronts. (S. Kuiper, H. van Wolferen, G. van Rijn, Journal of Micromechanics and Microengineering 11(1), (2001) 33.

Figure 9:
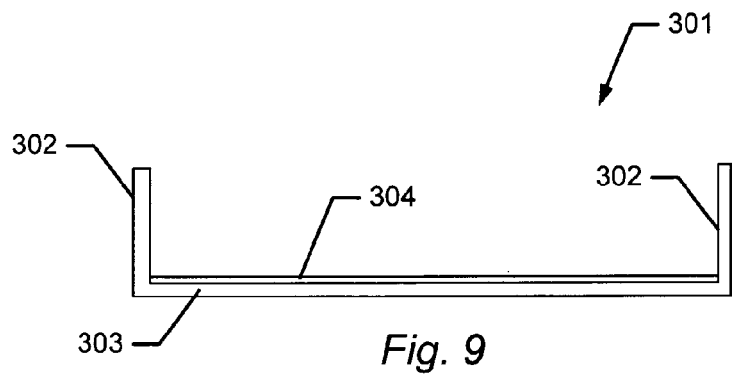
FIG. 9 schematically shows a cross-sectional view of a tissue culture dish having an exposed surface with a micro-scale structure.

V. A Device for Culturing Tissue or Cells Including an Exposed Surface Having a Microscale Surface Structure FIG. 9 schematically shows a cross-sectional view of a tissue culture dish having an exposed surface with a microscale structure. The dish 301 comprises an upwardly open receptacle having a bottom 303 and sidewalls 302. In use, the upper surface 304 is exposed to the cell culture or tissue and thus provides a microenvironment for the culture. In embodiments of the invention, the exposed surface 304 has a microscale topographical structure that is selected to promote a predetermined cellular function as described herein. Such surfaces can be produced in large quantities in e.g. polymers like polystyrene, different types of polycaprolactones, Poly (methyl methacrylate, silicones including poly(dimethylsiloxane), poly(hydroxyethyl methacrylate), poly(ethyl methacrylate), poly(D,L-lactide-co-glycolide), polyethylene, polycarbonate, polyvinyl alcohols, hyaluronic acid-based polymers, poly(ethylene oxide), poly(butylene terephthalate), methacryloyloxyethyl phosphorylcholine, mr-I T85, mr-I 7030, poly(bis(trifluoroethoxy)phosphazenes, natural polymers including modified poly(saccharide)s, e.g., starch, cellulose, and chitosan, and mixtures and co-polymers of the above mentioned, e.g. from a suitable stamp or blueprint by hot embossing or by injection molding, or by any other suitable process known in the art and/or as described herein. The surface 304 may be the upper surface of the bottom 303 or an upper surface of a separate element, e.g. a disk, placed on top of the bottom 303 of the dish. For example, such tissue culture dishes/flasks or any surface with structures selected to support the growth of embryonic stem cells in an undifferentiated state may be used to grow large quantities of embryonic stem cells that in a later development may be induced to differentiate into a desired cell type. Once differentiated into a specific cell type these specific cell types may be used for drug screening and/or cell replacement therapy.

The surface 304 may also be provided in the form of a separate tissue culture plastic that has been modified to display the selected structures or blueprint of these structures on the surface. For example, the separate tissue culture plastic may be removably inserted in the culture dish 301. In this respect the term tissue culture plastic is intended to include any polymers/metal coatings/material that can be used to produce a surface that can be used for growth of cells in vitro in cell culture.

EXAMPLES

Example 1

Manufacture of a BSSA Wafer Comprising 13×3 Tantalum Array of Tester Areas

A single-sided polished silicon wafer with a thickness of 525±25 μm provided a substratum for the manufacture of a biocompatible material. The wafer was an n-type wafer with a resistivity of 1-20 ohm cm. A micrometer-sized pattern was printed onto the polished side of the silicon wafer by standard photolithography and reactive ion etching in a $SF_6/O_2$ discharge according to the following protocol:

1. The wafers were pre-etched with buffered hydrofluoric acid (BHF, BHF is a solution of concentrated HF (49%), water, and a buffering salt, $NH_4F$, in about the ratio 1:6:4) for 30 seconds and then dried under $N_2$ flow, and
2. the wafer was then spin-coated with a 1.5 μm thick layer of photoresist AZ5214, Hoechst Celanese Corporation, NJ, US (the chemical composition can be found at the Material Safety Data Sheet (MSDS) supplied by Hoechst Celanese Corporation). and pre-baked at around 90° C. for 120 seconds, and
3. the photoresist-coated wafer was exposed to UV light for 5 seconds in an EVC aligner, model AL6-2, through a suitable mask, allowed to develop for 50-60 seconds and then post-baked for 1 minute at 120° C., and
4. the photoresist-coated wafer was then patterned by briefly etching with BHF for approximately 30 sec., and then subjected to Reactive Ion Etching (RIE) at a rate of approximately 0.30 μm/minute, and the resist was stripped with acetone followed by RCA cleaning. The RCA cleaning procedure has three major steps used sequentially: Removal of insoluble organic contaminants with a 5:1:1 $H_2O:H_2O_2:NH_4OH$ solution (SC1). Removal of a thin silicon dioxide layer where metallic contaminants may have accumulated as a result of (I), using a diluted 50:1 $H_2O:HF$ solution. Removal of ionic and heavy metal atomic contaminants using a solution of 6:1:1 $H_2O:H_2O_2:HCl$ (SC2).
5. The patterned wafer was then passivated by dry oxidation with a 20 nm $SiO_2$ layer, thermally grown at 1000° C. for 15 minutes.
6. A 250 nm tantalum layer was deposited onto the surface of the patterned wafer by sputter deposition.

The wafer was prepared comprising 168 structured squares and one control non-structured square as tester areas, wherein each area has a specific lateral topography, designated structures A-K [FIG. 8 A-K] prepared according to Example 1. Each of the structure patterns A-J is represented on 16 squares on the wafer but with varying dimensions as specified by (X,Y). The principle is illustrated for structure pattern A. The K structure is represented on 8 squares with varying dimensions as specified by the parameter T. X, Y and T are in μm. Wafers were produced according to these defined parameters, wherein the depth of the lateral topography was defined as either: 0.6 μm, 1.6 μm and 2.4 μm.

"AX/Y": Line structures as shown in FIG. 3. The structure includes trenches 41 of width X (in μm) and ridges 42 of width Y (in μm). Hence, the line structure of FIG. 3 has micrometer scale features along one dimension only. In Example 1, the areas A(2,2) include a line structures with trenches of width 2 μm and ridges of width 2 μm, the areas A(4,4) include line structures with trenches of width 4 μm and ridges of width 4 μm, the areas A(4,2) include line structures with trenches of width 4 μm and ridges of width 2 μm.

"BX/Y": A square-hole structure as shown in FIG. 4, The structure includes square holes/recesses 51 with dimension X(in μm)×X(in μm) and a pitch distance of X+Y, i.e. the net of ridges 52 have a width of Y. Hence, the structure of FIG. 4 has micrometer scale features in both dimensions within the plane of the surface of the tester area. In example 1, the areas B(4,4) include square holes with dimension 4 μm×4 μm and pitch distance 8 μm.

"KX/Y": A structure comprising rectangular holes/recesses separated by ridges as shown in FIG. 5. The structure includes rectangular holes 61 of dimension X (in μm)×Y (in μm) separated with ridges 62 of width X (in μm).

"DX/Y". A structure comprising protrusions/pillars as shown in FIG. 6. The structure comprises protrusions/pillars 71 with a square cross section of dimension X(in μm)×X(in μm) and a pitch distance of X+Y. Hence the areas D(2,4) include a square-pillar structure with pillar dimensions 2 μm×2 μm and a pitch distance of 6 μm.

"CX". A square-hole/pillar structure as shown in FIG. 7. The structure has the appearance of a chess board with holes 81 and protrusions/pillars 82, both having the shape of squares with dimension X(in μm)×X(in μm).

It is understood that the preparation method described above may also be applied to wafers with other forms and sizes of tester areas as well as other types of structures. The same production process may be used for a variety of different wafers, where the layout of the tester areas and the particular surface structures are determined by the mask through which the wafer is exposed.

Example 2

Figure 10:
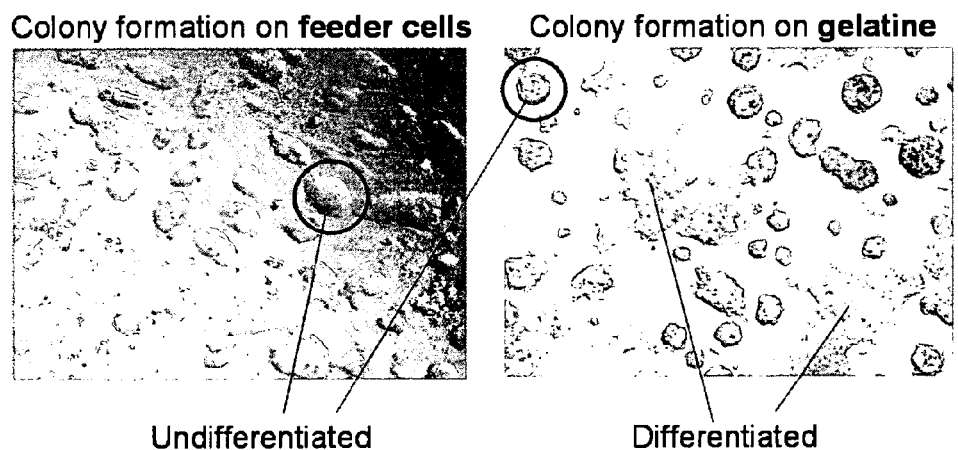
FIG. 10 shows the colony morphology and differentiation state of KH2 ES cells grown for two days on feeder cells (left panel) or in the absence of feeder cells but in a gelatin-supplemented medium (right panel). Examples of colonies of undifferentiated and differentiated ES cells are indicated. DIC, 10×

Identification of Biocompatible Surfaces for Promoting Growth of Pluripotent Mouse Embryonic Stem (ES) Cells Undifferentiated murine ES cells grow in compact, well-defined colonies (FIG. 10). When colonies flatten and spread out, the ES cells most likely have started to differentiate. Thus, colony morphology is an obvious and generally accepted marker of pluripotency. Examples of well established intracellular pluripotency markers are the transcription factors Oct4 and Nanog and the enzyme Alkaline Phosphatase (AP).

ES cells (KH2 cells and CJ7 cells) were seeded at a density from $1.3$-$5\times10^6$ cells/p10 Petri dish on tantalum BSSA wafers (FIG. 11), produced as in Example 1. The cells cultured for cultured for 3 days under conditions of 5% $CO_2$, 90% air humidity and 37° C. The cells were grown in DMEM supplemented with 15% FCS, 2 mM glutamine, 50 U/ml penicillin, 50 μg/ml streptomycin, non-essential amino acids, 100 μM β-mercaptoethanol and nucleosides, but in the absence of a feeder cell layer. Furthermore, the ES cell growth medium was supplemented with Leukemia Inhibitory Growth factor (LIF), 1000 U/ml, to assist maintenance of the undifferentiated phenotype of the ES cells. After 3 days culture the cells were stained for alkaline phosphatase (AP) activity (Blue), which provides a positive marker for undifferentiated murine ES cells.

Figure 12:
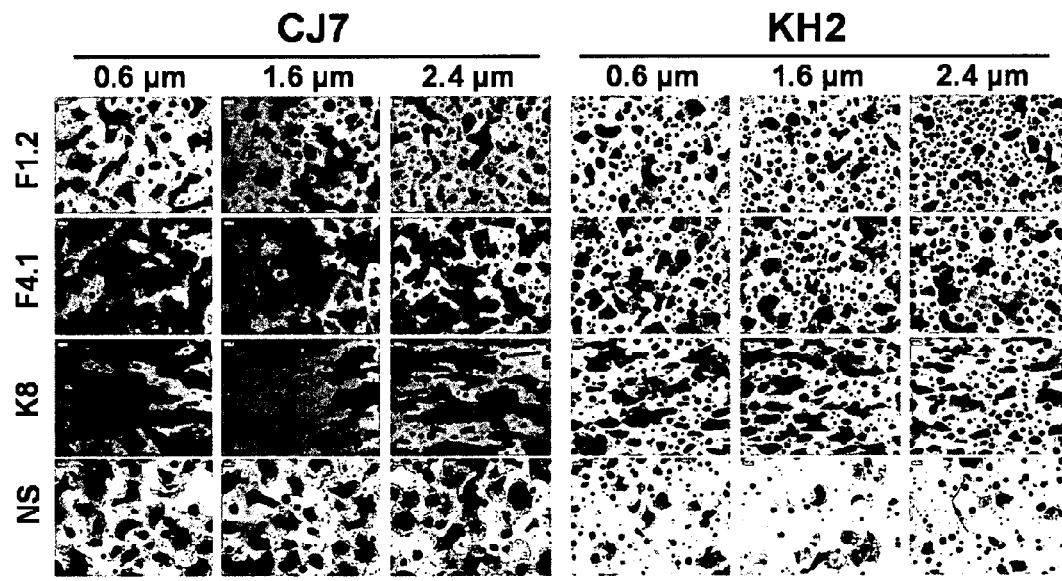
FIG. 12 shows CJ7 (left panel) and KH2 (right panel) ES cells that have been fixed and stained for AP activity following 3 days cultivation on BSSA wafers on each of the structures F1.2, F4.1 and K8. NS: Non-Structured square, where the height/depth of the structures on the wafer are either 0.6 µm, 1.6 µm or 2.4 µm. The different background colorings are due to light reflections in the tantalum structures. Scale bar: 160 µm. 5×

For both cell lines there were obvious differences in colony morphology among the different structures (FIG. 12). Generally, the CJ7 cells tended to differentiate more than the KH2 cells on the structures, but there are relevant common features: Colonies formed on F1.2 at 2.4 μm structure heights form well defined round colonies with AP activity. At the same structure height the colonies on F4.1 tend to flatten out and lose AP staining intensity. Colonies grown on the K8 structure are elongated and have a reduced AP staining intensity. Especially for the CJ7 cells this effect increases as the structure height is lowered. For the other structures the colony numbers are reduced when the structure heights are lowered. Reducing structure height also tends to increase colony size and reduce AP staining. The two cell lines respond differently to the NS square: CJ7 colonies started to differentiate, whereas KH2 colonies are small, well defined and reduced in number compared to their growth morphology on structured squares.

Due to the large number of biocompatible structures analyzed, the ES cell growth pattern was quantified using automated counting of colony number. This method was compared with manual counting based on colony morphology and AP staining intensity.

Comparison of manual and automated counting of undifferentiated KH2 ES colonies (FIG. 13) reveals that the automated counting consistently overestimates the colony number. However, the ratio (automated counting number)/(manual counting number) is relatively stable: 1.5±0.3. It appears that the characteristics of colony number development on the individual structures detected by automatic counting are in agreement with those characteristics detected by manual counting. A similar good correlation between manual and automated counting was obtained for the CJ7 cells. This confirms that the automated counting method was suitable for identifying biocompatible structures that generate e.g. high colony numbers. Furthermore the counting output also estimates the total area covered by the undifferentiated ES cell colonies (total ES cell colony area) and the total area covered with cells (total DAPI area). For this purpose, ES cells were stained with 4',6-diamidino-2-phenylindole [DAPI], a fluorescent stain that binds strongly to DNA and which can pass through intact cell membranes and thereby be used to stain both live and fixed cells. DAPI stained cells are detected by fluorescence microscopy, excited with ultraviolet light. When DAPI is bound to double-stranded DNA its absorption maximum is at 358 nm and its emission maximum is at 461 nm, which appears blue/cyan.

Figure 11:
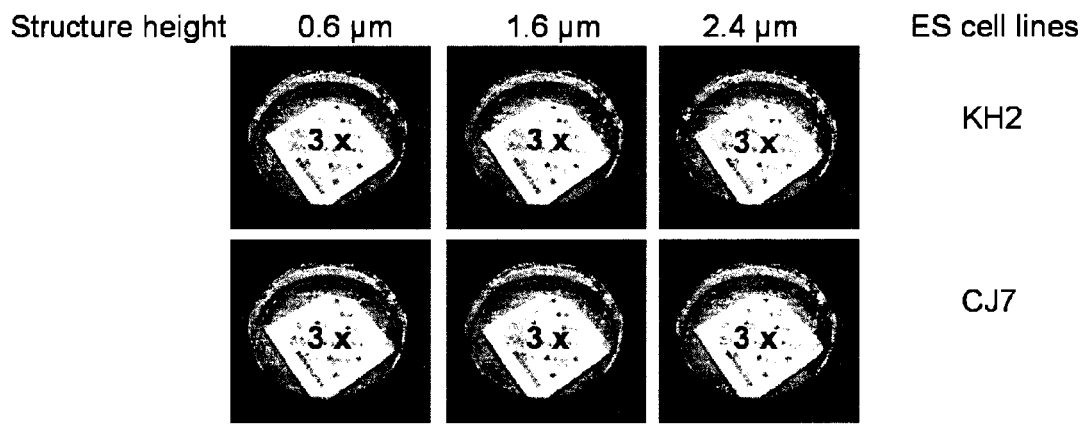
FIG. 11 shows CJ7 (lower row) or KH2 (upper row) ES cells seeded on a BSSA wafer comprising a topographical tantalum structure library in triplicate for each of the structure heights 0.6 µm, 1.6 µm and 2.4 µm.
Figure 14A:
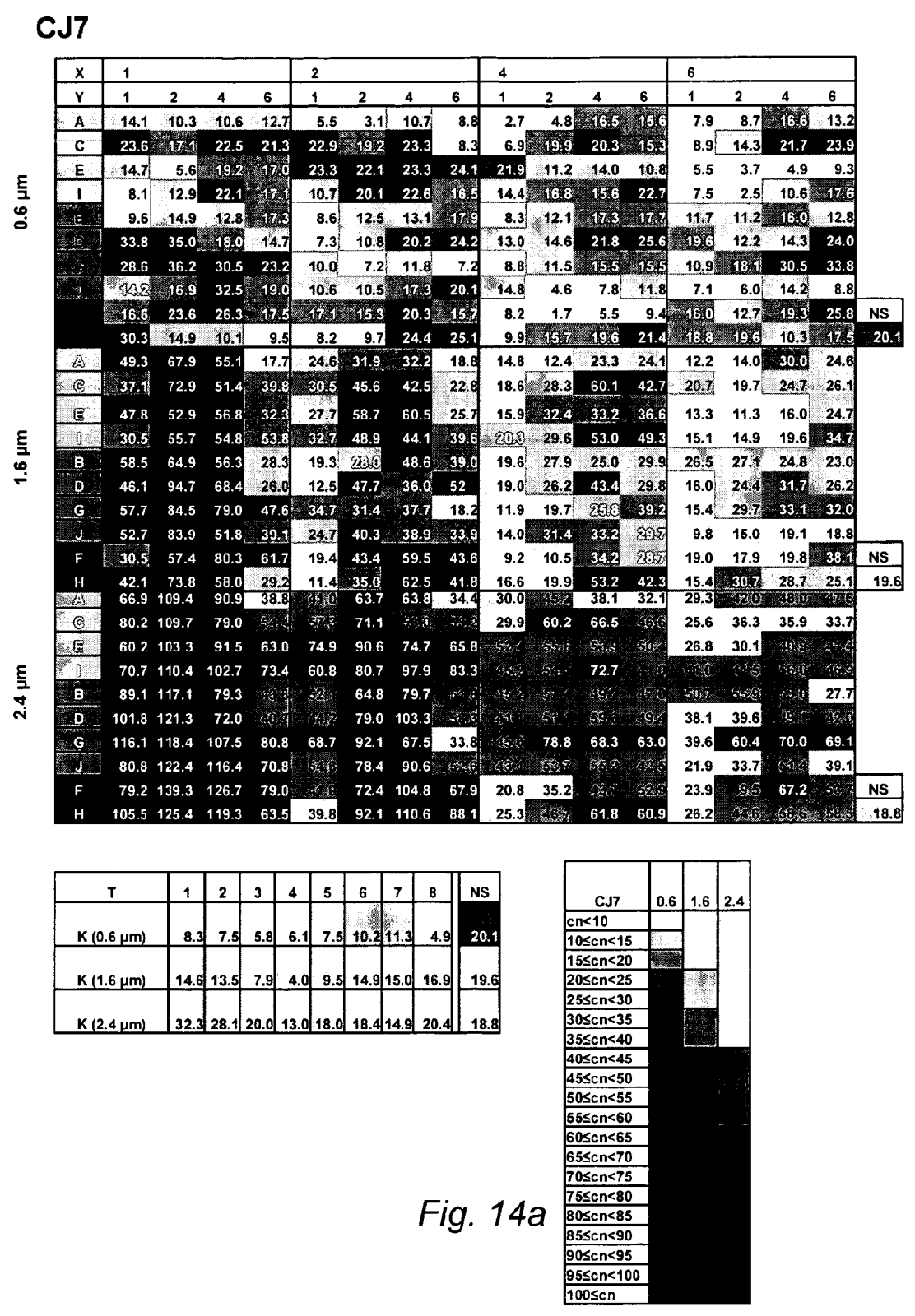

Automated counting was then used to quantify the results obtained from the experiment described in FIG. 11. Due to large variations in colony numbers on the different structure heights it was necessary to apply different shade scales for the different heights in FIG. 14, where the darker the shade the higher the colony number. In general, colony numbers increased as the dimension of X decreased. The highest colony numbers were obtained on structures where the dimension Y=2 μm or 4 μm and X=1 μm or 2 μm, while the lowest colony numbers were obtained when Y=1 and X=2 μm, 4 μm or 6 μm. Low colony numbers were seen on all K structures.

Figure 15:
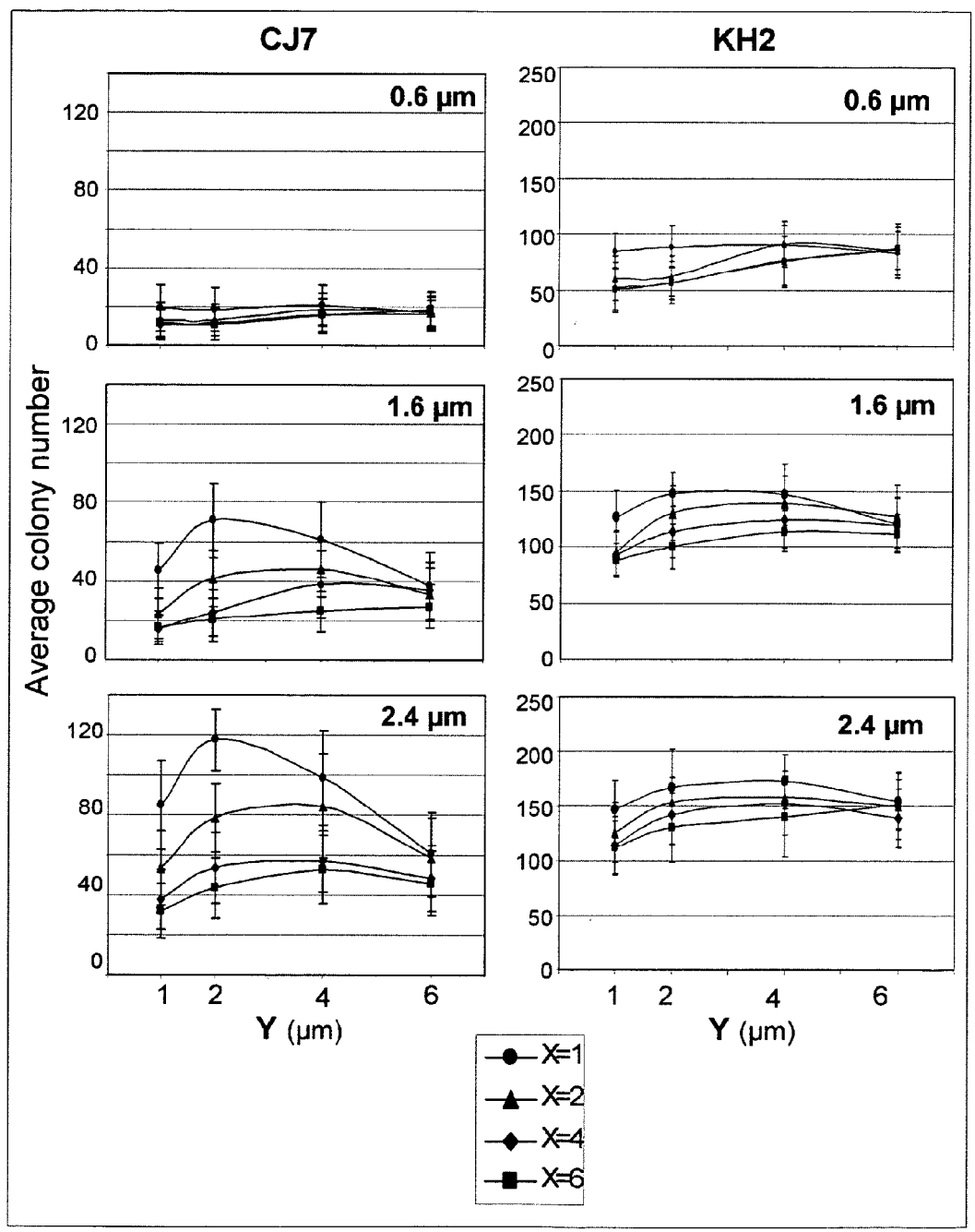
FIG. 15 shows a graphical representation of the ES cell colony number with respect to the dimensions of the structure on which the ES cells were grown. Data obtained from structures A-J having the same dimensions for X and Y, were pooled for each of the ES cell lines CJ7 and KH2 for each of the three structure heights/depths (0.6, 1.6 and 2.4 µm). Each curve represents a fixed X value and the value of the Y is given on the horizontal axis. Average colony numbers are given on the vertical axis.

The effect of the different tested biocompatible surface structures can be further seen from FIG. 15. Surface structures having protrusions with a small minimum cross-sectional diameter (small X) give rise to the highest ES cell colony numbers, whereas those with larger values of X gave rise to lower colony numbers. Furthermore, the figure confirms that structures where the dimension Y=2 μm or 4 μm give rise to the highest colony numbers, depending on the value for X. Thus we have identified a local optimum for colony formation concerning the Y values (the distance between the columns of the structure). By extrapolation, colony numbers will be further increased on structures having an X dimension of less than 1 μm.

Inspection of FIG. 15 reveals that unfavorable conditions for the proliferation of undifferentiated ES cells are associated with surface structures having less than one protrusion per 65 μm$^2$ and surface structures where the area of the protrusions exceeds 25% of the total surface area. It follows that optimal proliferation of undifferentiated ES cells are associated with surface structures that fulfill both conditions.

Figure 16:
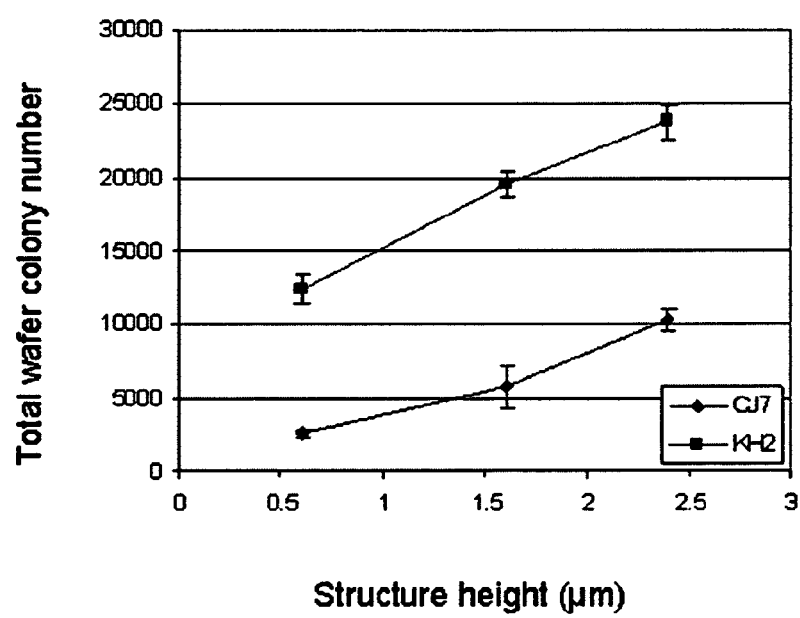
FIG. 16 shows a graphical representation of the ES cell colony number with respect to the height/depth dimensions of the structure on the wafer on which the ES cells were grown. The horizontal axis gives the height/depth of the structure (µm) on the BSSA wafer and the vertical axis gives the total ES cell colony number detected on the wafer. Triple assay average values are shown for the two cell lines, CJ7 and KH2.
Figure 17:
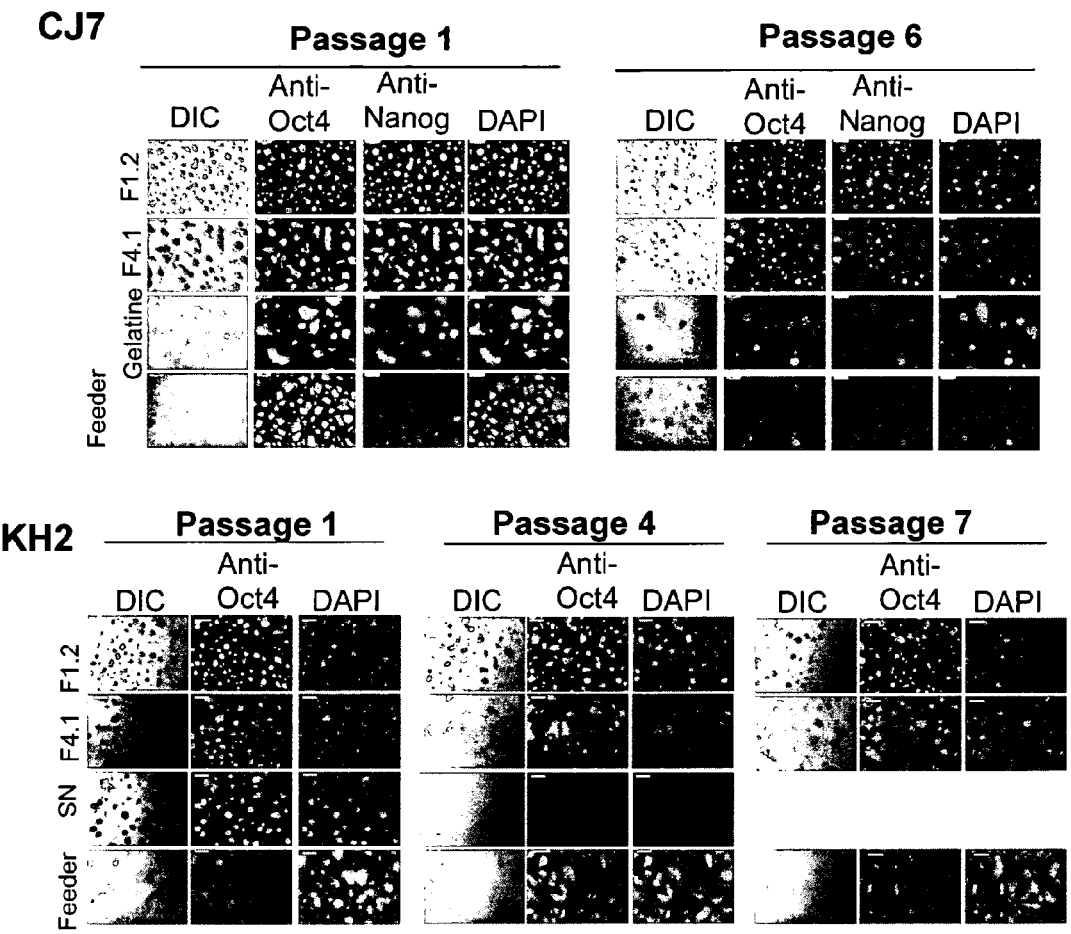
FIG. 17 shows a Differential Interference Contrast (DIC) image of CJ7 and KH2 ES cells grown by serial passaging on either: biocompatible tantalum surface structures: F1.2, F4.1 having a height/depth of 2.4 µm; media comprising feeder cells; gelatin-coated dishes (CJ7 cells only); or Non-Structured (NS) tantalum (KH2 cells only). The CJ7 cells were expanded during 6 passages and the KH2 cells during 10 passages (Passage 7 is shown). CJ7 cells were stained for expression of Oct4 (using anti-Oct4 antibodies) and Nanog (using anti-Nanog antibodies) as well as for nuclei (DAPI). KH2 cells were stained for Oct4 expression and nuclei (DAPI). 10×.

FIG. 16 shows the relationship between the structure heights and the ES cell colony number for the CJ7 and the KH2 cell lines. It is the total ES cell colony number from the whole wafer that is given on the vertical axis. Colony number clearly increases with structure height and this effect is seen for both cell lines.

All together the data analyses revealed that structures with X=1, Y=2 or 4 and structure height 2.4 μm generate the highest colony numbers.

Example 3

Pluripotency and Growth Morphology of Mouse Embryonic Stem (ES) Cells is Maintained During Serial Passaging on Biocompatible Surfaces The previous examples demonstrate that biocompatible surfaces having different surface structures can be used to promote a high ES colony number (for example structure: F1.2) or to promote low ES colony number (for example structure: F4.1). The sustained effect of these structures on the growth of ES cells was examined during serial passaging of CJ7 and KH2 ES cells. After each passage, the ES cells were fixed and analysed for Oct4 and Nanog expression using antibodies specific for Oct4 and Nanog. The ES cells CJ7 and KH2 still express the pluripotency markers after 6 and 10 passages respectively on F1.2 (F1.2 has dimensions X=1; Y=2) or F4.1. (F4.1 has dimensions X=4;Y=1). The CJ7 and KH2 cells also expressed alkaline phosphatase in the last passage. ES colonies generated on F1.2 structures retained a compact and well defined morphology during passaging, while colonies generated on F4.1 retained their morphology.

Taken together, these results indicate that the effect of the structures on ES cell colony formation is sustained during passaging.

Example 4

Figure 18:
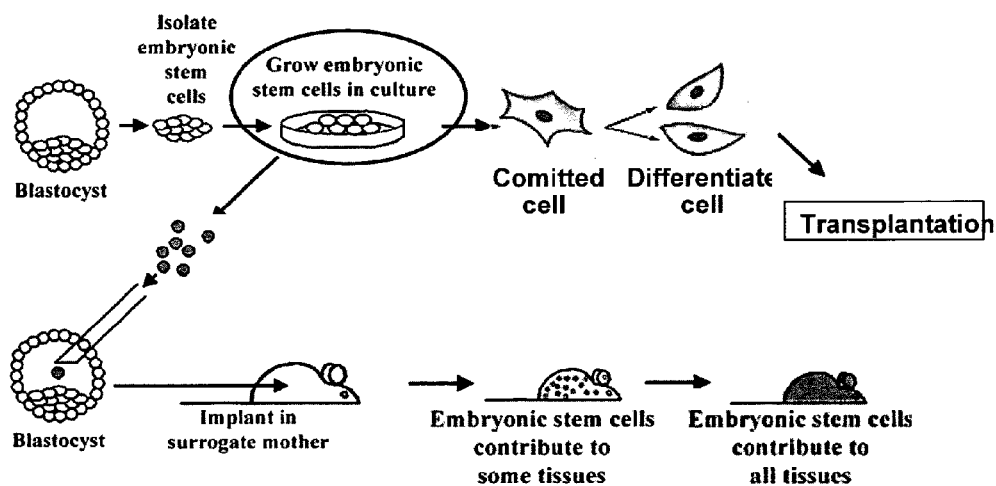
FIG. 18 shows a cartoon demonstrating the use of ES cells in transplantation or germline transmission. ES cells are isolated from the inner cell mass of the blastocyst. In culture these cells can be expanded indefinitely and are pluripotent: they have the potential to differentiate into cell types from all the three germlayers. Consequently there are high expectations as to their application in regenerative medicine. Another important use of ES cells is for re-introduction into mammalian embryos, such as mouse embryos, at the blastocyst stage. When ES cell containing blastocysts are implanted in a pseudopregnant mouse, pluripotent ES cells may contribute to development of different tissues in the 1. generation offspring from this mouse. High quality ES cells may then contribute to the germline and thus a second generation mouse descending purely from ES cells may be generated.

Germline Potential of Mouse Embryonic Stem (ES) Cells Obtained by Serial Passaging on Biocompatible Surfaces A cartoon showing steps in a protocol for the germline transmission of ES cells is shown in FIG. 18. The germline potential of CJ7 ES cells, following in vitro serial passaging, was tested employing the blastocyst injection protocol outlined in FIG. 18. CJ7 cells were passaged on one of: a biocompatible surface structure F1.2, F4.1; gelatin-coated culture plates; or media supplemented with feeder cells (according to example 3). CJ7 cells from each of the cell populations harvested after passaging, were then injected into blastocysts which were implanted in surrogate mothers. Among their offspring chimeric male pups were selected for breeding. CJ7 cells passaged on F1.2 or on media comprising feeder cells maintained germline potential, while no germline potential was seen from cells passaged on F4.1; or gelatin-coated culture plates, showing that at least cells passaged on the F1.2 structure maintained the capability to go germline.

Example 5

Identification of Biocompatible Surfaces for Promoting Uniform Differentiated Growth of Mouse Embryonic Stem (ES) Cells ES colonies grown in vitro are seen to flatten and spread which is indicative of ES cell differentiation (FIG. 10). Thus, colony morphology is an obvious and generally accepted marker of both pluripotency and differentiation.

A differentiation index, based on the total DAPI-covered area minus the area that has been ascribed to the ES colonies, provides a measure of the extent of ES cell differentiation induced by a given biocompatible structure.

Figure 21:
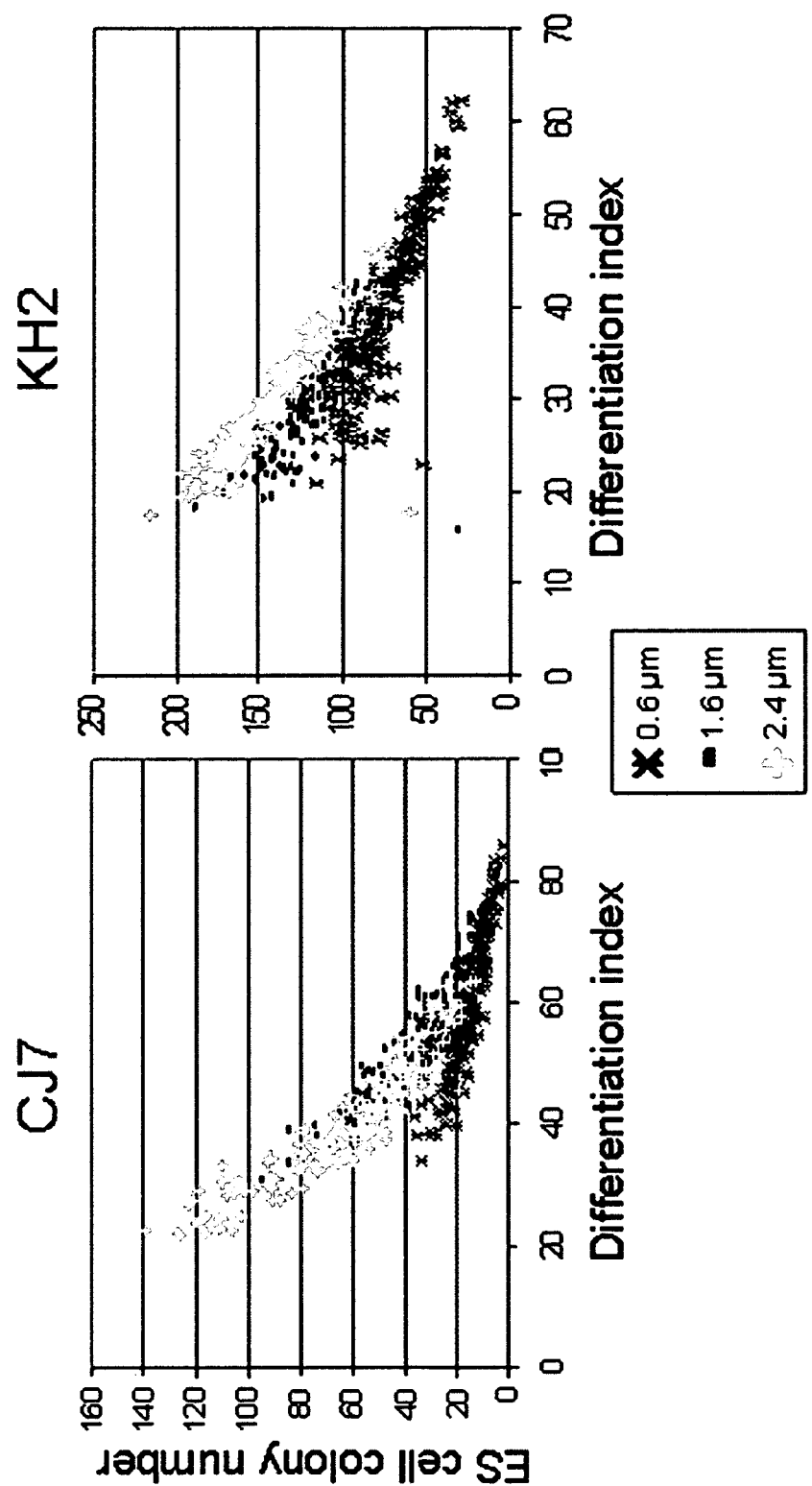
FIG. 21 shows a graphical plot of ES cell colony number versus differentiation index. Triplicate average values, derived from the data shown in FIGS. 14 and 20 are given for both CJ7 and KH2 ES cells. Different structure heights (0.6, 1.6 and 2.4 µm) are represented by different shades. The differentiation index is given on the horizontal axis, and the ES cell colony number on the vertical axis.
Figure 22:
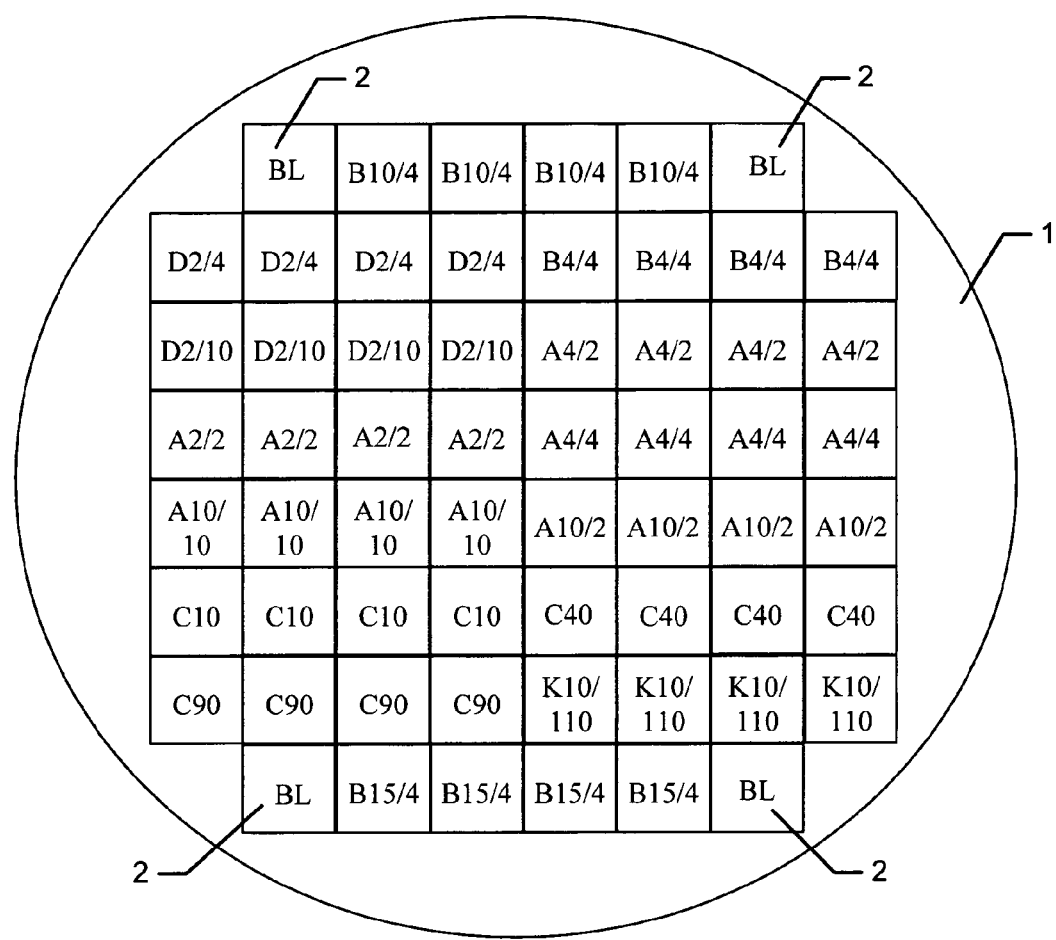
FIG. 22 shows a schematic top view of a topographical structure included in a BSSA wafer, where the center of each projection (pillar) is placed on a grid point of a 2-dimensional grid, e.g. a hexagonal, a rectangular or a square grid with predetermined grid constants.

Accordingly, the differentiation index has been determined for the ES cells grown on the BSSA wafer according to Example 2. FIG. 20 sets out the determined differentiation index, where a darker shade corresponds to a higher differentiation index. For all types of surface structure tested, an increase in the value of the dimension X led to an increase in differentiation index (X=6>X=4>X=2>X=1). Also, structures with Y=1 and the K structures had relatively high differentiation indexes and, overall, the differentiation index increases with decreasing structure height (0.6 μm>1.6 μm>2.4 μm). It is further seen that surface structures that give rise to high colony numbers have a low differentiation index and structures with low colony numbers have high differentiation indexes (FIG. 21). The lowest colony numbers and the largest differentiation indexes are obtained for cells grown on the structures with a height of 0.6 μm.

Example 6

Study of Culturing Human Embryonic Stem Cells on Biocompatible Surfaces

Introduction

Human embryonic stem (hES) cells are pluripotent cells derived from the inner cell mass of a human blastocyst and generally cultured on mouse embryonic fibroblasts (mEF) feeder layers. Passage of undifferentiated cells is routinely achieved by manual micro-dissection of hES colonies using finely drawn Pasteur pipettes and subsequent plating on fresh mEF feeder layers. This method is very laborious and time consuming and unsuitable for large scale cell culture. Development of culture techniques where hES cells can be propagated in the absence of an animal feeder layer are a prerequisite for the use of hES cells in human cell therapy and high throughput drug discovery.

To meet these needs, hES cells were cultured on topographically structured surfaces in order to determine whether these surfaces can support hES growth, whether hES cells cultured on these surfaces maintain their pluripotency and whether the hES cells continue to grow and maintain pluripotency when cultured on the biocompatible surfaces after subsequent passaging.

Methods

Based on previous screening of the different surfaces by a BioSurface Structure Array (BSSA) wafer, see FIG. 1, on mES culture, four surfaces were selected for the culture of hES cells, i.e. F(1,2), F(1,4). F(4,1), G(4,1) wherein the height/depth of the features (projections) on each microstructured surface were 2.4 μm. Preliminary experiments had already shown that hES cells (King's College London cell lines) grew better on surfaces F(1,4) and F(1,2), thereby focusing on these two surfaces. Undifferentiated hES cell (KCL-002) cultures were maintained on mouse embryonic fibroblast (mEF) feeder layers in medium containing 10% ES grade FBS. Undifferentiated colonies were manually cut from the mEF feeder layer and approximately 5-6 pieces were plated onto each of the biocompatible surfaces.

Results

Cell Attachment

First, the cells were checked to determine if they could adhere to the surface. To do this, undifferentiated hES cell layer was manually cut into small pieces and plated on the respective surfaces. It was found that the cells were able to settle down very well on both 2 surfaces, F(1,4) and F(1,2), the next day. Adherence capacity comparison of the two surfaces revealed that more cell colonies attached on surface F(1,4) compared with surface F(1,2). Furthermore, cell colonies were also tested in KnockOut serum replacement (KOSR) instead of serum. To test this, hES cell colonies were cultured in KOSR on mEF feeder layers for 4 passages and then transferred onto the F(1,2) and F(1,4) surfaces. It was found that the cell colonies settled down inefficiently on either surface F(1,4) or F(1,2) by the next day. However, a relatively larger number of colonies adhered to surface F(1,4) than to surface F(1,2). This indicates that surface F(1,4) is relatively more efficient in cell attachment than surface F(1,2), but that the cells attached much better to the surfaces when cultured in serum than in KOSR.

Cell Growth

To ascertain if hES cells can proliferate on the surfaces, the cell colonies were plated on the surfaces and cultured in 2 ml hES medium containing 10% Fetal bovine serum (FBS). The medium was replaced every other day and supplemented with 1 ml in the interim. It was found that cell colonies grew well on both surfaces, F(1,4) and F(1,2), in the presence of FBS serum.

As shown in FIGS. 30 & 31, hES colonies are able to proliferate on the surfaces. In general, the size of each colony increased 30-40% each day. The morphology of hES cell colonies grown on the surfaces was very similar to those grown on Geltrex™ (Invitrogen), FIG. 32.

Maintenance of the Pluripotency of the hES Cells

To determine if the hES cells are able to maintain their pluripotency on the surfaces, the cells were grown for a week then fixed in 4% PFA and stained with anti-Oct4 (Octamer-4) antibody. Images are seen in FIGS. 33 & 34.

DAPI was used to stain all the nuclei. Oct4 is a transcription factor localised at the nucleus of undifferentiated hES cells. FIGS. 33 and 34 show that 50-70% of cells were immuno-positive to Oct4 after 1 week of culturing on the surfaces. This indicates that majority of the cells are able to maintain their pluripotency on the surfaces.

Summary

To summarise, hES cells can grow very well on the microsurfaces F(1,4) and F(1,2) having a feature height/depth of 2.4 µm, and maintain their pluripotency as demonstrated by Oct4 expression. Cells could be passaged by Collagenase IV digestion, however this impeded cell growth.

The Invention According to a Second Aspect

This aspect relates to the need for implants to be successfully incorporated in the bone tissue in order to obtain good clinical results. Major advances and results have been achieved in this area during the last decades, but implant loosening over time continues to be a significant problem for successful long-term joint replacements. An implant or device having a surface that can promote expression of osteopontin and osteocalcin in bone-forming cells may improve the outcome of treatments based on their use. Thus, the invention provides a biocompatible material or structure, which supports bone formation by expression of osteopontin and osteocalcin by bone-forming cells (including osteoblasts).

Orthopedic implants have a limited lifetime, where poor adhesion between the implant and bone tissue can lead to dislocation of the implant. Thus the invention further provides an implant surface, which supports expression of osteopontin and osteocalcin by bone-forming cells, thereby improving the biocompatibility of the implant.

The present invention is based on the recognition that cellular functions that direct gene expression, growth, and/or differentiation are strongly influenced by the cell's microenvironment. Thus, it is thought that gene expression in bone cells in vivo, and in vitro, may depend on the provision of a suitable structure to which the cells can attach. In particular the invention recognizes that the 2- and 3-dimensional architecture, or topography, of surfaces in the microenvironment of a cell, is a critical factor for above processes. There are a myriad of different possible microenvironments. In one aspect, the present invention thus concerns the provision of a biocompatible material whose surface topography creates a specific microenvironment that may enhance expression of osteopontin and osteocalcin by bone-forming cells and lead to a better integration of the implant into the remaining bone. Other cell functions that may be influenced by the topography of surfaces include cellular growth, expansion, isolation, migration, differentiation, dedifferentiation, intra- or intercellular organization, etc. As proteins and cells range in size from nano- to micro-meter these are relevant length scales for the problem of providing a biocompatible material.

I. Method of Demonstrating the Biocompatible Properties of and the Promotion of Cellular Functions, E.G. the Promotion of Mineralization, by the Biocompatible Material of the Invention.

The biocompatible material or structure of the invention may be identified by screening materials with different surface topography using a screening tool/assay that provides different candidate topographical structures.

In particular, a mineralization assay, employing for example Alizarin red staining (Example 2), von Kossa staining (von Kossa, J (1901): "Ueber die im Organismus kuenstlich erzeugbaren Verkalkungen." Beitr Pathol Anat Allg Pathol 29: 163-202), ectopic bone formation (Example 3), and in vivo bone formation/bone ingrowth (Example 4) provides a tool for demonstrating the properties of the biocompatible material of the invention and for selecting suitable topographical structures that promote mineralization.

An example of a screening tool suitable for the screening of topographical structures includes a so-called BioSurface Structure Array (BSSA) wafer. FIG. 1 shows a top view of an example of such a biosurface structure array wafer. The BSSA wafer 1 comprises 60 tester areas. A number of tester areas 2 are left "blank", i.e. they have not been processed to have a structured surface. Consequently, the surfaces of the tester areas 2 are substantially flat. Consequently a control experiment is inherently included in each parallel screening test with the BSSA screening tool. The remaining tester areas, designated S1, S2 . . . , S54, comprise respective structured surfaces as described herein. The tester areas are squares of dimension 10 mm×10 mm.

A wafer for use as a screening tool to identify structures that induces/enhances cellular functions such as mineralization, growth and gene expression may be manufactured by a number of production techniques.

Examples of procedures for its manufacture include one or more of the following techniques that are known as such in the art:

Photolithography methods: Photolithography is a process known as such in which geometric shapes/patterns are transferred from a photomask to the surface to be structured, e.g. the surface of a wafer. Photolithography equipment with minimum lateral feature sizes ranging from around 1 micrometer to below 100 nm is known as such. Photolithography processes are described in e.g. S. M. Sze: Semiconductor Devices, Physics and Technology, 2nd Edition, John Wiley & Sons 2002, Chapter 12:

Lithography and Etching; and in Plummer, Deal, Griffin: Silicon VLSI Technology, Fundamentals, Practice, and Modeling, Prentice Hall 2000, Chapter 5: Lithography.

E-beam lithography: In principle, E-beam lithography can be used to expose a photoresist in exactly the same way as the light is used in photolithography. E-beam lithography has a particularly high resolution up to around 5 nm.

Hot embossing: Hot embossing uses a master stamp to imprint micro- and nanometer scale structures on polymer substrates. The method allows the master stamp to produce many fully patterned substrates using a wide range of polymer materials. Hot embossing provides a low-cost, highly versatile manufacturing method that is well suited for the manufacture of BSSA for uses ranging from research and development applications to high-volume production. High aspect ratios with a very high degree of homogeneity may be achieved for micro- and nanometer scale structures on large-sized wafers, such as 8 inch or 12 inch wafers. Features sizes below 20 nm are possible. The master stamp may be produced by e.g. E-beam lithography techniques.

Other examples of production steps or processes that may be involved in the production of the biocompatible material or structure include nano imprint lithography, laser ablation, chemical etching, plasma spray coating, abrasive blasting, engraving, scratching, micro machining, or the like.

FIG. 2 shows a cross sectional view of the wafer of FIG. 1. FIG. 2a shows a cross section of the entire width of the wafer along the line labeled A-B. FIG. 2b shows an enlarged view of a portion of the surface of one of the tester areas. The wafer 1 has a layered structure including a patterned substrate layer 21, e.g. a silicon layer, and a surface layer 23. The surface of the wafer is patterned, e.g. by a photolithography process, to provide different patterns on the surfaces of the respective tester areas S1, S2, . . . , S54. The structures have a depth/height H. In a photolithography process the height H is controllable by the etching process. The patterned surface is covered by a thin layer of silicon dioxide 22, and/or a surface layer 23 of a different biocompatible material such as tantalum or any other metal, metal oxide, metal nitrides, metal carbides, diamond, diamond like carbon, semiconductor, semiconductor oxide/nitride, insulator, polymers, copolymers. Between the tester areas there is a "blank" border area with no structure, i.e. the border area has not been processed to have a structured surface. In this case the width of the blank border area is 0.3 mm. A blank border line aids visual alignment and identification of the structures. The blank border further serves as a small control surface next to each tester square.

It is noted that the FIG. 2 is schematic and not drawn to scale. In particular, the vertical dimensions may be exaggerated to improve readability.

II. Chemical Composition of a Biocompatible Material of the Invention

Embodiments of a biocompatible material or structure may take a variety of forms, such as a medical implant or a biocompatible coating for use in the manufacture of a medical implant, a tissue culture dish/flask having a surface to be exposed to the cell culture, where the exposed surface with structures supporting the desired cellular function, e.g. growth or differentiation of neurons or embryonic stem cells in an undifferentiated state, a tissue culture surface or e.g. tissue culture plastic that has been modified to display these structures or blueprint of these structures on the surface. In this respect tissue culture plastic means any polymers that can be used to produce a surface that can be used for growth of cells in vitro in cell culture.

Embodiments of a biocompatible material or structure may comprise a substrate layer, and optionally, a surface layer.

Suitable base materials for the preparation of the biocompatible material or structure include any semiconductor (doped or not-doped), a single metal, a metaloxide, a metal nitride, an alloy, a ceramic, a polymer, a co-polymer, a composite, a drug delivery system, a polymer with bioactive molecules, other bioactive compounds or any combination thereof.

In embodiments of the invention, the surface layer comprises a material that is sufficiently biocompatible to enhance the mineralisation of bone-forming cells. Examples of surface layers include a metallic surface deposit, e.g. tantalum, titanium, Ti—Al—V alloys, gold, chromium, metal oxides, semiconductor oxides, metal nitrides, semiconductor nitrides, polymers, biopolymers, or other alloys. Preferred surface compositions for implants include tantalum or titanium.

In some embodiments, the biocompatible material or structure comprises additional components such as one or more bioactive compound, which may be deposited or adsorbed on the exposed surface or surface layer of said material or structure. For example, said compound may be selected from the group consisting of an antibody, antigen, glycoprotein, lipoprotein, DNA, RNA, polysaccharide, lipid, growth hormone, organic compound, and inorganic compound. Preferably, a growth hormone selected from the group consisting of BMP, EGF-like, TGF-beta is adsorbed or bound to the surface of the biocompatible material.

III. Structural Properties of a Biocompatible Material of the Invention

All or part of the surface of the biocompatible material or structure (which may take a variety of forms as described above) comprises micrometer scale features in one or more dimensions within the plane defined by the surface of the material or structure. The terms micro scale and micrometer scale as used herein are intended to refer to a length scale in the range of between about 1 µm and about 1000 µm. The term nanometer scale as used herein is intended to refer to a length scale in the range of between about 1 nm and about 1000 nm, in particular between about 1 nm and about 100 nm.

In embodiments of the invention, the features are structural/topographical features such as protrusions extending out of the surface of the biocompatible material.

The surface of the biocompatible material may include a micrometer scale feature having a lateral dimension in at least one lateral direction, measured in a direction substantially parallel to the surface or at least substantially tangential to the surface. This lateral dimension is selected from one of the intervals: between about 1 µm and about 20 µm; between about 1-10 µm; between about 10-20 µm, between about 1 µm-2 µm, between about 2 µm-4 µm, between about 4 µm-6 µm, between about 6 µm-8 µm, between about 8 µm-10 µm; between about 10-12 µm; between about 12-14 µm; between about 14-16 µm; between about 16-18 µm; between about 18-20 µm.

In a preferred embodiment of the invention, the protrusions have a cross section with a minimum cross-sectional diameter 1.0 µm-2.0 µm.

The disposition of micrometer scale features at the surface of the biocompatible material is preferably periodic along one or more lateral direction, and may be described by a periodic function having a lateral pitch dimension selected from one of the intervals: between about 1 µm-2 µm, between about 2 µm-4 µm, between about 4 µm-6 µm, between about 6 µm-10 µm, between about 10 µm-16 µm, between about 16 µm-20 µm, between about 20 µm-24 µm.

In a preferred embodiment of the invention, the distance between adjacent grid points along at least one dimension is between 2.0 µm and 9.0 µm.

The maximum distance, or gap, between any micrometer scale feature and its nearest neighbor has lateral dimension in at least one lateral direction where said dimension is selected from one of the intervals: between about 0.5 µm-1 µm, between about 1-2 µm, between about 2 µm-4 µm, between about 4 µm-6 µm, between about 6 µm-8 µm, between about 8-10 µm, between about 10 µm-12 µm, between about 12 µm-14 µm, between about 14 µm-16 µm.

In a preferred embodiment of the invention, the lateral dimension of the maximum gap between any protrusion and its nearest neighbor (d;Y) is between about 1.0 µm-6.0 µm. More preferably, the cross-sectional diameter of the cross section is about 1 µm and the lateral dimension of the minimum gap between any protrusion and its nearest neighbor (d;Y) is about 1.0 µm.

The periodic function of the micrometer scale features may have a smaller period along one direction and a larger period, e.g. by a factor of 2, 3, 10 or larger, in another direction. Any one micrometer scale feature at the surface of the biocompatible material may be defined as a period of the periodic structure. Hence, the lateral dimensions of a feature of a periodic structure may be defined as the period of the periodic shape/function, i.e. the length of the shortest interval over which the structure repeats its shape.

The depth/height of the micrometer scale features, i.e. their linear dimension in a direction projecting out of the surface of the biocompatible material may be on the nano- or micrometer scale, i.e. the structures may have heights/depths in the range 1 nm-10 µm.

In a preferred embodiment of the invention, each of the protrusions of the topographical structure has a vertical height/depth dimension equal to or greater than 1.60 µm, preferably about 2.4 µm.

The lateral cross section of any one micrometer scale feature is preferably geometrical, such as square, rectangular, hexagonal, polygonal or star-shaped. The top and/or side surfaces of the feature are preferably substantially flat. The surfaces of the micrometer scale features can, however, also include features on the nanoscale to achieve a synergistic effect of the topography both on the micrometer and nanometer scale. This can be obtained by e.g. chemical etching (e.g. by NaOH or citric acid), ion etching, colloidal lithography (e.g. by polystyrene beads, bucky balls or proteins), grazing incidence Physical Vapour Deposition coating, CVD coating, or plasma spraying. The features at the surface of the biocompatible material may have the same or different shapes. Preferably the features at the surface of the biocompatible material are geometric (e.g. square, rectangular, hexagonal, star-shaped, or polygonal) in shape.

In some embodiments, the cross-sectional shape of the features may be derived from a simple geometric shape, such as a square, a circle, or the like, e.g. by modifying the corners of a square. Examples of such modifications include the cutting off and/or rounding off of corners. Hence, such shapes are generally square, circular, or the like, but they deviate slightly from a perfect square or circular shape, thereby introducing additional corners and/or modifying the angles between the edges that meet at each corner.

In general, a 2-dimensional periodic structure may be defined by a unit cell in the plane of the surface having a predetermined shape, such as square, rectangular, hexagonal etc., and a repeat unit defining the detailed structure (the base) in the unit cell, such as holes or protrusions, e.g. square pillars, polygonal pillars, circular pillars, pyramids etc. The positions defined by that unit cell define the repeat distances, while the repeat unit defines the predetermined shape and size. These unit cell positions may be defined by respective 2-dimensional vectors. The grid structure thus results from a translation of the unit cell along the two dimensions defined by the surface, in particular respective multiples of the unit cell dimensions. In one embodiment, the centre position of each feature may be defined by a vector $v=n_1 v_1 + n_2 v_2$, where $v_1$ and $v_2$ are linearly independent vectors in the surface and $n_1$ and $n_2$ are integers.

In some embodiments, the center of each feature is placed on a grid point of a 2-dimensional grid, e.g. a hexagonal, a rectangular or a square grid with predetermined grid constants.

In some embodiments, all features cover all grid points of such a grid, while in other embodiments not all grid points of the underlying grid are covered. For example, in some embodiments, in every other row of grid points, every other grid point may be covered by a feature. In yet other embodiments, in every second, third, fourth or higher order row, every second, third, fourth, or higher order grid point is left empty.

In some embodiments, the topographical structure may include a plurality of different features, e.g. a number of different features arranged in a regular, e.g. periodic, pattern, e.g. as alternating rows of two, three, or more different features. Examples of such patterns include structures comprising features with square cross-sections and features with circular cross-sections that are arranged in alternating rows.

In some embodiments, the features are arranged in lines and/or rows. In some embodiments, the features in each row have the same pitch distance, while in other embodiments the pitch distance may vary throughout a row and/or from row to row. Similarly, the row-to-row distance may be the same for all rows or vary from row to row. In some embodiments, some or all structures in a row may be rotated with respect to their respective neighbor(s) in the same row. In some embodiments, some or all structures in a row may be rotated with respect to their respective neighbor(s) in the neighboring row(s).

In some embodiments, the lateral dimension of the features in all lateral directions is between 1 µm and about 10 µm. Examples of such features include protrusions with generally square or circular cross sections. In other embodiments the lateral dimension of the features in one direction is between 1 µm and about 10 µm, while the lateral dimension in another direction is larger.

Examples of such features include elongated ridges, ribs, or wells. The side faces of the ridges may be substantially smooth or they may include additional features, e.g. a regular sequence of protrusions and/or recesses. Hence, in some embodiments such ridges may have an appearance that resembles a row of squares, circles or the like that are merged/interconnected with their respective neighbours to form an uninterrupted ridge.

In particular, in some embodiments the topographical structure comprises both features with lateral dimensions between 1 µm and about 10 µm in all lateral directions and features with lateral dimensions between 1 µm and about 10 µm in only one direction. Examples of such structures include rows of generally square-shaped and/or circular features where the rows are separated by elongated ridges.

Figure 26:
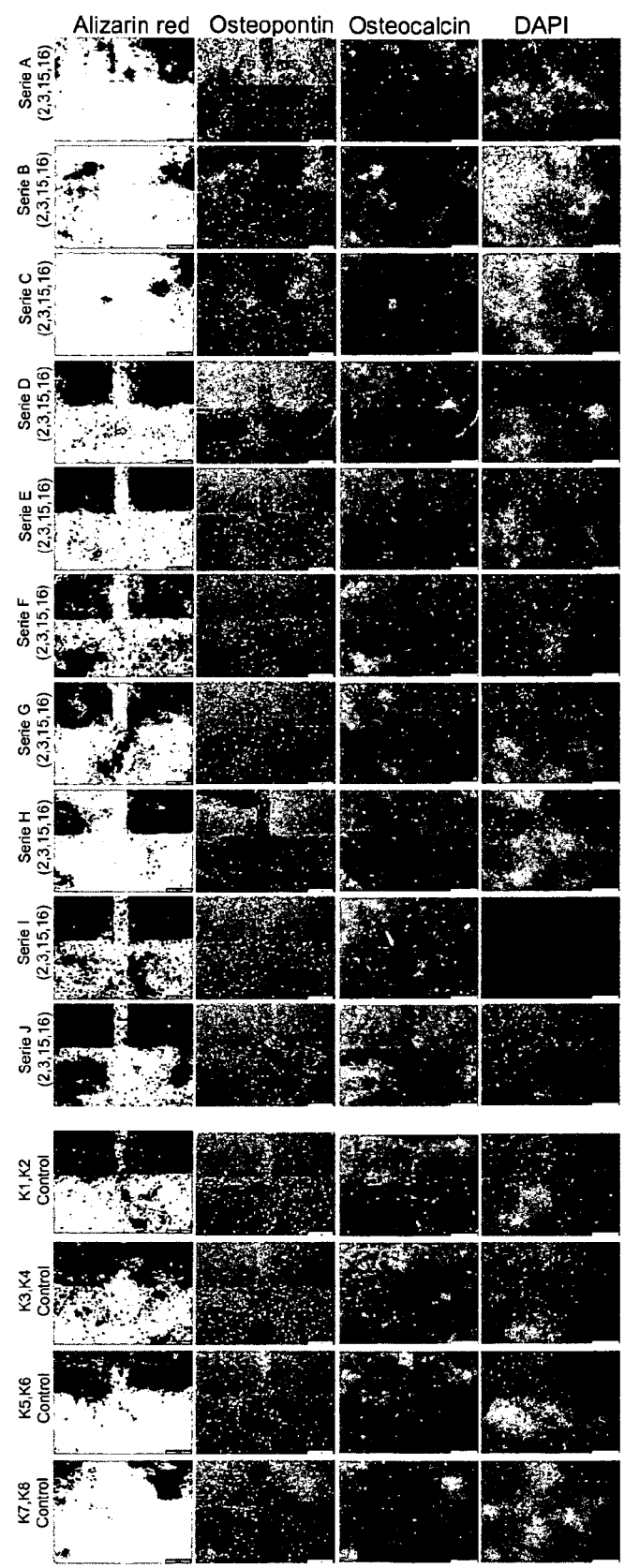
FIG. 26 shows the mineralization, expression of OPN, OC, and DAPI staining of MC3T3 cells after 2 weeks induction on BSSA wafers, where the wafer has surface structures Series A to J, K and a control, where the structure height dimension is Z=2.4 µm (as defined in FIG. 23). The images are an enlargement of an area encompassing the intersection between structures: (2, 3, 15 and 16 of Series A-J) and (1-8 of K 1-8 and control areas).

FIGS. 8 a-k show top views of examples of the topographical structures with features in the form of protrusions/pillars having a generally circular, square or rectangular cross-section. Each feature has a lateral diameter X in at least one direction, and the gap distance between features in adjacent rows and columns is denoted Y. In FIGS. 8 *a, c, e, f,* and *i,* Y is equal to the gap size between any feature and its nearest neighbor, corresponding to a pitch distance X+Y. In FIGS. 26 *b, d, g, h,* and *j,* the gap distance to the nearest neighbor is different for different features, as exemplified by features 1201, 1202, and 1203 of FIG. 26 *b*. Feature 1201 has feature 1202 as its nearest neighbor; consequently the gap size is Y. However, feature 1203 has features 1201 and 1202 as its nearest neighbors with a slightly different gap size d. Accordingly, in FIGS. 8 *b, d, g, h,* and *j,* the pitch distances are different from row to row. In the row including feature 1201, the pitch distance is X+Y, while the pitch distance in the row including feature 1203 is 2(X+Y).

In the examples of FIG. 8, the center of each feature is placed on a corresponding grid point of a 2-dimensional rectangular grid with grid constants a and b, as illustrated in FIGS. 8 *a* and *b*. However, in FIGS. 8 *a-e, h-i* not all of the grid points are actually covered by features, while in FIGS. 8 *f* and *k* all grid points are covered by features. In FIGS. 8 *a, c, e, f,* and *i*, the grid is a square grid with grid constant a=b=(X+Y). In FIGS. 8 *b, d, g, h,* and *j*, the grid is rectangular and the grid constants are a=X+Y and b=(X+Y)/2. In FIG. 8 *k*, the grid constants are a=2·X and b=3.5·X. For selected values of X and Y, wafers have been produced according to FIGS. 8 *a-h* where (X,Y) in µm were selected from (X,Y)=(1,1), (1,2), (1,4), (1,6), (2,1), (2,2), (2,4), (2,6), (4,1), (4,2), (4,4), (4,6), (6,1), (6,2), (6,4), (6,6). For selected values of X and Y, wafers have been produced according to FIG. 8 *k*, where X in µm was selected from X=1, 2, 3, 4, 5, 6, 7, 8. Accordingly, the grid constants a and b of the underlying grids were a=b=2-12 µm for the square grids of FIGS. 8 *a, c, e, f,* and *i*. For the rectangular grids of FIGS. 8 *b, d, g, h,* and *j*, the grid constants in direction a were in the interval between 2-12 µm, the grid constants in direction b were in the interval between 1-6 µm. For the grid of FIG. 8K, the grid constant b lies in the interval between 3.5-28 µm and grid constant a lies in the interval between 2-16 µm.

Figure 8A:
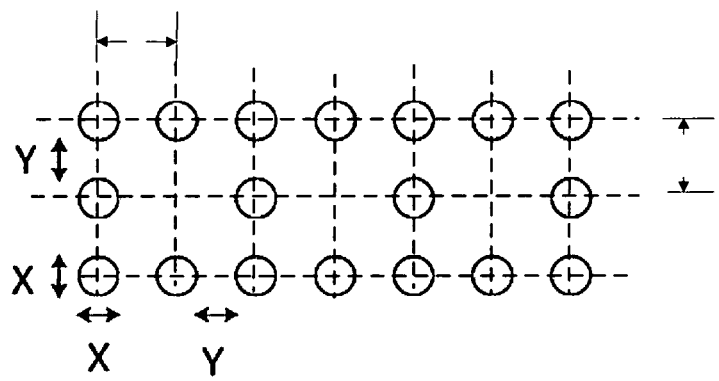
FIG. 8 shows a schematic top view of a topographical structure, where the center of each projection (pillar) is placed on a grid point of a 2-dimensional grid, e.g. a hexagonal, a rectangular or a square grid with predetermined grid constants, these structures being used to test for growth embryonic stem cells in an undifferentiated or differentiated mode.

For the purpose of identifying the above structures for different values of X and Y respectively, structures as shown in FIG. 8*a* are referred to as AX.Y in the present description, where X and Y refer to the dimensions X and Y described above. Hence, structure AX.Y includes protrusions/pillars having a circular cross-section of diameter X µm. The protrusions are arranged in parallel rows, where the gap size between adjacent protrusions in every second row is Y µm, while the gap size between protrusions in the remaining rows is (2Y+X) µm. The gap size between protrusions of adjacent rows is Y µm. The protrusions in adjacent rows are aligned with each other.

Figure 8B:
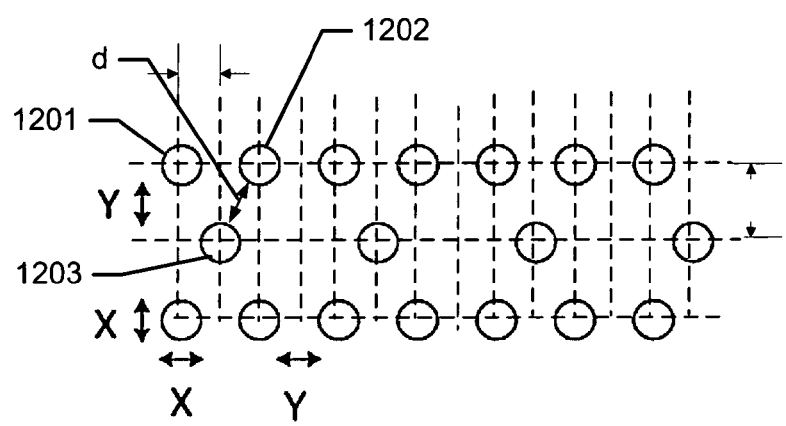

Similarly, structures as shown in FIG. 8*b* are referred to as BX.Y. Hence, structure BX.Y includes protrusions/pillars having a circular cross-section of diameter X µm. The protrusions are arranged in parallel rows, where the gap size between adjacent protrusions in every second row is Y µm, while the gap size between protrusions in the remaining rows is (2Y+X) µm. The gap size between protrusions of adjacent rows is Y µm. The protrusions in the rows having a gap size of (2Y+X) µm are aligned with the centre of the gaps between protrusions of their respective adjacent rows.

Figure 8C:
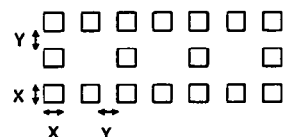

Structures as shown in FIG. 8*c* are referred to as CX.Y. Hence, structure CX.Y includes protrusions/pillars having a square cross-section of linear dimension of X µm. The protrusions are arranged in parallel rows, where the sides of the squares are aligned with the direction of the rows, and where the gap size between adjacent protrusions in every second row is Y µm, while the gap size between protrusions in the remaining rows is (2Y+X) µm. The gap size between protrusions of adjacent rows is Y µm. The protrusions in adjacent rows are aligned with each other.

Figure 8D:
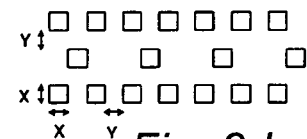

Structures as shown in FIG. 8*d* are referred to as DX.Y. Hence, structure DX.Y includes protrusions/pillars having a square cross-section of linear dimension of X µm. The protrusions are arranged in parallel rows, where the sides of the squares are aligned with the direction of the rows, and where the gap size between adjacent protrusions in every second row is Y µm, while the gap size between protrusions in the remaining rows is (2Y+X) µm. The gap size between protrusions of adjacent rows is Y µm. The protrusions in the rows having a gap size of (2Y+X) µm are aligned with the centre of the gaps between protrusions of their respective adjacent rows.

Figure 8E:
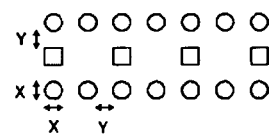

Structures as shown in FIG. 8*e* are referred to as EX.Y. Hence, structure EX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with circular protrusions is Y µm, while the gap size between the square protrusions in the remaining rows is (2Y+X) µm. The gap size between protrusions of adjacent rows is Y µm. The protrusions in adjacent rows are aligned with each other.

Figure 8G:
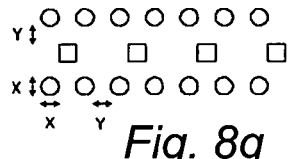
Figure 8F:
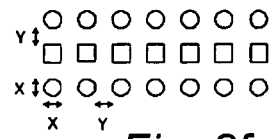

Structures as shown in FIG. 8*f* are referred to as FX.Y. Hence, structure FX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between protrusions within each row and between adjacent rows is Y µm. The protrusions in adjacent rows are aligned with each other.

Structures as shown in FIG. 8*g* are referred to as GX.Y. Hence, structure GX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with circular protrusions is Y µm, while the gap size between the square protrusions in the remaining rows is (2Y+X) µm. The gap size between protrusions of adjacent rows is Y µm. The square protrusions in the rows having a gap size of (2Y+X) µm are aligned with the centre of the gaps between the circular protrusions of their respective adjacent rows.

Figure 8H:
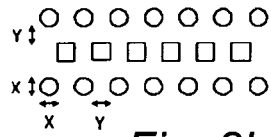

Structures as shown in FIG. 8*h* are referred to as HX.Y. Hence, structure HX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between protrusions within each row and between adjacent rows is Y µm. The protrusions in adjacent rows are aligned with each other. The square protrusions are aligned with the centre of the gaps between the circular protrusions of their respective adjacent rows.

Figure 8I:
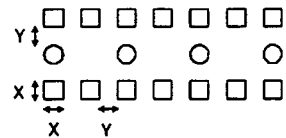

Structures as shown in FIG. 8i are referred to as IX.Y. Hence, structure IX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with square protrusions is Y µm, while the gap size between the circular protrusions in the remaining rows is (2Y+X) µm. The gap size between protrusions of adjacent rows is Y µm. The protrusions in adjacent rows are aligned with each other.

Figure 8J:
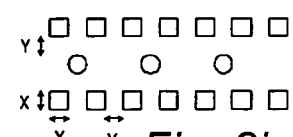

Structures as shown in FIG. 8j are referred to as JX.Y. Hence, structure JX.Y includes protrusions/pillars having a circular cross-section of diameter X µm as well as protrusions/pillars having a square cross-section of linear dimension of X µm. The protrusions are arranged in alternating parallel rows with circular protrusions in every second row, and square protrusions in the remaining rows. The gap size between adjacent protrusions in the rows with square protrusions is Y µm, while the gap size between the circular protrusions in the remaining rows is (2Y+X) µm. The gap size between protrusions of adjacent rows is Y µm. The circular protrusions in the rows having a gap size of (2Y+X) µm are aligned with the centre of the gaps between the square protrusions of their respective adjacent rows.

Hence, in the above examples, the minimum gap size between nearest-neighbor features is Y µm, and the minimum centre-to-centre distance between nearest-neighbour features is X+Y µm.

Figure 8K:
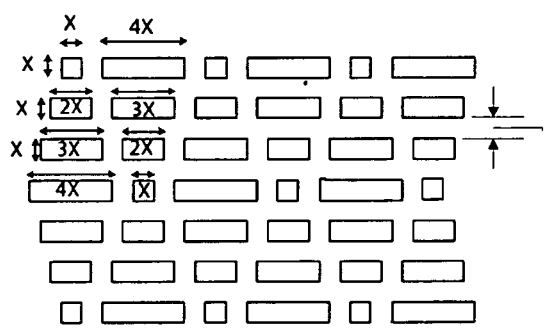

Structures as shown in FIG. 8k are referred to as KX. Structure KX comprises groups of elongated protrusions/ridges of rectangular cross section. The ridges have different lengths and are arranged parallel with each other. The ridges of each group are arranged to form a rectangular shape, such that each group includes a longest ridge as a central ridge. On each side of the central ridge are arranged a series of ridges becoming progressively shorter with increasing distance from the central ridge. The rectangular shape KX includes thus a sequence of ridges of lengths X µm, 2X µm, 3X µm, 4X µm, 3X µm, 2X µm, X µm. The width of the ridges is X µm. The distance between ridges is X µm. The groups of ridges are arranged in a predetermined pattern, such that the ridges are placed along rows, where each row includes ridges of two alternating lengths: A first type of rows includes alternating ridges of length X µm and 4 X µm. A second type of rows includes alternating ridges of length 2 X µm and 3 X µm. The overall pattern of ridges resembles a sharkskin structure.

The structure of the most preferred biocompatible surface of the invention is characterized by a nano- and/or micrometer scale topographical structure comprising a plurality of protrusions arranged on grid points of a regular two-dimensional grid, wherein the protrusions have a cross section with a minimum cross-sectional diameter 1.0 µm-2.0 µm, wherein the distance between adjacent grid points along at least one dimension is between 2.0 µm and 9.0 µm, wherein each of the protrusions of the topographical structure has a vertical height/depth dimension equal to or greater than 1.60 µm, preferably about 2.4 µm.

IV. An Implant Comprising the Biocompatible Material of the Invention

According to one aspect, the invention provides a medical implant for use in bone tissue implantation and the like, wherein at least a part of the surface of the implant is characterized by the biocompatible material of the invention, whose surface is characterized by a defined periodic micrometer scale topographical structure that is biocompatible with bone-forming cells, and whose topographical structure is described above under section II and in the examples. A medical implant of the invention includes a dental implant, an orthopedic prothesis/implant, a spinal implant, a bone substitute that may be contemplated for use in the treatment of a bone fracture, a degenerative disorder, trauma, and cancer.

In a preferred embodiment the entire exposed surface area of the implant, or the biocompatible coating for use in the manufacture of an implant, is composed on a biocompatible material of the invention having a topographical structure that enhances expression of osteopontin and osteocalcin in bone-forming cells. In an alternative embodiment, one or more parts of said exposed surface area is composed as a biocompatible material of the invention having a topographical structure that enhances expression of osteopontin and osteocalcin in bone-forming cells. Hence by selectively providing a device with a suitable surface structure, it may be controlled, which parts of the surface should perform in a certain fashion (e.g. mineralization). Other parts of the implant may be formed by other types of structures that could enhance the biocompatibility of e.g. chrondrocytes, epithelial cells where the implant is to be in contact with alternating types of tissue. A surface for rejection of bacteria growth may also be included. As an example a dental implant could be considered. This implant is to consist of 5 different surfaces in order to fulfill the requirements for alternating environments: 1. Optimal for expression of osteopontin and osteocalcin in bone-forming cells, 2. Optimal biocompatibility for connective tissue (fibroblasts), 3. Optimal biocompatibility for epithelium (epithelial cells), 4. Surface for bacterial rejection, and finally, 5. Optimal surface for the addition of an artificial tooth.

V. Method of Synthesizing a Biocompatible Topographically Modified Surface of the Invention Over a Contoured, 3D Surface of an Implant.

An implant surface that is biocompatible for bone-forming cells and enhances expression of osteopontin and osteocalcin in bone-forming cells, may be manufactured by a number of production techniques, e.g. one or more of the following techniques:

Die imprinting: By using hard molds (e.g. of SiC or SiN) it is possible to produce patterns directly in other hard materials, like implant metals, by imprinting. The die, which is the master, is typically produced by a combination of e-beam lithography and Reactive Ion Etching. It has been shown that large arrays of nanostructures with width down to 40 nm can be printed in soft metals like Aluminium (S. W. Pang, T. Tamamura, M. Nakao, A. Ozawa, H. Masuda, J. Vac. Sci. Technology B 16(3) (1998) 1145. More specifically, it is desirable to generate die patterns in very hard materials like SiC or SiN when pressing in other hard substrates like Al, Ti, Titanium alloys, stainless steels, Ta, etc—otherwise the die will be damaged or even destroyed. The die imprinting can of course also be applied in softer materials like polymers. Since materials like SiC or SiN are difficult to dry-etch it is desirable to create an etch-mask consisting of e.g. Cr instead of just a photoresist. The mask can be produced in the following way: The lateral pattern is created by e-beam lithography in a resist followed by development, typically in an organic solvent like acetate. This leaves a resist pattern on the surface. The resist pattern is covered by a PVD—deposition of an approximately 100 nm Cr layer and at last lift-off by dissolving the resist using a standard resist remover. Dry etch of the hard die material can be carried out in a Reactive Ion Etching system. The depth of the structure is controlled by ion etching time. At last the Cr mask can be removed in cerium nitrate aqueous solution. Now the hard die is ready for imprinting in the surface for synthesizing a biocompatible topographically modified surface. The die can press micro- and nano-patterns in selected areas of the biomaterial by hydraulically pressing the die into selected areas of the surface. The pressure applied will typically be several tonnes for 10-30 seconds. Several areas can be patterned by consecutively patterning areas of the die size. The die size is typically from 10×10 $mm^2$ up to 40×40 $mm^2$. This micro- and nano-printing method is highly suitable for patterning selected areas on a contoured 3D implant produced by e.g. Ti, Titanium alloys, tantalum, or stainless steels. But it can of course also be applied to less hard materials like polymeric materials/coatings.

Imprinting by rolling a die. The method is basically the same as die imprinting, however, here the die is not flat but typically a cylinder. This die-roller is micro- and nano-structured by photolithography or e-beam lithography/Reactive Ion etching as described for the die imprinting above. The setup needs to be modified in order to take into account the curved surface. The die-roller can now be pressed on and rolled over selected areas of the biomaterial by hydraulically pressing the roller-die onto the surface of the implant, thereby imprinting the micro and/or nanostructure. Also here, the implant material can be hard like Ti, Ti-alloys, tantalum or stainless steel, but it does not have to be, so the method is also applicable for e.g. polymers.

Patterning by colloidal lithography: Here, it is possible to nano-pattern surfaces by depositing colloidal particles (e.g. polystyrene or the protein ferritin), which assemble in a short-range ordered pattern. These particles can e.g. be used as: an etching mask making pillars, a topographical template for making protrusions on the surface, or deposition of e.g. a nanometer metal cluster (e.g. by the metallic center of ferritin).

Laser patterning by ultra-short laser pulses: This technique can be utilized for high-precision patterning. In particular, the strong non-linearity of the ablation process leads to a well-defined threshold for material removal, and this has been used to demonstrate the formation of structures even below the diffraction limit (P. P. Pronko, S. K. Dutta, J. Squier, J. V. Rudd, D. Du, G. Mourou: Optical Communication 114, (1995) 106).

The laser patterning by ultrashort laser pulses can also be used in combination with pre-deposition of quartz spheres (K. Vestentoft, J. A. Olesen, B. H. Christensen, P. Balling: Appl. Phys A 80, (2005) 493 to create large arrays of nano-meter-sized holes. More specifically, a layer of quartz spheres is deposited on the surface typically, but not necessarily, creating a densely packed array. By scanning an unfocused laser beam of ultra-short pulses across the surface with the quartz spheres, it is possible to generate large areas of structures in parallel, since the spheres act as individual lenses focusing the laser beam.

Laser scanning-beam Interference Lithography: This low-cost method can be used for fabricating periodic and quasi-periodic and spatially coherent patterns over large surface areas. The methods utilize the interference between two or more coherent planar wave-fronts. (S. Kuiper, H. van Wolferen, G. van Rijn, Journal of Micromechanics and Microengineering 11(1), (2001) 33.

VI. A Device for Culturing Tissue or Cells Including an Exposed Surface Having a Microscale Surface Structure FIG. 9 schematically shows a cross-sectional view of a tissue culture dish having an exposed surface with a microscale structure. The dish 301 comprises an upwardly open receptacle having a bottom 303 and sidewalls 302. In use, the upper surface 304 is exposed to the cell culture or tissue and thus provides a microenvironment for the culture. In embodiments of the invention, the exposed surface 304 has a microscale topographical structure that is selected to promote a predetermined cellular function as described herein. Such surfaces can be produced in large quantities in e.g. polymers like polystyrene, different types of polycaprolactones, Poly (methyl methacrylate, silicones including poly(dimethylsiloxane), poly(hydroxyethyl methacrylate), poly(ethyl methacrylate), poly(D,L-lactide-co-glycolide), polyethylene, polycarbonate, polyvinyl alcohols, hyaluronic acid-based polymers, poly(ethylene oxide), poly(butylene terephthalate), methacryloyloxyethyl phosphorylcholine, mr-I T85, mr-I 7030, poly(bis(trifluoroethoxy)phosphazenes, natural polymers including modified poly(saccharide)s, e.g., starch, cellulose, and chitosan, and mixtures and co-polymers of the above mentioned, e.g. from a suitable stamp or blueprint by hot embossing or by injection molding, or by any other suitable process known in the art and/or as described herein. The surface 304 may be the upper surface of the bottom 303 or an upper surface of a separate element, e.g. a disk, placed on top of the bottom 303 of the dish. The surface 304 may also be provided in the form of a separate tissue culture plastic that has been modified to display the selected structures or blueprint of these structures on the surface. For example, the separate tissue culture plastic may be removably inserted in the culture dish 301. In this respect the term tissue culture plastic is intended to include any polymers/metal coatings/ material that can be used to produce a surface that can be used for growth of cells in vitro in cell culture.

Example 1.2

Manufacture of a 13×13 BSSA Wafer Comprising 169 Tester Areas

A single-sided polished silicon wafer (4 inch) with a thickness of 525±25 μm provided a substratum for the manufacture of a biocompatible material. The wafer was an n-type wafer with a resistivity of 1-20 ohm cm. A micrometer-sized pattern was printed onto the polished side of the silicon wafer by standard photolithography and reactive ion etching in a $SF_6$/ $O_2$ discharge according to the following protocol:

7. The wafers were pre-etched with buffered hydrofluoric acid (BHF, BHF is a solution of concentrated HF (49%), water, and a buffering salt, $NH_4F$, in about the ratio 1:6:4) for 30 seconds and then dried under $N_2$ flow, and
8. the wafer was then spin-coated with a 1.5 μm thick layer of photoresist AZ5214, Hoechst Celanese Corporation, NJ, US (the chemical composition can be found at the Material Safety Data Sheet (MSDS) supplied by Hoechst Celanese Corporation). and pre-baked at around 90° C. for 120 seconds, and
9. the photoresist-coated wafer was exposed to UV light for 5 seconds in an EVC aligner, model AL6-2, through a suitable mask, allowed to develop for 50-60 seconds and then post-baked for 1 minute at 120° C., and
10. the photoresist-coated wafer was then patterned by briefly etching with BHF for approximately 30 sec., and then subjected to Reactive Ion Etching (RIE) at a rate of approximately 0.30 μm/minute, and the resist was stripped with acetone followed by RCA cleaning. The RCA cleaning procedure has three major steps used sequentially: Removal of insoluble organic contaminants with a 5:1:1 $H_2O:H_2O_2:NH_4OH$ solution (SC1). Removal of a thin silicon dioxide layer where metallic contaminants may have accumulated as a result of (I), using a diluted 50:1 $H_2O:HF$ solution. Removal of ionic and heavy metal atomic contaminants using a solution of 6:1:1 $H_2O:H_2O_2:HCl$ (SC2).

11. The patterned wafer was then passivated by dry oxidation with a 20 nm $SiO_2$ layer, thermally grown at 1000° C. for 15 minutes.
12. A 250 nm tantalum layer was deposited onto the surface of the patterned wafer by sputter deposition.

Figure 23A:
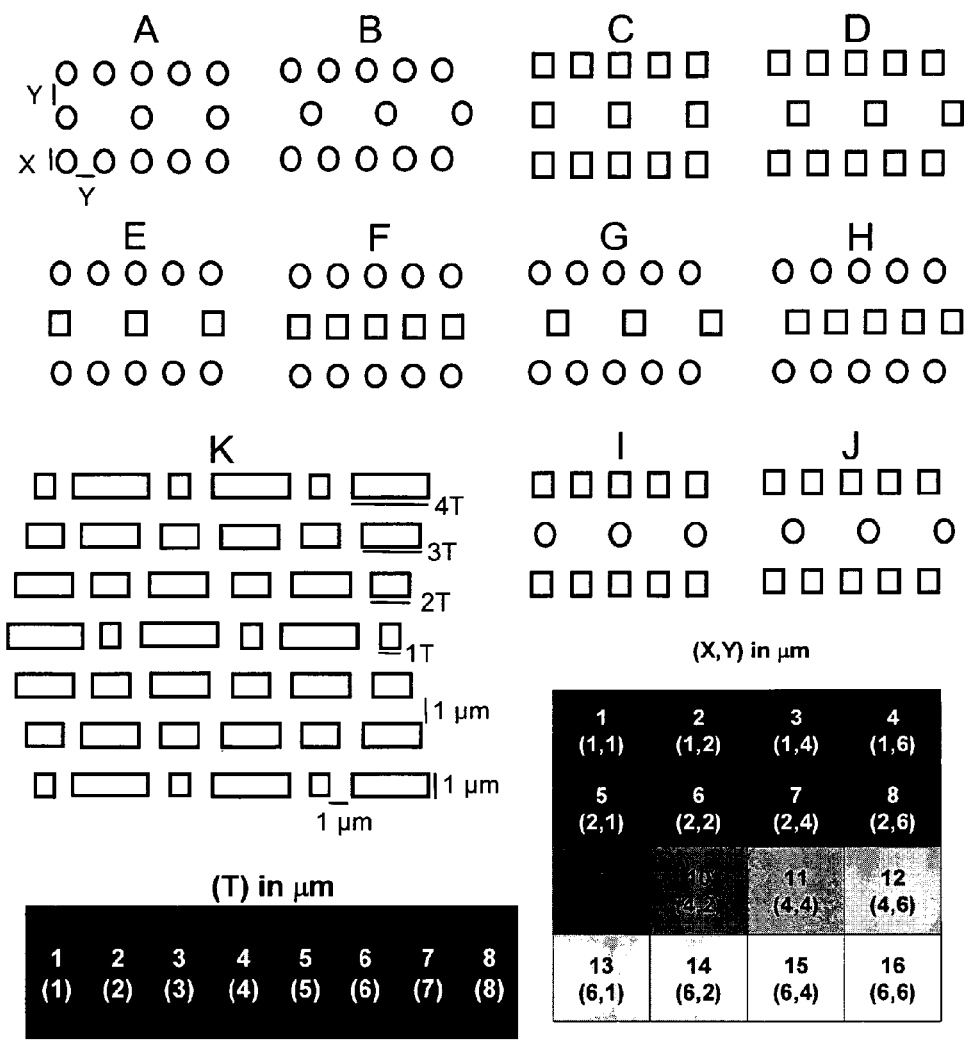
FIG. 23 shows the design of the wafer employed for mineralisation analyses:
A: Series A to J; Different iterations of squares and pillars. Each series contains 16 different combinations of lateral dimension of structures (X) in µm and gap between structures (Y) in µm. Series K; 8 different iterations of the lateral dimension of a "sharkskin" structure all with the same gap between the individual structures (1 µm).
B: Upper left illustration; Location of Series A to K on the wafer. White field in the middle of the wafer is the unstructured control field. Upper right and the two pictures in the middle; Induction of mineralization on three different vertical height dimensions of the structures (Z=0.6 µm, Z=1.6 µm and Z=2.4 µm) of the BSSA wafers described in A. Lower two pictures repetition of the above described experiment with two different heights (Z=1.6 µm and Z=2.4 µm). Note that structure 2 and 3 always are located above structure 15 and 16 for each series and that a small area of non-structured control surface separates each structure. MC3T3 cells were seeded on the BSSA wafers, induced to mineralize for three weeks and subsequently stained with Alizarin red for detection of mineralization (calcium).
C: Enlargement of selected section of the last two pictures in B. Upper three rows (Z=1.6 µm); Sections covering structure 2, 3, 15 and 16 with an unstructured control surface (cross) separating each structure (series A to J). Row 4 (Z=1.6 µm); K1,K2; K3,K4; K5,K6 and K7,K8 above unstructured surface at the edge of the BSSA wafer. Row 5 to 8 (Z=2.4 µm) same sections as for Z=1.6 µm. Note: Upper row consists of series A, C, E and I (structure features in every second row are located directly beneath every second structure in row 1); second row consists of series B, D, G and J (structure features in every second row are shifted 0.5×(gap+feature size) to the left; third row consist of series F and H (every structure features are located directly beneath each other.
D: Quantification of the relative degree of mineralization from the experiment with two wafers (Z=1.6 µm and Z=2.4 µm). All structures with the same size and gap from series A to J were pooled. All sizes of series K (T=1 to 8) were pooled.
Figure 23B:
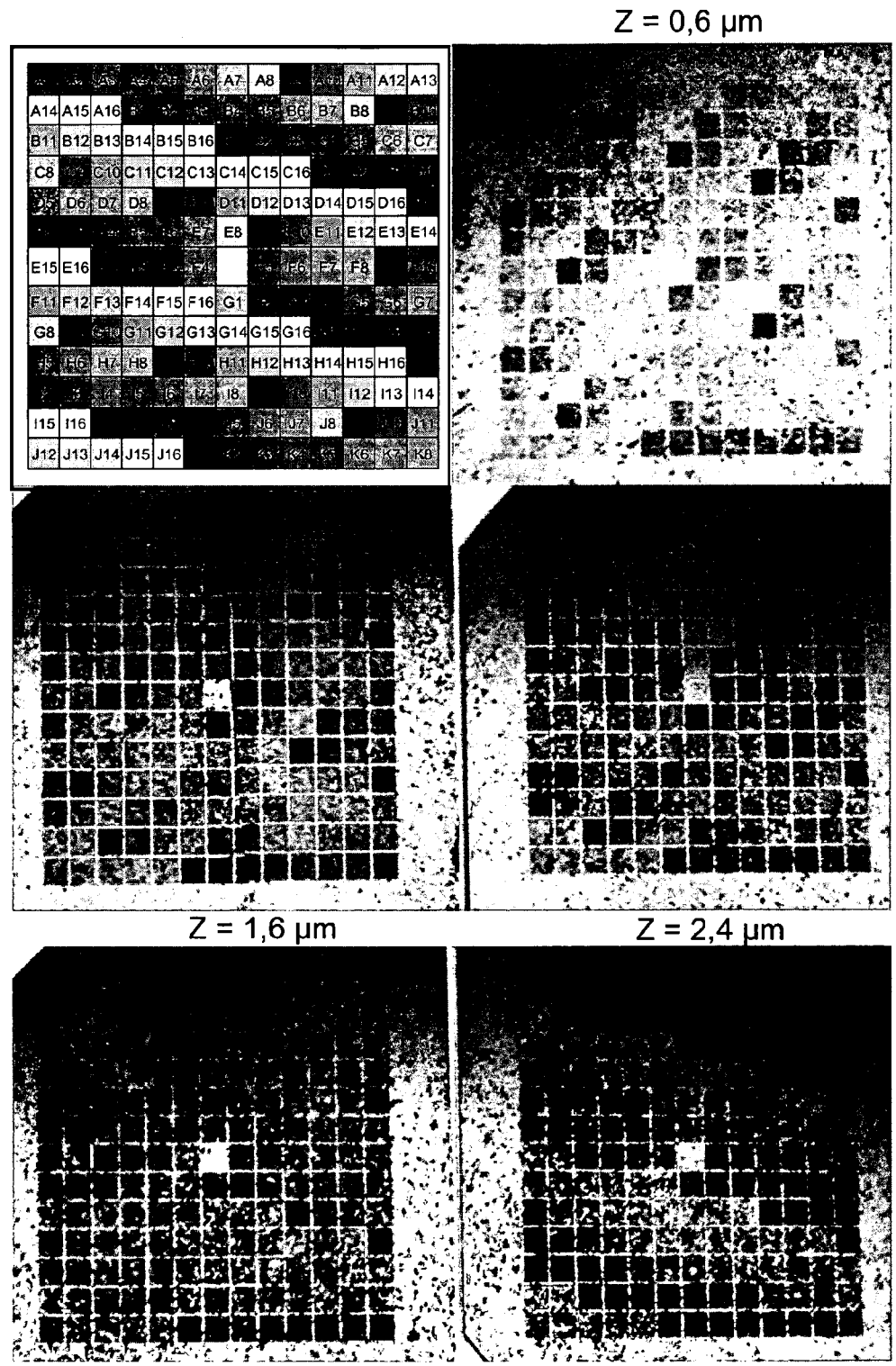
Figure 23C:
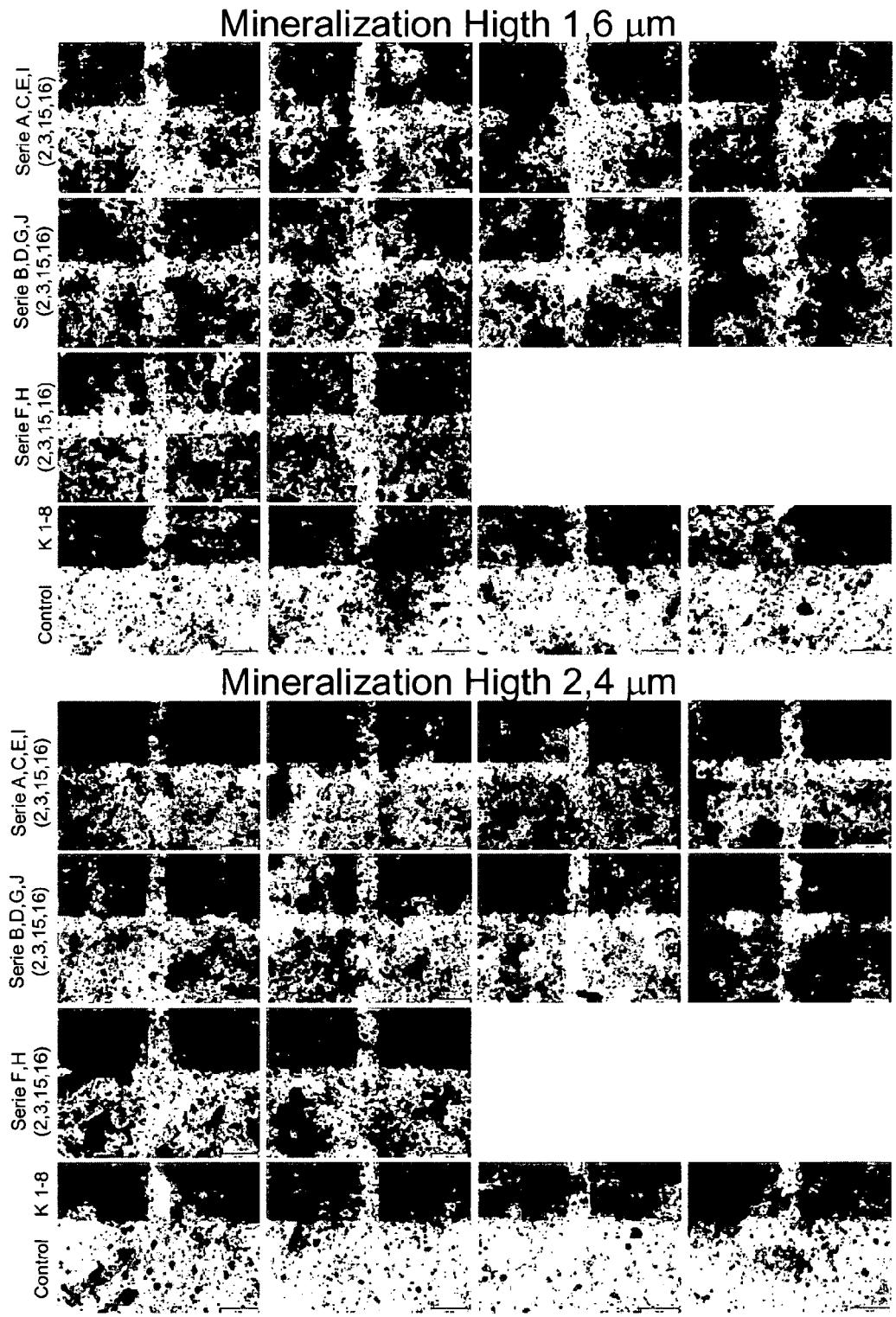
Figure 23D:
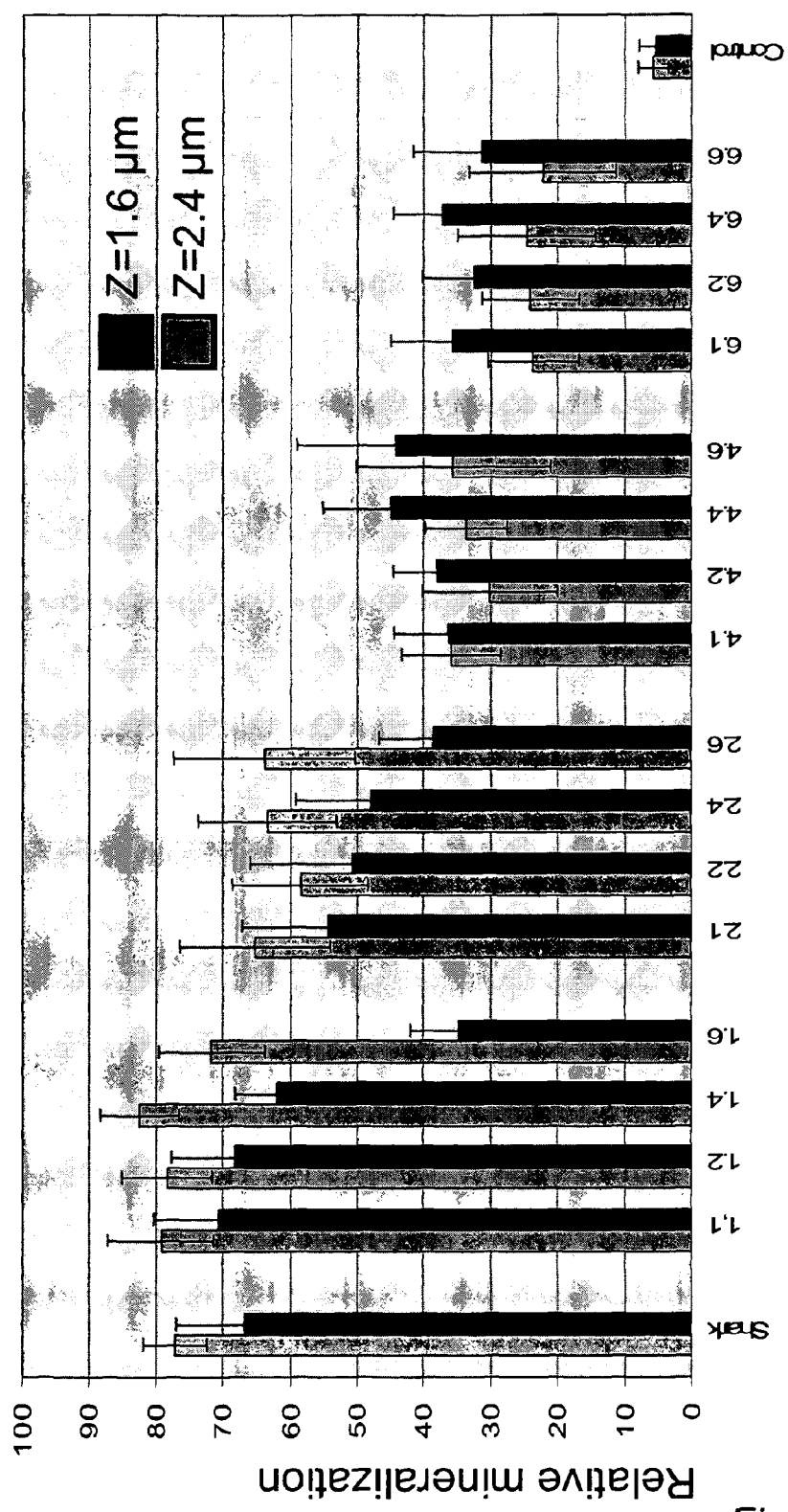

FIG. 23B shows a top view of one of the prepared wafers. The wafer, prepared according to Example 1.2, has 169 tester areas, wherein each tester area has one of 11 different lateral topographies A to K, comprising different iterations of projections having a cross-sectional shape that is either round, square or rectangular, as illustrated in FIG. 23A. Each of topologies A to J on the wafer are represented by a series 16 areas, each member of the series having a different combination of dimensions: (X) being the minimum lateral cross-sectional dimension of each projection, in μm, and (Y) being the gap between the projections in μm. Topology K is represented by 8 different iterations of the lateral dimension of a "sharkskin" structure where the gap between the individual structures is constant (1 μm). The location of the Series of topologies A to K on the wafer is shown in FIG. 23B. The central area of the wafer (blank square in FIG. 23B) has no structure, providing a control field. A series of wafers were produced according to these defined parameters, wherein the depth of the lateral topography was defined as either 0.60 μm, 1.60 μm or 2.40 μm.

In FIG. 23B, each tester area is labelled to indicate its topographical surface structure, where the dimensions of the 16 members of the series A-J is illustrated for topology A as follows:
"A1": Topology A where X=1 μm and Y=1 μm.
"A2": Topology A where X=1 μm and Y=2 μm.
"A3": Topology A where X=1 μm and Y=4 μm.
"A4": Topology A where X=1 μm and Y=6 μm.
"A5": Topology A where X=2 μm and Y=1 μm.
"A6": Topology A where X=2 μm and Y=2 μm.
"A7": Topology A where X=2 μm and Y=4 μm.
"A8": Topology A where X=2 μm and Y=6 μm.
"A9": Topology A where X=4 μm and Y=1 μm.
"A10": Topology A where X=4 μm and Y=2 μm.
"A11": Topology A where X=4 μm and Y=4 μm.
"A12": Topology A where X=4 μm and Y=6 μm.
"A13": Topology A where X=6 μm and Y=1 μm.
"A14": Topology A where X=6 μm and Y=2 μm.
"A15": Topology A where X=6 μm and Y=4 μm.
"A16": Topology A where X=6 μm and Y=6 μm.

The dimensions for T of the 8 members of the series K (sharkskin) are as follows:
"K1": Topology K where X=1 μm and T=1 μm
"K2": Topology K where X=1 μm and T=2 μm
"K1": Topology K where X=1 μm and T=3 μm
"K1": Topology K where X=1 μm and T=4 μm
"K1": Topology K where X=1 μm and T=5 μm
"K1": Topology K where X=1 μm and T=6 μm
"K1": Topology K where X=1 μm and T=7 μm
"K1": Topology K where X=1 μm and T=8 μm It is understood that the preparation method described above may also be applied to wafers with other forms and sizes of tester areas as well as other types of structures (see FIGS. 3-7). The same production process may be used for a variety of different wafers, where the layout of the tester areas and the particular surface structures are determined by the mask through which the wafer is exposed.

Example 2.2

Screening a BSSA Wafer Identifies a Biocompatible Material that Promotes Bone Formation by Expression of Osteopontin and Osteocalcin in Bone-Forming Cells Murine osteoblastic (MC3T3-E1) cells were seeded on silicon wafers having a library of surface topologies, as set out in FIG. 23, from which surfaces capable of promoting bone formation by expression of osteopontin and osteocalcin in bone-forming cells were identified.
Methodology:
BSSA wafers: were produced using standard photolithography and coated with tantalum as described in connection with example 1.2.
Osteoblastic cells line, cultivation and seeding protocol: Murine osteoblastic (MC3T3-E1) cells (RIKEN cell bank; Tokio, Japan; Sudo, H et al. 1983, *J Cell Biol* 96(1):191-98)) were maintained in Mem Alpha Medium without Ascorbic Acid (supplied by Gibco Invitrogen) supplemented with 10% Fetal Bovine Serum (Gibco), 100 u/ml penicillin and 100 μg/ml streptomycin (Gibco) at 37° C. in a humidified atmosphere of 95% air and 5% $CO_2$ and passaged every 4 days using standard techniques.

Prior to cell seeding the wafers were placed in a p10 Petri dish (Nunc), and sterilized by soaking in 70% ethanol for 15 min, rinsed twice with sterile water and dried inside a sterile hood. MC3T3-E1 cells were trypsinized, harvested and seeded onto the dishes containing wafers at a density of 1000 cells/cm² for determination of cell growth, 6000 cells/cm² for determination of cell area or 40,000 cells/cm² for osteogenic stimulation all in the same medium as above.

For cell growth determination cells were fixed and stained with 4',6-diamidino-2-phenylindole [DAPI] or immunoassayed after 4 h, 24 h, 48 h and 96 h. DAPI is a fluorescent stain that binds strongly to DNA, which can pass through intact cell membranes and thereby be used to stain both live and fixed cells. DAPI stained cells are detected by fluorescence microscopy, excited with ultraviolet light. When DAPI is bound to double-stranded DNA its absorption maximum is at 358 nm and its emission maximum is at 461 nm, which appears blue/cyan.

For cell area determination cells were fixed and immunoassayed after 24 h. For osteogenic stimulation, media was changed after 3 days to osteogenic media: regular media described above supplemented with 50 μg/ml ascorbic acid (Sigma) and 10 mM β-glycerophosphate (Sigma) The osteogenic media were changed twice a week until fixation and staining at 14 or 21 days.

Immunodetection protocol: Cells were gently rinsed with phosphate-buffered saline (PBS) and fixed in 4% Para formaldehyde/PBS for 15 min. After permeabilization in 0.1% Triton X 100 in PBS (T-PBS) for 10 min and incubation with 2% BSA in T-PBS for 2 hours the cells were reacted with primary antibodies for 2 hours. The cells were then washed 3 times in T-PBS followed by addition of the secondary antibodies, for 1 hour. Simultaneously DAPI (4,6-diamidino-2-phenylindole) (Sigma) was added for nuclear staining and rhodamine-labelled Phalloidin (p1951 Sigma) for staining of actin fibers. After 3 times wash in T-PBS the wafers were analyzed by automated fluorescence microscopy.

Primary antibodies employed to detect protein expression include: anti-osteopontin (AKM 2A1, mouse monoclonal IgG, Santa Cruz Biotechnology), anti-osteocalcin (FL-95, rabbit polyclonal IgG, Santa Cruz Biotechnology) both diluted 1:400 in T-PBS and Monoclonal anti-vinculin (Clone hVIN-1 mouse Ascites fluid, Sigma) diluted 1:800 in T-PBS Secondary antibodies; Alexa Flour 488-Goat Anti Mouse IgG (1:400 in T-PBS) (Molecular Probes, Invitrogen) and Rhodamine (TRITC)-conjugated Donkey Anti Rabbit (1:200) (Jackson ImmunoResearch)

In vitro Mineralization detection protocol: The mineralization/calcium deposition on the wafers was quantified by Alizarin Red staining either immediately after harvesting the cells or after the immunodetection procedure (to insure that a precise correlation between the immunostained cells and calcium deposition).

When the cells were immediately staining with Alizarin Red, the cells were fixed with ice-cold 70% ethanol for 1 hour and washed twice with $ddH_2O$ prior to addition of 40 mM Alizarin Red solution (Sigma A3757) for 10 min. After several washes in $ddH_2O$, the cells were incubated for 15 min in PBS and air dried in a fume hood. The stained area was analyzed and quantified using the automated fluorescence microscope using Leica Qwin software.

When staining with Alizarin Red after immunodetection, the immunostained cells were washed twice with $ddH_2O$ before adding the Alizarin Red solution. Otherwise the procedure was the same as above.

Results:

A. Structural Properties of a Biocompatible Surface Topology that Promotes Mineralisation by Osteoblastic Cells:

Mc3T3 cells were seeded upon a BSSA wafer, as defined in example 1.2 and FIG. 23, and grown as set out above. From FIG. 23B to D it can be seen that the vertical dimension of the structures (projections) has effects on mineralization, where the structures having the largest height promote the largest degree of mineralization $Z=2.4$ μm>$Z=1.6$ μm>$Z=0.6$ μm. There are no major differences between the individual series (A to J) stressing that the form of the structures and whether there was small systematic gaps between the structures is of lesser importance in promoting mineralisation. By pooling all the series with the same X and Y values it can be seen from FIG. 23D that structures having smaller X and Y values promote more mineralization, whereby, for all sizes of the structures tested, 1 μm>2 μm>4 μm>6 μm>>unstructured surface. All of the sharkskin structures have a gap size of 1 μm and a structure size of varying T-values where one cross-sectional diameter always has a length of 1 μm and the length of the other cross-sectional diameter is variable. The sharkskin structures all promoter mineralization as well as the best structures from series A-J. Note that a gap (Y) of 1 μm and size of structures (X) of 1 μm is among the dimensions identified by series A to J as being optimal for mineralization.

Figure 24:
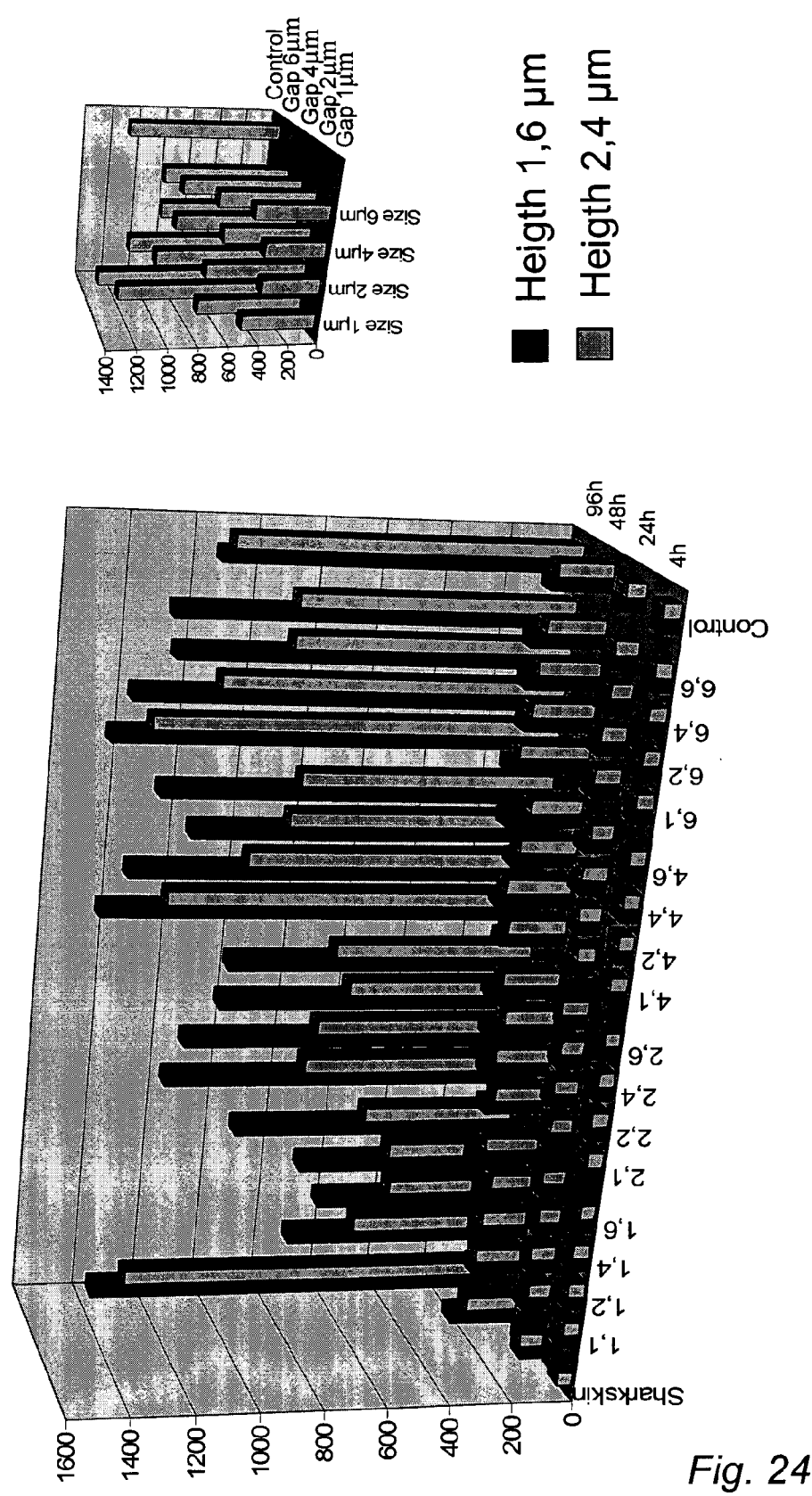
FIG. 24 shows the proliferation of MC3T3 cells seeded on BSSA wafers having surface structure projections of varying height/depth, as defined in FIG. 23):
Left panel: Representation of cell number (Z axis) where the height/depth dimension of the projections, Z=1.6 µm (dark shade) and Z=2.4 µm (light shade) for all time points after seeding and for all structures on the wafer.
Right panel: Cell number (Z axis) at 96 hours after seeding as a function of size (X axis) and Gap (Y axis) for Z=2.4 µm (light shade). All data with the same X and Y values from series A-J were pooled. The control data in both panels corresponds to cell growth on an area of the wafer having a flat surface.

B. Structural Properties of a Biocompatible Surface Topology that Promote Proliferation of Osteoblastic Cells:

Mc3T3 cells were seeded upon a BSSA wafer, as defined in example 1.2 and FIG. 23, and grown as set out above. Proliferation of osteoblastic cells on the BSSA wafer was calculated by counting the number of DAPI stained cells 4, 24, 48 and 96 hours after seeding. As seen in FIG. 24, cell proliferation decreased with the height of the projections $Z=2.4$ μm<$Z=1.6$ μm, whereas the height of the projections did not effect the ability of the cells to attach to the surface of the BSSA wafer (data from 4 hours). For the X and Y dimensions a combination of a Gap size (Y) between 1 and 4 μm and a size of the structures of $X=1$ μm results in the most pronounced decrease in proliferation rate. The negative effect of increasing surface topology height (Z) on cell proliferation is thus inversely correlated with its positive effect on mineralization (FIG. 23). By contrast, an increase in height of the Sharkskin structures did not induce a decrease cell proliferation rate.

C. Structural Properties of a Biocompatible Surface Topology that Promote Bone Formation by Expression of Osteopontin and Osteocalcin in Bone-Forming Cells:

Mc3T3 cells were seeded upon a BSSA wafer, as defined in example 1.2, of vertical dimension of $Z=2.4$ μm and induced to mineralize for two or three weeks. The cells were subsequently fixed and stained for OPN (green), OC (red) and DAPI (blue). Following fluorescence microscopy detection of OPN, OC and DAPI, the wafers were stained with Alizian red.

Figure 25:
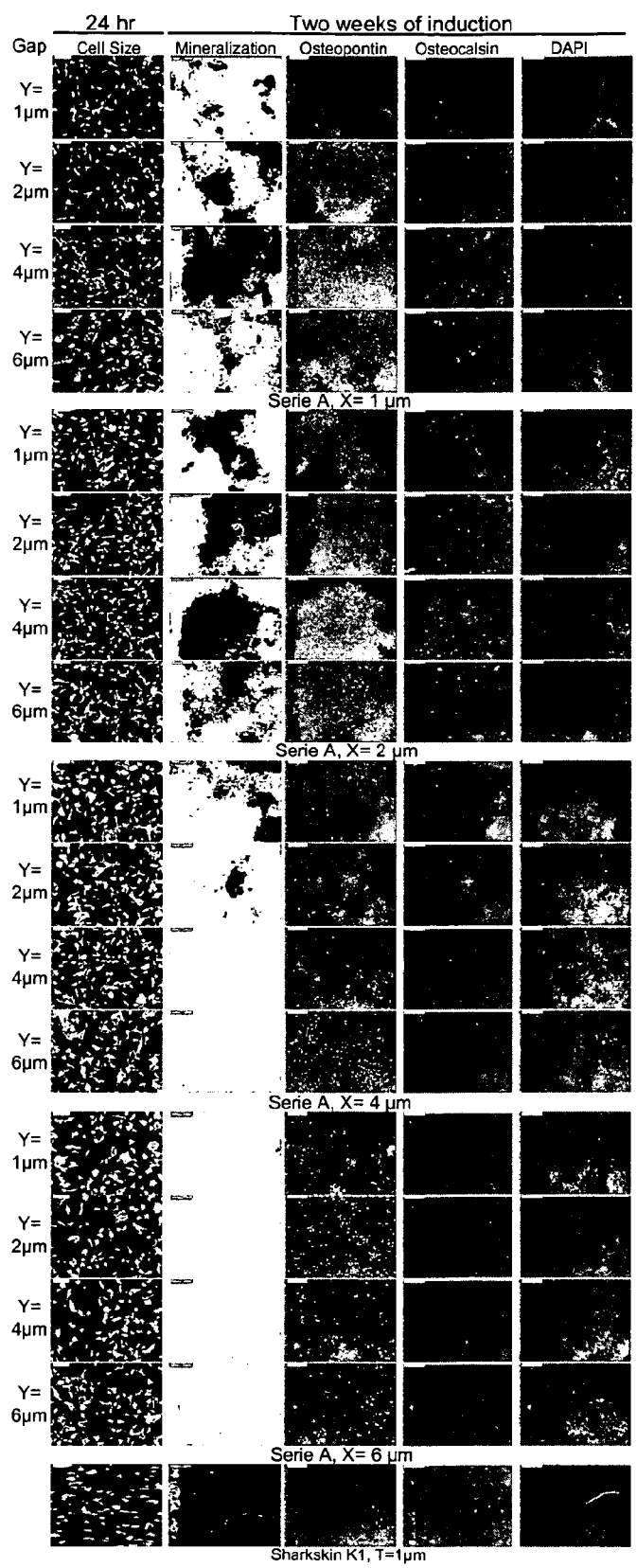
FIG. 25 shows the cell size, mineralization and expression of OPN and OC of MC3T3 cells seeded on BSSA wafers having Series A, K or control surface structures having a vertical dimension of Z=2.4 µm, (as defined in FIG. 23).
Vertical panel row 1: shows cells on the wafer, detected by Actin and Vinculin overlay staining (10×)
Vertical panel row 2 to 5: shows MC3T3 cells after being seeded on a BSSA wafer; grown for two weeks; and subsequently fixed and stained for Osteopontin (OPN, green), Osteocalcin (OC, red) and DAPI (blue). Following fluorescence microscopy detection of OPN, OC and DAPI staining, the wafer was stained with Alizarin red (vertical panel row 2). Horizontal panel rows 1 to 4 have a feature size of X=1 µm and gaps (Y) between 1, 2, 4 and 6 µm respectively. Horizontal panel row 5 to 8 have a feature size of X=2 µm and gaps (Y) between 1, 2, 4 and 6 µm respectively. Horizontal panel row 9 to 12 have a feature size of X=4 µm and gaps (Y) between 1, 2, 4 and 6 µm respectively. Horizontal panel row 13 to 16 have a feature size of X=6 µm and gaps (Y) between 1, 2, 4 and 6 µm respectively. Horizontal panel row 17 and 18 have a sharkskin structure K1 (T=1 µm) and non-structured surface, respectively. Panel 2 to 5: All images include an unstructured part of the BSSA wafer separating the different structures (⅕ left part of each picture).

Mean cell area was determined 24 hours after cell seeding (FIGS. 25 and 27). Mineralization was determined after 2 (FIGS. 25 and 26) or 3 weeks (FIG. 28) of osteogenic induction. The induction of OPN and OC is positively correlated with mineralization which is inversely correlated with cell size (for the small x values: $X=1$ and $X=2$): Thus, the smaller X and Y values of the projections on the BSSA wafer, the greater the induction of OPN and OC, and the greater the degree of mineralization, and the smaller cell size; Thus for Mineralization, OPN, OC: 1 μm>2 μm>4 μm>6 μm>>unstructured surface. For the larger X values another decrease in cell size with increasing Y values is observed (e.g. 6,6) This decrease in cell size for the large X and Y values does not correlate with mineralization, OC and OPN.

All of the series K sharkskin structures induced mineralization, and expression of OPN and OC, and cell size to the same extent as the best structures from Series A-J.

Summary:

The example provides a systematic analysis of BSSA structural surface libraries comprising a plurality of protrusions arranged on grid points of a regular two-dimensional grid, comprising different combinations of minimum cross-sectional diameter of the protrusions (X), gap between nearest protrusions (Y) and height of protrusions (Z) on the properties of osteoblastic cells. The data reveals that a height of 2.4 μm>1.6 μm>0.6 μm>flat unstructured surface is better in inducing mineralization. This correlates with proliferation where 2.4 μm<1.6 μm<flat unstructured surface. Regarding the X and Y values: the smaller X and Y values the greater the induction of OPN and OC, the better mineralization, the fewer cells and the smaller cell size; 1 μm>2 μm>4 μm>6 μm>>unstructured surface.

All of the sharkskin structures have a gap size (Y) of 1 μm and a structure size (X) where one side always has a dimension of 1 μm and the other side are variable. The mineralization, induction of OPN and OC, cell number and cell size is similar to the best structures from series A-J.

The combined data provides the basis for finding that a biocompatible material characterized by a topographical structure comprising a plurality of protrusions arranged on grid points of a regular two-dimensional grid, wherein the protrusions have a cross section with a minimum cross-sectional diameter 1.0 μm-2.0 μm, wherein the distance between adjacent grid points along at least one dimension is between 2.0 μm and 8.0 μm, wherein each of the protrusions of the topographical structure has a vertical height/depth dimension equal to or greater than 1.60 μm, preferably about 2.4 μm is one which will specifically promote bone formation by expression of osteopontin and osteocalcin in bone-forming cells.

Example 3.2

Ectopic Bone Formation

Ectopic bone formation may be analyzed as follows: 500,000 MC3T3-E1 cells per cm$^2$ are cultured on the 6 mm×6 mm biocompatible material structure (e.g. any of K series 1-8), in plain medium including added 50 microgram/ml ascorbic acid and 10 mM beta-glycerophosphate. After one week in culture, the biocompatible material structures are transferred to the subcutaneous mouse model for ectopic bone formation. Two pouches are made subcutaneously on the dorsal surface of the mice. During surgery the animals are anesthetized with isofluorane and one structure is put into each pouch, which are closed using surgical sewing. The mice are left for 8 weeks before they are killed by cervical dislocation. The structures are removed, plastic embedded in poly-methylmethacrylate (PMMA), cut, and stained for bone detection (e.g. basic fuchsin/light green or Alizarin Red S).

Example 4.2

Bone-Forming Assay in Sheep

An in vivo sheep model as described below can be used to assay the ability of the biocompatible material to induce bone formation/ingrowth:

Samples of the relevant biocompatible material and controls, e.g. flat tantalum, are produced on the base of 6 mm×6 mm silicon wafer squares. The samples are named "active" and "control", respectively, and are used in pairs to reduce the variation of the results due to animal variations The samples are glued on sample holders, by a biocompatible glue (e.g. Loctite 431) creating an implant.

The sample holder for use in a bone-forming assay in sheep is illustrated in FIG. 29. In particular, FIG. 29*a* shows a bottom view of the sample holder, FIG. 28*b* shows a side view of the sample holder, FIG. 29*c* shows a top view of the sample holder, FIG. 29*d* shows a perspective view of the sample holder, and FIG. 29*e* shows a cross-sectional view of the sample holder. The sample holder comprises a square recess 1501 adapted to receive the sample whose biocompatible surface is to be exposed. The square recess is located in the bottom surface of a cylindrical member 1502. In the top surface the sample holder comprises a threaded hole 1503 facilitating placement and removal of the sample holder in/from the bone.

Before surgery the sheep are given 2.5 ml Rompun vet. and 2 ml. Atropin. After 20 min. the animals are anesthetized with 15 ml. Propofol. In each medial femoral condyl one hole is drilled with depth 6 mm and diameter 11 mm. This leaves 0.5 mm gap between the biocompatible surface and the bone for examination of the bone ingrowth. The implants are press-fitted into the hole and the cut is closed by surgical sewing. The sheep are left for four weeks after which they are sacrificed. The implants are removed and embedded in poly-methylmethacrylate (PMMA). The degree of bone ingrowth is initially examined by μCT-scanning followed by cutting and standard histological examination of bone volume and bone ingrowth towards the implant.

The invention claimed is:

1. A cell or tissue culture container for promoting undifferentiated cell growth of undifferentiated pluripotent mammalian embryonic stem cells, the container having a surface for exposure to a culture during use, where at least a part of the surface comprises a biocompatible material, wherein at least a part of an exposed face of the biocompatible material has a nano- and/or micrometer scale topographical structure comprising a plurality of protrusions arranged on grid points of a regular two-dimensional grid, wherein the cross-sectional dimensions of the protrusions occupy an area equal to or less than 25% of the total area of the structure, said area being measured in the plane of the exposed face of the structure, and wherein the density of protrusions is equal to or greater than 1 protrusions per 65 μm$^2$, and wherein each of the protrusions of said topographical structure has a vertical height/depth dimension of about 2.4 μm and the maximum gap between any protrusions and its nearest neighbor (d;Y) is between about 2 μm-6 μm.

2. The cell or tissue culture container according to claim 1, wherein the protrusions have a cross section and a minimum cross-sectional diameter of between 0.1 μm and 4.0 μm and wherein the lateral dimension of the maximum gap between any protrusion and its nearest neighbor (d;Y) is between about 0.5 μm-8.0 μm.

3. The cell or tissue culture container according to claim 2, wherein the cross-sectional diameter is between 0.5 μm and 1.5 μm and the lateral dimension of the maximum gap between any protrusion and its nearest neighbor (d;Y) is between about 1 μm-4 μm.

4. The cell or tissue culture container according to claim 1, wherein the minimum distance between adjacent grid points along at least one dimension is between 0.5 μm and 8.0 μm.

5. The cell or tissue culture container according to claim 1, wherein the structure includes protrusions having the same cross-sectional geometrical shape or at least two different cross-sectional geometrical shapes.

6. The cell or tissue culture container according to claim 1, wherein the protrusions of different cross sectional geometry are arranged on the regular two-dimensional grid in an alternating pattern.

7. The cell or tissue culture container according to claim 1, wherein the structure includes protrusions of different cross-sectional area.

8. The cell or tissue culture container according to claim 1, wherein the lateral cross-section of the protrusions have a shape defined by circumference and/or geometry selected from circular, concave, round, star, square, rectangular, hexagonal, polygonal or a combination thereof.

9. The cell or tissue culture container according to claim 1, wherein at least a part of said surface is coated with a material selected from tantalum, titanium, platinum or an oxide thereof.

10. The cell or tissue culture container according to claim 1, wherein at least a part of said surface comprises a polymer selected from polystyrene, polycaprolactone polylactic acid, poly(lactic-co-glycolic) acid, chitosan or a combination thereof.

11. The cell or tissue culture container according to claim 1, further comprising a compound selected from the group consisting of: polypeptide, carbohydrate, growth hormone, antibody, antigen, glycoprotein, lipoprotein, DNA, RNA, polysaccharide, lipid, organic compound, and inorganic compound, wherein said organic or inorganic compound is adsorbed or chemically linked to the exposed surface of the container.

12. The cell or tissue culture container according to claim 11, wherein said growth hormone is selected from the group consisting of BMP, EGF, TGF-beta, IGF and LIF.

13. The cell or tissue culture container according to claim 1, wherein the cell or tissue culture container is chemically functionalized by nanocrystalline diamond, plasma polymerization, oxygen plasma, or nitrogen plasma.

14. A stamp or mask for the production of a cell or tissue culture container, the container being at least partially produced from a biocompatible material, the stamp being adapted to imprint or impart a topographical surface structure as defined in claim 1 into a surface of said biocompatible material.

15. A method of promoting undifferentiated cell growth of undifferentiated pluripotent embryonic stem cells, the method comprising bringing the cells into contact with a cell or tissue container having a surface for exposure to the stem cells, where at least a part of the surface comprises a biocompatible material, wherein at least a part of an exposed face of the biocompatible material has a nano- and/or micrometer scale topographical structure comprising a plurality of protrusions arranged on grid points of a regular two-dimensional grid, where the structure is selected to promote growth of undifferentiated mammalian embryonic stem cells, wherein the cross-sectional dimensions of the protrusions occupy an area equal to or less than 25% of the total area of the structure, said area being measured in the plane of the exposed faced of the structure, and wherein the density of protrusions is equal to or greater than 1 protrusions per 65 µm$^2$, and wherein each of the protrusions of said topographical structure has a vertical height/depth dimension equal to or greater than 1.6 µm or 3.0 µm and the maximum gap between any protrusion and its nearest neighbor (d;Y) is between about 2 µm-6 µm.

16. The method according to claim 15, wherein the protrusions have a cross section and a minimum cross-sectional diameter of between 0.1 µm and 4.0 µm and wherein the lateral dimension of the gap between any protrusion and its nearest neighbor (d;Y) is between about 0.5 µm-8.0 µm.

17. The method according to claim 16, wherein the cross-sectional diameter is between 0.5 µm and 1.5 µm and the lateral dimension of the maximum gap between any protrusion and its nearest neighbor (d:Y) is between about 1 µm-4 µm.

18. The method according to claim 15, wherein the minimum distance between adjacent grid points along at least one dimension is between 0.5 µm and 8.0 µm.

19. The method according to claim 15, wherein the structure comprises protrusions of at least two different cross-sectional geometrical shapes.

20. The method according to claim 19, wherein the protrusions of different cross sectional geometry are arranged on the regular two-dimensional grid in an alternating pattern.

21. The method according to claim 15, wherein the structure comprises protrusions of different cross-sectional area.

22. The method according to claim 15, wherein the lateral cross-section of one or more feature(s) has a shape defined by circumference and/or geometry selected from circular, round, star, square, rectangular, hexagonal, polygonal or a combination thereof.

23. The method according to claim 15, wherein at least a part of said surface is tantalum-coated and/or titanium-coated.

24. The method according to claim 15, wherein at least a part of said surface consists of a polymer selected from polystyrene, polycaprolactone polylactic acid, or chitosan.

25. The method according to claim 15, further comprising a compound selected from the group consisting of polypeptide, carbohydrate, growth hormone, antibody, antigen, glycoprotein, lipoprotein, DNA, RNA, polysaccharide, lipid, organic compound, and inorganic compound, wherein said organic or inorganic compound is adsorbed or chemically linked, immobilized or complexed with the surface layer of the container.

26. The method according to claim 25, wherein said growth hormone is selected from BMP, EGF, TGF-beta, IGF, LIF, or a combination thereof.

27. The method according to claim 15, wherein the cell or tissue culture container is chemically functionalized by nanocrystalline diamond, plasma polymerization, oxygen plasma, or nitrogen plasma.

28. The method according to claim 15, wherein said cells express a pluripotency marker selected from Oct4, Nanog, SSEA3/4, and SOX2.

29. A method for promoting uniform differentiated growth of mammalian cells, the method comprising bringing the mammalian cells into contact with a cell or tissue culture container having a surface for exposure to the stem cells, where at least a part of the surface comprises a biocompatible material, wherein at least a part of an exposed face of the biocompatible material has a nano- and/or micrometer scale topographical structure comprising a plurality of protrusions arranged on grid points of a regular two-dimensional grid, wherein the protrusions have a cross section and a cross-sectional diameter grid, wherein the protrusions have a cross section and a cross-sectional diameter of between 1.0 µm-8.0 µm and wherein the lateral dimension of the maximum gap between any protrusion and its nearest neighbor (d;Y) is between 1.0 µm-2.0 µm, and wherein the vertical height/depth dimension of each of the protrusions is equal to or less than 1.0 µm.

30. The method according to claim 29, wherein the lateral cross-section of one or more projection(s) has a shape defined by circumference and/or geometry selected from circular, round, star, square, rectangular, hexagonal, polygonal or a combination thereof.

31. The method according to claim 30, wherein the structure comprises projections having a square lateral cross-section and projections having a rectangular lateral cross-section, wherein a first cross-sectional diameter of the projections is 1.0 µm, and a second cross-sectional diameter of the projections is 1.0 µm-8.0 µm and wherein the vertical height/depth dimension of the projections is equal to or less than 1.0 µm.

32. The method according to claim 29, wherein at least a part of said surface is tantalum-coated and/or titanium-coated.

33. The method according to claim 29, wherein at least a part of said surface consists of a polymer selected from polystyrene, polycaprolactone polylactic acid, or chitosan.

34. The method according to claim 29, further comprising a compound selected from the group consisting of polypeptide, carbohydrate, growth hormone, antibody, antigen, glycoprotein, lipoprotein, DNA, RNA, polysaccharide, lipid organic compound, and inorganic compound, where said organic or inorganic compound is adsorbed to the exposed surface of the container.

35. A medical implant for use in bone-tissue implantation, the medical implant comprising a surface, where at least a part of the surface comprises a biocompatible material, wherein at least a part of a surface of the biocompatible material comprises a nano- and/or micrometer scale topographical structure comprising a plurality of protrusions arranged on grid points of a regular two-dimensional grid, where the structure is capable of promoting bone formation by expression of osteopontin and osteocalcin in bone-forming cells, wherein the protrusions have a cross section with a minimum cross-sectional diameter 1.0 µm-2.0 µm, wherein the distance between adjacent grid points along at least one dimension is between 2.0 µm and 9.0 µm, wherein each of the protrusions of the topographical structure has a vertical height/depth dimension equal to or greater than 1.60 µm.

36. The medical implant according to claim 35, wherein the lateral dimension of the maximum gap between any protrusion and its nearest neighbor (d;Y) is between about 1.0 µm-6.0 µm.

37. The medical implant according to claim 35, wherein the cross-sectional diameter of the cross section is about 1 µm and the lateral dimension of the minimum gap between any protrusions and its nearest neighbor (d;Y) is about 1.0 µm.

38. The medical implant according to claim 35, wherein the structure comprises protrusions of at least two different cross-sectional geometrical shapes.

39. The medical implant according to claim 38, wherein the protrusions of different cross sectional geometry are arranged on the regular two-dimensional grid in an alternating pattern.

40. The medical implant according to claim 35, wherein the structure comprises protrusions of different cross-sectional area.

41. The medical implant according to claim 35, wherein the protrusions are positioned on grid points of the two-dimensional regular grid wherein only a subset of grid points are covered by protrusions.

42. The medical implant according to claim 35, wherein the protrusions are arranged in parallel rows where the centre-to-centre distance between adjacent protrusions is different in adjacent rows.

43. The medical implant according to claim 35, wherein in the lateral cross-section of one or more protrusion(s) has a shape defined by circumference and/or geometry selected from circular, concave, convex, round, square, rectangular or a combination thereof.

44. The medical implant according to claim 35, wherein the center of the protrusions of said periodic topographical structure are placed on grid points of a 2-dimensional rectangular grid with grid constants a and b, and wherein:
 a) the grid is a square grid wherein the grid constant in each direction wherein a=b is in an interval between 2-8 µm, or
 b) the grid is rectangular with a grid constant a) in a first direction in an interval between 2-8 µm and with a grid constant b) in a second direction in an interval between 1-4 µm.

45. The medical implant according to claim 35, wherein at least a part of said surface is tantalum-coated and/or titanium-coated or any oxide thereof.

46. The medical implant according to claim 35, wherein at least a part of said surface consists of a biodegradable polymer as polylactic acid or poly(lactic-co-glycolic) acid.

47. The medical implant according to claim 35, further comprising an adsorbed compound selected from the group consisting of polypeptide, carbohydrate, growth hormone, antibody, antigen, glycoprotein, lipoprotein, DNA, RNA, polysaccharide, lipid, organic compound, and inorganic compound.

48. The medical implant according to claim 47, wherein said growth hormone is selected from the group consisting of BMP, EGF, TGF-beta, and IGF.

49. The medical implant according to claim 35, wherein said implant is a dental implant.

50. The medical implant according to claim 35, wherein said implant is an orthopedic implant.

* * * * *